United States Patent
Mazmanian et al.

(10) Patent No.: US 11,622,973 B2
(45) Date of Patent: Apr. 11, 2023

(54) IMMUNOMODULATING COMPOUNDS AND RELATED COMPOSITIONS AND METHODS

(71) Applicants: CALIFORNIA INSTITUTE OF TECHNOLOGY, Pasadena, CA (US); BRIGHAM AND WOMEN'S HOSPITAL, Boston, MA (US)

(72) Inventors: Sarkis K. Mazmanian, Porter Ranch, CA (US); June L. Round, Pasadena, CA (US); Ryan Michael O'Connell, Pasadena, CA (US); Dennis L. Kasper, Charlestown, MA (US)

(73) Assignees: California Institute of Technology, Pasadena, CA (US); Brigham and Women's Hospital, Boston, MA (US)

( * ) Notice: Subject to any disclaimer, the term of this patent is extended or adjusted under 35 U.S.C. 154(b) by 479 days.

(21) Appl. No.: 16/151,793

(22) Filed: Oct. 4, 2018

(65) Prior Publication Data
US 2019/0022128 A1    Jan. 24, 2019

Related U.S. Application Data

(63) Continuation of application No. 14/660,827, filed on Mar. 17, 2015, now abandoned, which is a continuation of application No. 13/464,876, filed on May 4, 2012, now abandoned, which is a continuation of application No. 12/267,602, filed on Nov. 9, 2008, now abandoned.

(60) Provisional application No. 61/196,046, filed on Oct. 14, 2008, provisional application No. 61/008,407, filed on Dec. 20, 2007, provisional application No. 61/002,705, filed on Nov. 9, 2007.

(51) Int. Cl.
*G01N 31/00* (2006.01)
*G01N 33/53* (2006.01)
*A61K 31/715* (2006.01)

(52) U.S. Cl.
CPC .................. *A61K 31/715* (2013.01)

(58) Field of Classification Search
None
See application file for complete search history.

(56) References Cited

U.S. PATENT DOCUMENTS

| | | | |
|---|---|---|---|
| 4,775,626 A | 10/1988 | Armenta et al. | |
| 5,236,940 A | 8/1993 | Audiau et al. | |
| 5,571,900 A | 11/1996 | Wiegand et al. | |
| 5,679,654 A | 10/1997 | Tzianabos et al. | |
| 5,700,787 A | 12/1997 | Tzianabos et al. | |
| 6,358,939 B1 | 3/2002 | Hayes et al. | |
| 7,026,283 B2 | 4/2006 | Fleming et al. | |
| 7,026,285 B2 | 4/2006 | Tzianabos et al. | |
| 7,083,777 B1 | 8/2006 | Tzianabos et al. | |
| 7,384,645 B2 | 6/2008 | Foster et al. | |
| 7,629,330 B2 | 12/2009 | Wang et al. | |
| 8,206,726 B2 | 6/2012 | Kasper et al. | |
| 9,057,070 B2 | 6/2015 | Mazmanian et al. | |
| 9,265,790 B2 | 2/2016 | Tzianabos et al. | |
| 9,452,189 B2 | 9/2016 | Mazmanian et al. | |
| 9,539,281 B2 | 1/2017 | Kasper et al. | |
| 2002/0146396 A1 | 10/2002 | Albert et al. | |
| 2003/0044425 A1 | 3/2003 | Burt et al. | |
| 2003/0059462 A1 | 3/2003 | Barenholz et al. | |
| 2003/0147865 A1 | 8/2003 | Salomon et al. | |
| 2003/0147922 A1 | 8/2003 | Capiau et al. | |
| 2003/0219413 A1* | 11/2003 | Comstock ............ | C07K 14/195 435/320.1 |
| 2004/0063685 A1 | 4/2004 | Ilzawa et al. | |
| 2004/0092433 A1 | 5/2004 | Wang et al. | |
| 2004/0219160 A1* | 11/2004 | Tzianabos ............ | A61K 9/0075 424/184.1 |
| 2005/0013831 A1 | 1/2005 | Foster et al. | |
| 2005/0020515 A1 | 1/2005 | Graff et al. | |
| 2005/0048587 A1 | 3/2005 | Rao et al. | |
| 2005/0063979 A1 | 3/2005 | Pickl et al. | |
| 2005/0119164 A1 | 6/2005 | Taylor et al. | |
| 2005/0147624 A1 | 7/2005 | Jennings et al. | |
| 2005/0181021 A1 | 8/2005 | Amb | |
| 2006/0029662 A1 | 2/2006 | Calias et al. | |
| 2006/0110412 A1 | 5/2006 | Desmons et al. | |
| 2006/0127387 A1 | 6/2006 | Zikria et al. | |
| 2006/0257852 A1 | 11/2006 | Rappuoli et al. | |
| 2006/0275752 A1 | 12/2006 | Sindhi | |
| 2006/0276378 A1 | 12/2006 | Wilson | |
| 2007/0041986 A1 | 2/2007 | Blaszczak et al. | |

(Continued)

FOREIGN PATENT DOCUMENTS

| | | |
|---|---|---|
| CA | 2800174 | 11/2011 |
| CN | 1818061 | 8/2006 |

(Continued)

OTHER PUBLICATIONS

Motta, A.C., van Oosterhout, A.J.M. (2006) T cells in asthma: Lessons from mouse models. Drug Discovery Today: Disease Models; vol. 3 No. 3 pp. 199-204 (Year: 2006).*
Motta, A.C., van Oosterhout, A.J.M. (2006) T cells in asthma: Lessons from mouse models. Drug Discovery Today: Disease Models vol. 32 No. 3 pp. 199-204 (Year: 2006).*
Dohi et al. (Current Opinion in Gastroenterology 2006, 22:651-657). (Year: 2006).*
Mazmanian et al. Cell, vol. 122, pp. 107-118, Jul. 15, 2005). (Year: 2005).*

(Continued)

*Primary Examiner* — Lisa V Cook
(74) *Attorney, Agent, or Firm* — Sheppard, Mullin, Richter & Hampton LLP

(57) ABSTRACT

Provided herein are compounds, compositions and methods for balancing a T-helper cell profile and in particular Th1, Th2, Th17 and Treg cell profiles, and related methods and compositions for treating or preventing an inflammatory condition associated with an imbalance of a T-helper cell profile.

13 Claims, 14 Drawing Sheets

Specification includes a Sequence Listing.

(56) References Cited

U.S. PATENT DOCUMENTS

| | | |
|---|---|---|
| 2007/0154991 A1 | 7/2007 | Comstock et al. |
| 2007/0207526 A1 | 9/2007 | Coit et al. |
| 2008/0057565 A1 | 3/2008 | Comstock et al. |
| 2008/0311140 A1 | 12/2008 | Lee et al. |
| 2009/0017472 A1 | 1/2009 | Stuhlmuller et al. |
| 2009/0124573 A1 | 5/2009 | Mazmanian et al. |
| 2009/0252708 A1 | 10/2009 | Fitzpatrick et al. |
| 2009/0317410 A1 | 12/2009 | Wang et al. |
| 2009/0317427 A1 | 12/2009 | Kasper et al. |
| 2010/0080760 A1 | 4/2010 | Hyde et al. |
| 2010/0221315 A1 | 9/2010 | Constantino et al. |
| 2010/0221755 A1 | 9/2010 | Lee et al. |
| 2010/0275282 A1 | 10/2010 | Round et al. |
| 2010/0311686 A1 | 12/2010 | Kasper et al. |
| 2010/0330166 A1 | 12/2010 | Ishida et al. |
| 2011/0002965 A1 | 1/2011 | Round |
| 2011/0251156 A1 | 10/2011 | Shen et al. |
| 2011/0287048 A1 | 11/2011 | Round et al. |
| 2012/0087895 A1 | 4/2012 | Mazmanian et al. |
| 2013/0039949 A1 | 2/2013 | Mazmanian |
| 2013/0064859 A1 | 3/2013 | Mazmanian |
| 2013/0121966 A1 | 5/2013 | Mazmanian et al. |
| 2013/0195802 A1 | 8/2013 | Moore |
| 2014/0072534 A1 | 3/2014 | Mazmanian et al. |
| 2014/0335131 A1 | 11/2014 | Mazmanian et al. |
| 2016/0022727 A1 | 1/2016 | Round et al. |
| 2016/0030464 A1 | 2/2016 | Mazmanian et al. |
| 2016/0143940 A1 | 5/2016 | Shen et al. |
| 2016/0151408 A1 | 6/2016 | Mazmanian et al. |
| 2016/0361343 A1 | 12/2016 | Mazmanian et al. |
| 2017/0003274 A1 | 1/2017 | Round et al. |
| 2018/0264026 A1 | 9/2018 | Round et al. |
| 2019/0022128 A1 | 1/2019 | Mazmanian et al. |
| 2020/0197436 A1 | 6/2020 | Round et al. |

FOREIGN PATENT DOCUMENTS

| | | |
|---|---|---|
| DE | 3704389 | 8/1988 |
| EP | 371414 | 6/1990 |
| EP | 382576 | 8/1991 |
| EP | 497524 | 8/1992 |
| EP | 1358885 | 11/2003 |
| EP | 1459757 A1 | 9/2004 |
| EP | 2217250 | 8/2010 |
| EP | 2422200 | 8/2010 |
| EP | 2555753 | 10/2011 |
| EP | 2571982 | 11/2011 |
| EP | 2764090 | 8/2014 |
| EP | 2994161 | 3/2016 |
| GB | 2286193 | 8/1995 |
| HK | 1201291 | 8/2015 |
| JP | S56128721 | 10/1981 |
| JP | H10507746 | 7/1998 |
| JP | 2002540074 | 11/2002 |
| JP | 2002541113 A | 12/2002 |
| JP | 2003204796 | 7/2003 |
| JP | 2004536028 A | 12/2004 |
| JP | 2006522135 A | 9/2006 |
| JP | 2010059201 | 3/2010 |
| JP | 2012524910 | 10/2012 |
| JP | 2016521284 | 7/2016 |
| JP | 6027961 | 11/2016 |
| JP | 6296367 | 3/2018 |
| JP | 6471888 | 2/2019 |
| WO | WO199531990 | 11/1995 |
| WO | WO199607427 | 3/1996 |
| WO | WO199632119 | 10/1996 |
| WO | WO199635433 | 11/1996 |
| WO | WO199842718 | 10/1998 |
| WO | WO199845335 | 10/1998 |
| WO | WO200001733 | 1/2000 |
| WO | 2000/059515 A2 | 10/2000 |
| WO | WO200207741 | 1/2002 |
| WO | 2002/045708 A2 | 6/2002 |
| WO | WO2003075953 | 9/2003 |
| WO | WO2003077863 | 9/2003 |
| WO | WO2003095606 | 11/2003 |
| WO | WO2004050909 | 6/2004 |
| WO | 2004/089407 A2 | 10/2004 |
| WO | WO2005010215 | 2/2005 |
| WO | WO2005094571 | 10/2005 |
| WO | WO2007040446 | 4/2007 |
| WO | 2007/092451 A2 | 8/2007 |
| WO | WO2008095141 | 8/2008 |
| WO | 2009/062132 A2 | 5/2009 |
| WO | WO2009149149 | 12/2009 |
| WO | WO2010124256 | 10/2010 |
| WO | WO2011056703 | 5/2011 |
| WO | WO2011127302 | 10/2011 |
| WO | WO2011146910 | 11/2011 |
| WO | WO2011153226 | 12/2011 |
| WO | WO2012027032 | 3/2012 |
| WO | WO2012103532 | 8/2012 |
| WO | WO2013009945 | 1/2013 |
| WO | WO2013019896 | 2/2013 |
| WO | WO2013036290 | 3/2013 |
| WO | WO2013052099 | 4/2013 |
| WO | WO2014182966 | 11/2014 |

OTHER PUBLICATIONS

Neuman (Translation Research, vol. 149, No. 4, Apr. 2007, p. 173-186; https://www.translationalres.com/articles/S1931-5244(06)00425-7/pdf). (Year: 2007).*

Dohi et al., (Curr. Opin. Gastroeter., 2006, 22:651-657) (Year: 2006).*

Lee et al. (Clinical Chemistry and Laboratory Medicine, vol. 46, No. 7, Jul. 1, 2008, 997-1003) (Year: 2008).*

Stenvinkel et al. (Kidney International, vol. 67 (2005), pp. 1216-1233). (Year: 2005).*

Rutgeerts et al., "Infliximab for induction and maintenance therapy for ulcerative colitis", N Engl J Med., Dec. 8, 2005, pp. 2462-2476, 353, Massachusetts Medical Society, Waltham, MA.

Sartor., "Mechanisms of disease: pathogenesis of Crohn's disease and ulcerative colitis", Nat Clin Pract Gastroenterol Hepatol., Jul. 1, 2006, pp. 390-407, 3, Macmillan Publishers Limited, Basingstoke, United Kingdom.

Sawada et al., "Leukocytapheresis in X Ulcerative Colitis: Results of a Multicenter Double-Blind Prospective Case-Control Studey with Sham Apheresis as Placebo Treatment", American Journal of Gastroenterology, Jun. 1, 2005, pp. 1362-1369, vol. 100, Macmillan Publishers Limited, Basingstoke, United Kingdom.

Scheinin et al., "Validation of theinterleukin-10 knockout mouse model of colitis: antitumour necrosis factorantibodies suppress the progression of colitis", Clin Exp Immunol., Jul. 2003, pp. 38-43, vol. 133, Issue 1, John Wiley & Sons, Inc., Hoboken,NJ.

Sellon et al. "Resident enteric bacteria are necessary for development of spontaneous colitis and immune system activation in interleukin-10-deficient mice", Infect Immun., Nov. 1998, pp. 5224-5231, vol. 66 No. 11, American Society for Microbiology, Washington DC.

Smith et al. "Use of axenic animals in studying theadaptation of mammals to their commensal intestinal microbiota", Semin Immunol., Apr. 2007, pp. 59-69, vol. 19, Issue 2, Elsevier, Amsterdam, Netherlands.

Stefanelli et al., "New insights into inflammatory bowel disease pathophysiology: paving the way for novel therapeutic targets", Current Drug Targets, May 2008, pp. 413-418, vol. 9, No. 5, Ingenta, Oxford, United Kingdom.

Stingele et al., "Zwitterionic Polysaccharides Stimulate T Cells with No Preferential Vbeta Usage and Promote Anergy, Resulting in Protection against Experimental Abscess Formation", The Journal of Immunology, Feb. 1, 2004, pp. 1483-1490, vol. 172, Issue 3, American Association of Immunologists, Rockville, MD.

Stockinger et al., "Differentiation and function of Th17 T cells", Current Opinion in Immunology, Jun. 2007, pp. 281-286, vol. 19, Issue 3, Elsevier, Amsterdam, Netherlands.

(56) References Cited

OTHER PUBLICATIONS

Strachan et al. "Hay fever, hygiene, and household size", BMJ, Nov. 18, 1989, pp. 1259-1260, 299 (6710), BMJ Publishing Group Ltd., London, United Kingdom.
Strauch et al., "Influence of intestinal bacteria on induction of regulatory T cells: lessons from a transfer model of colitis", Gut, Jun. 29, 2005, pp. 1546-1552, vol. 54, Issue 11, BMJ Publishing Group Ltd., London, United Kingdom.
Strober, "The multifaceted influence of the mucosal microflora on mucosal dendritic cell responses", Immunity, Sep. 18, 2009, pp. 377-388, vol. 31, Issue 3, Elsevier, Amsterdam, Netherlands.
Stumhofer et al., "Interleukins 27 and 6 induce STAT3-mediated T cell production of interleukin 10", Nat Immunol, Nov. 11, 2007, pp. 1363-1371, 8, Macmillan Publishers Limited, Basingstoke, United Kingdom.
Supplementary European Search Report for EP app. No. EP2217250 issued by the EPO dated Dec. 8, 2010.
Sutmeuller et al., "Toll-like receptor 2 controls expansion and function of regulatory T cells", J. Clin. Invest., Feb. 1, 2006, pp. 485-494, vol. 116, Issue 2, American Society for Clinical Investigation, Ann Arbor, MI.
Taurog et al., "The germfree state prevents development of gut and joint inflammatory disease in HLA-B27 transgenic rats", J Exp Med., Dec. 1, 1994, pp. 2359-2364, 180 (6), The Rockefeller University Press, New York, NY.
The Language of Prevention, National Public Health Partnership, 2006, 9 pages.
Turnbaugh et al., "An obesity-associated gut microbiome with increased capacity forenergy harvest", Nature, Dec. 21, 2006, pp. 1027-1031, 444(7122).
Turnbaugh et al., "The human microbiome project: exploring the microbial part of ourselves in a changing world", Nature, Oct. 18, 2007, pp. 804-810. vol. 449, Issue 7164, Nature Publishing Group, London, United Kingdom.
Tzianabos et al. "Structural Characteristics of Polysaccharides that Induce Protection Against Intra-Abdominal Abscess Formation" Infection and Immunity, Nov. 1, 1994, pp. 4881-4886, vol. 62, No. 11, American Society for Microbiology, Rockville, MD.
Tzianabos et al. "The capsular polysaccharide of Bacteroides fragilis comprises two ionically linked polysaccharides", J Biol CheM, Sep. 5, 1992, p. 18230-18235, 267, American Society for Biochemistry and Molecular Biology, Rockville, MD.
Van Maren et al., "Toll-like receptor signalling on Tregs: to suppress or not to suppress?", Immunology, Aug. 2008, pp. 445-452, vol. 124, Issue 4, John Wiley & Sons, Inc., Hoboken, NJ.
Videla et al., "Role of intestinal microflora in chronic inflammation and ulceration of therat colon", Gut, 1994, pp. 1090-1097, vol. 35, Issue 8, BMJ Publishing Group Ltd., London, United Kingdom.
Wang et al., "A bacterial carbohydrate links innate and adaptive responses through Toll-like receptor 2", J. Exp.Med., Dec. 18, 2006, pp. 2853-2863, vol. 203, Issue 13, The Rockefeller University Press, New York, NY.
Wong et al., "Activation of Peripheral Th17 Lymphocytes in Patients with Asthma", Immunological Investigations, Sep. 19, 2009, pp. 652-664, vol. 38, Issue 7, Informa UK Limited, San Francisco, CA.
Xavier et al., "Commensal flora: wolf in sheep's clothing", Gastroenterology, Apr. 2005, pp. 1122-1126, vol. 128, Issue 4, Elsevier Inc., Amsterdam, Netherlands.
Young et al., "In vitro and in vivo characterization of Helicobacter hepaticus cytolethal distending toxin mutants", Infect Immun., May 2004, pp. 2521-2527, vol. 72 No. 5, American Society for Microbiology, Washington DC.
Office Action for U.S. Appl. No. 13/464,876, dated Feb. 20, 2014, 20 pages.
Stingele et al., "Zwitterionic polysaccharides stimulate T cells with no preferential V beta usage and promote energy, resulting in protection against experimental abscess formation", J. Immunol., Feb. 1, 2004, pp. 1483-1490, vol. 172, Issue 3, The American Association of Immunologists, Inc., Rockville, MD.

Written Opinion for PCT/US2008/082928, dated Jun. 30, 2009, 5 pages.
Stenvinkel et al., "IL-10, IL-6, and TNF-α: central factors in the altered cytokine network of uremia—the good, the bad, and the ugly", Kidney International, Apr. 2005, pp. 1216-1233, vol. 67, Issue 4, Elsevier, New York City, NY.
Dohi et al., "Type 1 and 2 T helper cell-mediated colitis", Current Opinion in Gastroenterology, Nov. 2006, pp. 651-657, vol. 22—Issue 6, Lippincott Williams & Wilkins, Philadelphia, PA.
"Asthma" from the Centers for Disease Control and Prevention, [retrieved Nov. 13, 2012]. Retrieved from the internet www.cdc.gov/asthma/aag/2010/overview. Html.
"Ulcerative Colitis" from the National Institutes of Health [online], [retrieved Nov. 9, 2012]. Retrieved from the internet www.digestive.niddk.nih.gov/ddiseases/pubs/colitis/UlcerativeColitis508.pdf.
Adkins et al., "Early Block in Maturation Is Associated with Thymic Involution in Mammary Tumor-Bearing Mice", J Immunology, Jun. 1, 2000, pp. 5635-5640, vol. 164, Issue 11, American Association of Immunologists, Rockville, MD.
Adkins, "T-cell function in newborn mice and humans", Review Immunology Today, Jul. 1, 1999, pp. 330-335, vol. 20, Issue 7, Elsevier, Amsterdam, Netherlands.
Adkins, "Development of neonatal Th1/Th2 function", Int Rev Immunol, 2000; pp. 157-171,19 (2-3), Taylor and Francis Group, Abingdon, United Kingdom.
Adkins et al., "Exclusive Th2 Primary Effector Function in Spleens but Mixed Th1/Th2 Function in Lymph Nodes of Murine Neonates"'Journal Immunol, Mar. 1, 2000, pp. 2347-2353,164(5), American Association of Immunologists, Rockville, MD."
Afzali, "The role ofT helper 17(Th17) and regulatory T cells (Treg) in human organ transplantation and autoimmune disease", Clinical and Experimental Immunology, Apr. 2007, pp. 32-46, vol. 148, Issue 1, John Wiley & Sons, Inc., Hoboken, NJ.
Amsen et al., "Instruction of distinct CD4 T helper cell fates by different notch ligands on antigen-presenting cells", Cell, May 14, 2004, pp. 515-526, vol. 117, Issue 4, Elsevier, Amsterdam, Netherlands.
Asseman et al., "An essential role forinterleukin 10 in the function of regulatory T cells that inhibit intestinal inflammation", J Exp Med., Oct. 4, 1999, pp. 995-1004, 190 (7), Rockefeller University Press, New York, NY.
Atarashi et al., "ATP drives lamina propria TH17 cell differentiation", Nature, Oct. 9, 2008, pp. 808-812, vol. 455, Issue 7214, Macmillan Publishers Limited, Basingstoke, United Kingdom.
Awasthi, "Interplay between effector Th17 and regulatory T cells", J Clin Innunol, Nov. 2008, pp. 660-670, 28(6), Springer International Publishing AG, Cham, Switzerland.
Bach, The effect of infections on susceptibility to autoimmune and allergic diseases, N Engl J Med., Sep. 19, 2002, pp. 911-920, vol. 347, No. 12, Massachusetts Medical Society, Waltham, MA.
Belkaid et al., "Regulatory T cells in the control of host-microorganism interactions", Annu. Rev. Immunol., 2009. pp. 551-589, vol. 27, Annual Reviews, Palo Alto, CA.
Bell, "Function of CD4 T cell subsets in vivo: expression of CD45R isoforms", Semin Immuno, Feb. 1, 1992, pp. 43-50, 14(1), Elsevier, Amsterdam, Netherlands.
Bilo et al., "Diagnosis of Hymenoptera venom allergy", Allergy, Nov. 2005, pp. 1339-1349, vol. 60, Issue 11, John Wiley & Sons, Inc., Hoboken, NJ.
Boguniewicz, "The autoimmune nature of chronic urticarial", Allergy and Asthma Proceedings, Sep.-Oct. 2008, pp. 433-438, vol. 29, No. 5, Ingenta, Oxford, United Kingdom.
Bouma et al., "The immunological and genetic basis of inflammatory bowel disease", Nat. Rev. Immunol., 2003,pp. 521-533, 3, Macmillan Publishers Limited, Basingstoke, United Kingdom.
Braat et al., "A Phase I Trial With Transgenic Bacteria Expressing interleukin-1 0 in Crohn's Disease" Clinical Gastroenterology and Hepatology, Jun. 2006, pp. 754-759, vol. 4, Issue 6, Elsevier, Amsterdam, Netherlands.
Bregenholt, "S. Cells and cytokines in the pathogenesis of inflammatory bowel disease: newinsights from mouse T cell transfer models", Exp Clin Immunogenet, Jun. 2000, pp. 115-129, vol. 17, No. 3, S. Karger AG, Basel, Switzerland.

(56) References Cited

OTHER PUBLICATIONS

Cahill et al., "Inflammatory bowel disease: an immunity-mediated condition triggered by bacterial infection with Helicobacter hepaticus", Infect Immun., Aug. 1997, pp. 3126-3131, vol. 65 No. 8, American Society for Microbiology, Washington, DC.
Chen et al. "Pertussis Toxin by Inducing IL-6 Promotes the Generation of IL-17-Producing CD4 Cells".Journal of Immunology, May 15, 2007, pp. 6123-6129, vol. 178, No. 10, American Association of Immunologists, Rockville, MD.
Cho et al., "Recent Insights Into the Genetics of Inflammatory Bowel Disease", Gastroenterology, May 2011, pp. 1704-1712, vol. 140, Elsevier, Amsterdam, Netherlands.
Communication pursuant to Article 94(3) EPC for European Application No. 08847489.5 filed in the name of California Institute of Technology, dated Aug. 7, 2013.
Coombes et al., "Regulatory T cells and intestinal homeostasis", Immunol. Rev., Apr. 2005, pp. 184-194, vol. 204, Issue 1, John Wiley & Sons, Inc., Hoboken, NJ.
Coyne et al., "Mpi recombinase globally modulates the surface architecture of a human commensal bacterium", PNAS, Sep. 2, 2003, pp. 10446-10451, vol. 100 No. 18, National Academy of Sciences, Washington, D.C.
Decision on Rejection for JP2010-533311 dated Oct. 29, 2013 in the name of California Instituteof Technology.(English Translation+ Japanese Original).
Definition of "prevention" from the Institute for International Medical Education [online], [Retrieved on Mar. 24, 2011], Retrieved from the internet. www.iime.org/glossary.htm. Published Feb. 2002, p. 1, 2, 26 ,27 and 39.
Dethlefsen et al. "An ecological and evolutionary perspective on human-microbe mutualism and disease", Nature, Oct. 18, 2007, pp. 811-818, 449, Macmillan Publishers Limited, Basingstoke, United Kingdom.
Dong, "Diversification of T-helper-celllineages: finding the family root of IL-17 producing cells", Nat Rev Immunol, Mar. 17, 2006, pp. 329-334, vol. 6, Issue 4, Macmillan Publishers Limited, Basingstoke, United Kingdom.
Elson et al., "Monoclonal anti-interleukin 23 reverses active colitis in aT cell-mediated model in mice", Jun. 2007, pp. 2359-2370, vol. 132, Issue 7, Elsevier, Amsterdam, Netherlands.
Elson, "Commensal bacteria as targets in Crohn's disease" Gastroenterology Jul. 2000, pp. 254-257, vol. 119, Issue 1, Elsevier, Amsterdam, Netherlands.
EP Communication 94.3 dated Aug. 7, 2013 for EP Application 08847489.5 filed on Nov. 9, 2008 inthe name of California Institute of Technology.
European Search Opinion for EP app. No. EP2217250 issued by the EPO dated Dec. 8, 2010.
Feuerer et al., "Foxp3+ regulatory T cells: differentiation, specification, subphenotypes", Nat Immunol., Jun. 18, 2009, p. 689-695, vol. 10,Issue 7, Macmillan Publishers Limited, Basingstoke, United Kingdom.
Final Office Action issued for U.S. Appl. No. 12/267,602, filed Nov. 9, 2008 in the name of California Institute of Technology and Brigham and Women's Hospital; dated Feb. 6, 2012.
Final Office Action issued in U.S. Appl. No. 10/814,620, filed Mar. 31, 2004 in the name of Adhur O. Tzianabos, dated Oct. 7, 2009.
Final Office Action dated June 10, 2013 for U.S. Appl. No. 12/831,131, filed Jul. 6, 2010 in the name of June L. Round.
Fontenot et al., "Regulatory T cell lineage specification by the forkhead transcription factor foxp3", Immunity, Mar. 2005, pp. 329-341, vol. 22, Issue 3, Elsevier, Amsterdam, Netherlands.
Frank et al., "Molecular-phylogenetic characterization of microbial community imbalances in human inflammatory bowel diseases", Proc Natl Acad Sci USA, Aug. 21, 2007, pp. 13780-13785, vol. 104 No. 34, PNAS, Washington, DC.
Fujino et al., "Increased expression of interleukin 17 in inflammatory bowel disease", Gut, 2003; pp. 65-70, 52, BMJ Publishing Group, London, United Kingdom.

Gaboriau-Rauthiau et al., "The key role of segmented filamentous bacteria in the coordinated maturation of gut helper T cell responses", Immunity, Oct. 16, 2009, pp. 677-689,vol. 31, Issue 4, Elsevier, Amsterdam, Netherlands.
Gerard et al., "Interleukin 10 reduces the release of tumor necrosis factor and prevents lethality in experimental endotoxemia", J. Exp. Med., Feb. 1, 1993, pp. 547-550, 177 (2): 547, Rockefeller University Press, New York, NY.
Gilbert et al., "Toward Effective Probiotics for Autism and Other Neurodevelopmental Disorders", Cell, Dec. 19, 2013, pp. 1446-1448,vol. 155, Issue 7, Elsevier, Amsterdam, Netherlands.
Gill et al., "Metagenomic analysis of the human distal gut microbiome", Science, Jun. 2, 2006, pp. 1355-1359, vol. 312, Issue 5778, American Association for the Advancement of Science, Washington, D.C.
Greenberger, Drug allergy, J Allergy Clin Immunol., Feb. 2006, pp. S464-S470, vol. 117, Issue 2, Supplement 2, Elsevier, Amsterdam, Netherlands.
Groux et al., "A CD4+ T-cell subset inhibits antigen-specific T-cell responses and prevents colitis", Nature, Oct. 16, 1997, pp. 737-742, 389, Macmillan Publishers Limited, Basingstoke, United Kingdom.
Hue et al., Interleukin-23 drives innate and T cell-mediated intestinal inflammation:, J Exp Med., Oct. 9, 2006,, pp. 2473-2483, 203 (11), The Rockefeller University Press, New York, NY.
Ivanov et al., "Induction of intestinal Th17 cells by segmented filamentous bacteria", Cell, Oct. 15, 2009, pp. 485-498, vol. 139, Issue 3, Elsevier Inc., Amsterdam, Netherlands.
Ivanov et al., "Specific microbiota direct the differentiation of IL-17-producing T-helper cells in the mucosa of the small intestine", Cell Host Microbe, Oct. 16, 2008, pp. 337-349, vol. 4, Issue 4, Elsevier Inc., Amsterdam, Netherlands.
Ivanov et al., "Transcriptional regulation of Th17 cell differentiation", Semin Immunol, Dec. 200, pp. 409-417, vol. 19, Issue 6, Elsevier Inc., Amsterdam, Netherlands.
Izcue et al., "Regulatory T cells suppress systemic and mucosal immune activation to control intestinal inflammation", Immunol Rev., Aug. 2006, pp. 256-271, vol. 212, Issue 1, John Wiley & Sons, Inc., Hoboken, NJ.
Jyonouchi, "Non-lgE Mediated Food Allergy", Inflammation & Allergy-Drug Targets, Sep. 2008, pp. 173-180.vol. 7, No. 3, Ingenta, Oxford, United Kingdom.
Kalka-Moll et al., "Zwitterionic Polysaccharides stimulate T cells by MHC class II-Dependent Interactions", The Journal of Immunology, Dec. 1, 2002, p. 6149-6153, vol. 169, Issue 11, American Association of Innunologists, Rockville, MD.
Kidd, "Th1/Th2 Balance: The hypothesis, its limitations, and implications for health and disease", Alternative Medicine Review, 2003, pp. 223-246, vol. 8, No. 3, Thorne Research, Inc., Dover, ID.
Kirjavainen et al. "Healthy gut microflora and allergy: factors influencing development of the microbiota",Ann Med., 1999, pp. 288-292, vol. 31, Issue 4, Informa UK Limited, San Francisco, CA.
Kormelink et al., "Atopic and non-atopic allergic disorders: current insights into the possible involvementof free immunoglobulin light chains", Clinical and Experimental Allergy, Jan. 2009, pp. 33-42, vol. 39, Issue 1, John Wiley & Sons, Inc., Hoboken, NJ.
Kuhn et al., "Interleukin-1 0deficient micedevelop chronic enterocolitis", Cell, Oct. 22, 1993, pp. 263-274, vol. 75, Issue 2, Elsevier Inc., Amsterdam, Netherlands.
Kullberg et al., "Bacteria-triggered CD4(+) T regulatory cells suppress Helicobacter hepaticus-induced colitis", JExp Med., Aug. 19, 2002, pp. 505-515, 196 (4): 505, The Rockefeller University Press, New York, NY.
Kullberg et al., "Helicobacter hepaticus Triggers Colitis in Specific-Pathogen-Free Interleukin-1 0 (IL-1 0)-Deficient Mice through an IL-12- and Gamma Interferon-Dependent Mechanism", Infection and Immunity Nov. 1998, pp. 5157-5166, vol. 66 No. 11, American Society for Microbiology, Washington DC.
Kullberg et al., "IL-23 plays a key role in Helicobacter hepaticus-induced T celldependentcolitis", J Exp Med., Oct. 9, 2006, pp. 2485-2494,203 (11): 2485, The Rockefeller University Press, New York, NY.
Kullberg et al., "Induction of colitis by a CD4+ T cell clone specific for a bacterial epitope", Proc Natl Acad Sci USA, Dec. 23, 2003, pp. 15830-15835, vol. 100 No. 26, PNAS, Washington, DC.

(56) References Cited

OTHER PUBLICATIONS

Lee et al., Clinical Chemistry and Laboratory Medicine, Jul. 1, 2008, pp. 997-1003, vol. 46, No. 7., Watler de Gruyter GmbH, Berlin, Germany.
Ley et al., "Ecological and evolutionary forces shapingmicrobial diversity in the human intestine", Cell, Feb. 24, 2006, pp. 837-848,vol. 124, Issue 4, Elsevier, Amsterdam, Netherlands.
Lin et al., "Regulatory T cell development in the absence of functional Foxp3", Nat. Immunol., Mar. 2007, pp. 359-368, vol. 8, Issue 4, Nature Publishing, London, United Kingdom.
Liu et al., "Regulation of surface architecture by symbiotic bacteria mediates host colonization", Proc Natl Acad Sci USA, Mar. 11, 2008, pp. 3951-3956, vol. 105 No. 10, PNAS, Washington, DC.
Liu et al., "Toll-like receptor 2 signaling modulates the functions of CD4+ CD25+ regulatory T cells", Proc. Natl.Acad. Sci. USA, May 2, 2006, pp. 7048-7053, vol. 103 No. 18, PNAS, Washington, DC.
Maloy et al., "CD4+CD25+ T(R) cells suppress innate immune pathology through cytokine-dependent mechanisms", J Exp Med., Jan. 6, 2003, pp. 111-119, 197, The Rockefeller University Press, New York, NY.
Maynard et al., "Diversity in the contribution of interleukin-10 to T-cell-mediated immune regulation", Immunol. Rev., Dec. 2008, pp. 219-233, vol. 226, Issue 1, John Wiley & Sons, Inc., Hoboken, NJ.
Mazmanian et al., "A microbial symbiosis factorprevents intestinal inflammatory disease", Nature, May 29, 2008, pp. 620-625, vol. 453, Macmillan Publishers Limited, Basingstoke, United Kingdom.
Mazmanian et al., "A microbial symbiosis prevents intestinal inflammatory disease" Nature, May 29, 2008, pp. 620-625, 453, Macmillan Publishers Limited, Basingstoke, United Kingdom.
Mazmanian et al., "An immunomodulatory molecule of symbiotic bacteria directs maturation of the host immune system", Cell, Jul. 15, 2005, pp. 107-118, vol. 122, Issue 1, Elsevier, Amsterdam, Netherlands.
Mazmanian et al., ""Bacterial Immunomodulatory Regulation during Mammalian Health andDisease"", Harvard Medical School, Brigham and Women's Hospital. (Oct. 11, 2005).
Mazmanian et al., "The Evolution of Symbiosis: From Bacteria to Commensal to Beneficial Microbe", Nature, May 29, 2008, pp. 620-625, 453, Macmillan Publishers Limited, Basingstoke, United Kingdom.
Mazmanian et al., "The love-hate relationship between bacterial polysaccharides and the host immune system", Nature Reviews Immunology, Nov. 2006, pp. 849-858, vol. 6, No. 11, Nature Publishing Group, London, United Kingdom.
Merriam-Webster. Hypothesize. 2013. Web<http://www.merriam-webster.com/dictionary/hypothesize>.
Merriam-Webster. Suggest. 2013. Web<http://www.merriam-webster.com/dictionary/suggest>.
Motta et al., "T cells in asthma: Lessons from mouse models", Drug Discovery Today: Disease Models, Autumn 2006, pp. 199-204, vol. 3, Issue 3, Elsevier, Amsterdam, Netherlands.
Neurath et al., "TNBS-colitis", Int Rev Immunol., 2000, pp. 51-62, 19(1), Informa UK Limited, San Francisco, CA.
Niess et al., "Commensal gut flora drives the expansion of proinflammatory CD4 T cells in the colonic laminapropria under normal and inflammatory conditions", J Immunol., Jan. 1, 2008, pp. 559-568, vol. 180, Issue 1, American Association of Immunologists, Rockville, MD.
Non-Final Office Action issued for U.S. Appl. No. 12/267,602, filed Nov. 9, 2008 in the name of California Institute of Technology and Brigham and Women's Hospital; dated Jul. 15, 2011.
Non-Final Office Action dated Jul. 9, 2013 for U.S. Appl. No. 13/464,876, filed May 4, 2012 in the name of Sarkis Mazmanian et al.
Non-Final Office Action dated Nov. 15, 2012 for U.S. Appl. No. 12/831,131, filed Jul. 6, 2010 in the name of June L. Round.
Notice of Reasons for Rejection for JP 2010-533311 dated May 14, 2013 in the name of California Institute of Technology. (English Translation).

O'Garra et al., "IL-10-producing and naturally occurring CD4+ Tregs: limiting collateral damage", J Clin Invest, Nov. 15, 2004, pp. 1372-1378, 114(10), National Center for Biotechnology Information, Bethesda MD.
O'Hara et al., "The gut flora as a forgotten organ", EMBO, Jul. 1, 2006, pp. 688-693,vol. 7, Issue 7, EMBO, Heidelberg, Germany.
Ostman et al., "Impaired regulatory T cell function in germ-free mice", European Journal of Immunology, Sep. 2006, pp. 233-246, vol. 36, Issue 9, John Wiley & Sons, Inc., Hoboken, NJ.
Palmer et al., "Development of the Human Infant Intestinal Microbiota", PLoS Bioi., Jun. 26, 2007, pp. 1556-1573 vol. 5, Issue 7, e177, PLOS, San Francisco, CA.
Pamer, "Immune responses to commensal and environmental microbes", Nat Immunol., Oct. 19, 2007, pp. 1173-1178, 8,Macmillan Publishers Limited, Basingstoke, United Kingdom.
Paxton et al., "Mucosa-associated bacterial flora of the human colon", J Med Microbial., Jan. 1, 1997, pp. 85-91, 46, The Pathological Society of Great Britain and Ireland, London, United Kingdom.
PCT Search Report for PCT/US2008/082928 in the name of California Institute of Technology filed on Nov. 9, 2008.
Poonawalla et al., "Urticaria—A Review", Am J Clin Dermatol., 2009, pp. 9-21, vol. 10, No. 1, Springer, Berlin, Germany.
Powrie et al., "Immunology. Regulating the regulators", Science, Feb. 14, 2003, pp. 1030-1031, 299(5609), AAAS, Washington, DC.
Prescott et al., "Sudden-onset severe acute asthma: Clinical features and response to therapy", AcademicEmerqency Med., Jul. 1998, pp. 695-701, vol. 5, Issue 7, John Wiley & Sons, Inc., Hoboken, NJ.
Rakoff-Nahoum et al., "Recognition of commensal microflora by toll-like receptors is required for intestinalhomeostasis", Cell, Jul. 23, 2004, pp. 229-241, vol. 118, Issue 2, Elsevier Inc., Amsterdam, Netherlands.
Restriction Requirement issued by the USPTO for U.S. Appl. No. 12/267,602 dated Mar. 17, 2011.
Restriction Requirement issued in U.S. Appl. No. 13/464,876, filed May 4, 2012 in the name of Sarkis Mazmanian, dated Feb. 20, 2013.
Restriction Requirement dated Jul. 11, 2012 for U.S. Appl. No. 12/831,131, filed Jul. 6, 2010 in the name of June L. Round.
Round et al., "The gut microbiota shapes intestinal immune responses during health and disease", Nat RevImmunol., May 1, 2009, pp. 313-323, vol. 9, Macmillan Publishers Limited, Basingstoke, United Kingdom.
Rubtsov et al., "Regulatory T cell-derived interleukin-1 0 limits inflammation at environmental interfaces", Immunity, Apr. 11, 2008, pp. 546-558, vol. 28, Issue 4, Elsevier Inc., Amsterdam, Netherlands.
Ruiz-Perez et al., "Modulation of surgical fibrosis by microbial zwitterionic polysaccharides", PNAS, Nov. 15, 2005, p. 16753-16758, vol. 102, No. 46, PNAS, Washington, DC.
[No Author Listed] "MS the Disease". National Multiple Sclerosis Society. Downloaded from the internet at http://www.nationalmssociety.org/About-the-Society/Press-Room/MS-the-Disease on Dec. 19, 2016, 4 pages (website copyright 2014).
[No Author Listed] Drug Absorption, Bioavailability, and Routes of Administration. Goodman & Oilman's The Pharmacological Basis of Therapeutics, Tenth Edition, McGraw-Hill Medical Publishing Edition, New York, 2001, pp. 5-8.
[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.
Abreu, M.T. et al. "Measurement of vitamin D levels in inflammatory bowel disease patients reveals a subset of Chrohn's disease patients with elevated 1,25-dihydroxyvitamin D and low bone mineral density" Gut, 2004, 53(8) pp. 1129-1136.
"Abscess" from Wikipedia, dated May 9, 2015 (6 pages) https://en.wikipedia.orgA/Wiki/Abscess.
Adams JS, et al. (2008) Unexpected actions of vitamin D: new perspectives on the regulation of innate and adaptive immunity. Nat Clin Pract Endocrinol Metab 4: 80- 90.
Adams JS, et al. (2012) Extrarenal expression of the 25-hydroxyvitamin D-1-hydroxylase. Archives of biochemistry and biophysics 523: 95-102.

(56) References Cited

OTHER PUBLICATIONS

Advisory Action for U.S. Appl. No. 13/112,725, filed May 20, 2011 on behalf of June L. Round, dated Mar. 4, 2014. 3 pages.
Aharoni et al., Bystander suppression of experimental autoimmune encephalomyelitis by T cell lines and clones of the type induced by copolymer 1. J Neuroimmunol. Nov. 2, 1998;91(1-2):135-46.
Aharoni et al., Copolymer 1 induces T cells of the T helper type 2 that crossreact with myelin basic protein and suppress experimental autoimmune encephalomyelitis. Proc Natl Acad Sci USA. Sep. 1997 30;94(20):10821-6.
Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Ai-Bader et al. "Activation of Human Dendritic Cells Is Modulated by Components of the Outer Membranes of Neisseria meningitidis" Infection and Immunity. Oct. 2003; 71(10): 5590-5597).
Allen AC, et al. (2012) "A pilot study of the immunological effects of high-dose vitamin D in healthy volunteers". Multiple Sclerosis Journal; 2012; vol. 18; No. 12; pp. 1797-1800.
Amidon et al., "Proposed New USP General Information Chapter, Excipient Performance <1059>", Pharmacopeia forum, Nov.-Dec. 2007, pp. 1311-1323, vol. 33(6), The United States Pharmacopeia Convention, Rockville, MD.
Anderson AC, et al. (2012) A transgenic model of central nervous system autoimmunity mediated by CD4+ and CD8+ T and B cells. Journal of immunology 188: 2084-2092.
Arnon et al., New insights into the mechanism of action of copolymer 1 in experimental allergic encephalomyelitis and multiple sclerosis. J Neural. Apr. 1996;243(4 Suppl I):S8-13. Review.
Asadullah et al., Interleukin-10 therapy-review of a new approach. Pharmacol Rev. Jun. 2003;55(2):241-69.
Ascherio A, et al. "Vitamin D and multiple sclerosis". Lancet Neurology; Jun. 2010; vol. 9: pp. 599-612.
Azzawi et al., Identification of activated T lymphocytes and eosinophils in bronchial biopsies instable a topic asthma. Am Rev Respir Dis. Dec. 1990; 142(6 Pt 1):1407-13.
Baecher-Allan CM, et al. (2011) CD2 costimulation reveals defective activity by human CD4+CD25(hi) regulatory cells in patients with multiple sclerosis. Journal of immunology 186: 3317-3326.
Banerjee et al. "Expansion of FOXP3 high regulatory T cells by human dendritic cells (DCs) in vitro and after injection of cytokine-matured DCs in myeloma patients" Blood. 2006; 108: 2655-2661.
Baranzini SE, et al. (2010) Genome, epigenome and RNA sequences of monozygotic twins discordant for multiple sclerosis. Nature 464: 1351-1356.
Barnes, M.J., et al. (2009). "Regulatory T cells reinforce intestinal homeostasis". Immunity 31, 401-411.
Bar-On L, et al. (2010) Defining in vivo dendritic cell functions using CD11 c-DTR transgenic mice. Methods in molecular biology 595: 429-442.
Barrat FJ, et al. (2002) In vitro generation of interleukin 10-producing regulatory CD4(+) T cells is induced by immunosuppressive drugs and inhibited by T helper type 1 (Th1)- and Th2-inducing cytokines. J Exp Med 195: 603-616.
Barutca et al., Prevention of interleukin-2-induced severe bronchospasm with salbutamol. J Aerosol Med. 2003 Summer;16(2):183-4.
Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.
Batta et al., Conformational stabilization of the altruronic acid residue in the O-specific polysaccharide of Shigella sonnei/Plesiomonas shigelloides. Carbohydr Res. Dec. 1998;305(1):93-9.
Bayley DP et al. Analysis of cepA and other Bacteroides fragilis genes reveals a unique promoter structure. (2000) FEMS Microbial Lett 193:149-54.
Bazan et al., Unraveling the structure of IL-2. Science. Jul. 17, 1992;257(5068):410-3.
Becker et al., "TGF—Suppresses Tumor Progression in Colon Cancer by Inhibition of IL-6 trans-Signaling," Immunity, vol. 21, 491-501 (2004).
Becker KG, et al. (1998) Clustering of non-major histocompatibility complex susceptibility candidate loci in human autoimmune diseases. Proc Natl Acad Sci U S A 95: 9979-9984.
Berer et al., Commensal gut flora and brain autoimmunity: a love or hate affair? Acta Neuropathol. May 2012;123(5):639-51. doi: 10.1007/s00401-012-0949-9. EpubFeb. 10, 2012.
Berer et al., Commensal microbiota and myelin autoantigen cooperate to trigger autoimmune demyelination. Nature. Oct. 26, 2011;479(7374):538-41. doi: 10.1038/nature10554.
Berggren et al., Decreasing serum concentrations of all-trans, 13-cis retinoic acids and retinal during fasting and caloric restriction. J Intern Med. Mar. 2003;253(3):375-80.
Bernatowska-Matuszkiewicz et al., IgG subclasses and antibody response to pneumococcal capsular polysaccharides in children with severe sinopulmonary infections and asthma. Immunol Investi. 1991;20(2):173-185.
Bettelli E, et al. (2003) Myelin oligodendrocyte glycoprotein-specific T cell receptor transgenic mice develop spontaneous autoimmune optic neuritis. The Journal of experimental medicine 197: 1073-1081.
Bettelli, E. et al. "Reciprocal developmental pathways for the generation of pathogenic effector TH17 and regulatory T cells" Nature vol. 441 pp. 235-238 (2006).
Bhaduri et al., Simple and rapid method for disruption of bacteria for protein studies. Appl Environ Microbial. Oct. 1983;46(4):941-3.
Bhat R, et al. (2009) Innate and adaptive autoimmunity directed to the central nervous system. Neuron 64: 123-132.
Blander et al., Toll-dependent selection of microbial antigens for presentation by dendritic cells. Nature. Apr. 6, 2006;440(7085):808-12. Epub Feb. 19, 2006.
Blomfield et al. Lrp stimulates phase variation of type 1 fimbriation in E. coli K12. J. Bacteriology 175, 27-36, 1993.
Blumberg & Powrie, "Microbiota, Disease, and Back to Health: A Metastable Journey," Sci. Transl. Med., vol. 4, 137rv7 (2012).
Bollrath et al., "gp130-Mediated Stat3 Activation in Enterocytes Regulates Cell Survival and Cell-Cycle Progression during Colitis-Associated Tumorigenesis," Cancer Cell, vol. 15, 91-102 (2009).
Borsellino et al., Expression of ectonucleotidase CD39 by Foxp3+ Treg cells: hydrolysis of extracellular ATP and immune suppression. Blood. Aug. 15, 2007;110(4):1225-32. Epub Apr. 20, 2007.
Bouskra, D., et al. (2008). Lymphoid tissue genesis induced by commensals through NOD1 regulates intestinal homeostasis. Nature 456, 507-510.
Braun et al., "Body traffic: ecology, genetics, and immunity in inflammatory bowel disease", Annu Rev Pathol., Feb. 28, 2007, pp. 401-429, vol. 2.
Brichford, Can You Prevent Multiple Sclerosis? Understanding factors that increase your risk of multiple sclerosis and what—if anything—you can do about them. EverydayHealth.com. Dec. 2008; 2 pages.
Brubaker et al., Mitogenic activity of purified capsular polysaccharide A from Bacteroides fragilis: differential stimulatory effect on mouse and rat lymphocytes in vitro. J Immunol. Feb. 15, 1999; 162(4):2235-42.
Bruce D, et al. (2011) Converging pathways lead to overproduction of IL-17 in the absence of vitamin D signaling. International immunology 23: 519-528.
Brunkow, M.E., et al., "Disruption of a new forkhead/winged-helix protein, scurfin, results in the fatal lymphoproliferative disorder of the scurfy mouse" Nat Genet 27, 68-73 (2001).
Budinger et al., Immunologic mechanisms in hypersensitivity reactions to metal ions: an overview. Allergy. Feb. 2000;55(2):108-15. Review.
Burgers et al., The challenges of HIV vaccine development and testing. Best Pract Res Clin Obstet Gynaecol. Apr. 2005;19(2):277-91.
Byers et al., "Mechanism of action of vitamin D and the vitamin D receptor in colorectal cancer prevention and treatment," Rev. Endocr. Metab. Disord, Mar. 2012, pp. 31-38, vol. 13, Issue 1, Springer, Berlin, Germany.

(56) References Cited

OTHER PUBLICATIONS

Cabrera R, et al. (2010) Influence of serum and soluble CD25 (sCD25) on regulatory and effector T-cell function in hepatocellular carcinoma. Scandinavian journal of immunology 72: 293-301.
Campbell et al. The vitamin D receptor as a therapeutic target in Expert Opinion Ther. Targets, 2006; vol. 10; pp. 735-748.
Cantorna et al. "Vitamin D status, 1,25-dihydroxyvitamin D3, and the immune system" (Am. J. Clin. Nutr. 80(suppl):1717S-20S, 2004).
Cantorna MT, et al. (1996) "1,25-Dihydroxyvitamin D3 reversibly blocks the progression of relapsing encephalomyelitis, a model of multiple sclerosis". Proceedings of the National Academy of Sciences of the United States of America 93: 7861-7864.
Catorna, M.T et al. 1,25-Dihydroxycholecalciferol prevents and ameliorates symptoms of experimental murine inflammatory bowel disease. J. Nutr. 2000 130(11) oo.2648-52.
Cash, H.L., et al. (2006). Symbiotic bacteria direct expression of an intestinal bactericidal lectin. Science 313, 1126-1130.
Chambers E. et al. (2011) The impact of vitamin D on regulatory T cells. Curr. Allergy Asthma Rep 11: 29-36.
Chang JH, et al. (2010) "1,25-Dihydroxyvitamin D3 inhibits the differentiation and migration of T(H)17 cells to protect against experimental autoimmune encephalomyelitis." PLoS One 5: e12925. 12 pages.
Chatila et al., Role of regulatory T cells in human diseases. J Allergy Clin Immunol. Nov. 2005;116(5):949-59; quiz 960.
Chen et al., "Delivery of foreign antigens by engineered outer membrane vesicle vaccines", Proc Natl Acad Sci USA, Feb. 16, 2010, pp. 3099-3104, 107 (7), National Academy of Sciences.
Chen Jet al., DNA inversion on conjugative plasmid pVT745. J Bacteriol. Nov. 2002; 184(21):5926-34.
Chow J, et al. (2009) Getting the bugs out of the immune system: do bacterial microbiota "fix" intestinal T cell responses? Cell Host Microbe 5: 8-12.
Clemente et al., "Infliximab modifies mesenteric adipose tissue alterations and intestinal inflammation in rats with TNBS-induced colitis," Scand. J. Gastroenterol., vol. 47, 943-50 (2012).
Cobb et al., Zwitterionic capsular polysaccharides: the new MHCII-dependent antigens. Cell Microbial. Oct. 2005;7(10): 1398-403. Review.
Collison et al., The inhibitory cytokine IL-35 contributes to regulatory T-cell function. Nature. Nov. 22, 2007;450(7169):566-9.
Comstock et al. Analysis of a capsular polysaccharide biosynthesis locus of Bacteroides fragilis. (1999) Infect Immun 67:3525-32.
Comstock et al., Bacterial glycans: key mediators of diverse host immune responses. Cell. Sep. 8, 2006;126(5):847-50.
Comstock et al., Interstrain variation of the polysaccharide B biosynthesis locus of Bacteroides fragilis: characterization of the region from strain 638R. J Bacteriol. Oct. 1999 ;181(19):6192-6.
Conesa et al., Interleukin-2 induces peroxide production by primed normodense eosinophils of patients with asthma. Allergy Asthma Proc. Jan.-Feb. 2003;(1):27-33.
Coombes JL, et al. (2007) Control of intestinal homeostasis by regulatory T cells and dendritic cells. Semin Immunol 19: 116-126.
Coombes, JL., et al. (2007). A functionally specialized population of mucosal CD103+ DCs induces Foxp3+ regulatory T cells via a TGF-beta and retinoic acid-dependent mechanism. J Exp Med 204, 1757-1764.
Correale J, et al. (2011) Vitamin D-mediated immune regulation in multiple sclerosis. Journal of the neurological sciences 311: 23-31.
Couper et al. "IL-10: The Master Regulator of Immunity to Infection" Journal of Immunology. 2008; 180:5771-5777.
Coussens & Werb, "Inflammation and cancer," Nature, vol. 420, 860-867 (2002).
Coyne et al., "Polysaccharide biosynthesis locus required for virulence of Bacteroides fragilis", Infect. Immun., Jul. 2001, pp. 4342-4350, vol. 69, No. 7.
Coyne, M.J. et al., "Bacteroides fragilis NCTC9343 Produces at Least Three Distinct Capsular Polysaccharides: Cloning, Characterization, and Reassignment of Polysaccharide Band C Biosynthesis Loci", Infection and Immunity, Nov. 2000, p. 6176-6181.
Crabb et al., T cell regulation of Bacteroides fragilis-induced intraabdominal abscesses. Rev Infect Dis. Jan.-Feb. 1990;12 Suppl 2:S1 78-84. Review.
Craig, Autologous hematopoietic stem cell transplantation for Crohn's disease. Autoimmun Rev. Aug. 2002;1(4):244-9. Review.
Dadley-Moore, The sweet side of maturation. Nature Rev Immunol. sep. 2005;5:674.
Dahiyat BI. et al., De nova protein design: fully automated sequence selection. Science (1997) 278:82-87.
Daniel et al. Immune Modulatory Treatment of Trinitrobenzene Sulfonic Acid Colitis with Calcitriol is Associated with a Change of a T Helper (Th) 1/1Th17 to a Th2 and Regulatory T Cell Profile, in J. Pharmacology and Expet. Therapeutics, 2008, vol. 324, pp. 23-33.
Decision of Refusal dated Feb. 26, 2016 in Japanese Patent Application No. 2013-503958.
Decision of Refusal dated Nov. 27, 2018 in Japanese Patent Application No. 2016-513092.
Deib, Treating multiple sclerosis with monoclonal antibodies: a 2013 update. Expert Rev Neurother. Mar. 2013;13(3):313-35. doi: 10.1586/ern.13.17.
Denning, T et al. "Lamina propria macrophages and dendritic cells differentially induce regulatory and interleukin 17-producing T cell responses" Nature Immunology; vol. 8; No. 10; Oct. 1, 2007; pp. 1086-1094.
Deslongchamps et al., "Ozonolysis of Acetals. (1) Ester Synthesis, (2) THP Ether Cleavage, (3) Selective Oxidation of B-Glycoside, (4) Oxidative Removal of Benzylidene and Ethylidene Protecting Groups". Canadian J of Chem. 1971;49:2465-2467.
Deslongchamps et al., The Importance of Conformation in the Ozonolysis of Acetals. Canadian J Chem. 1972;50:3402-3404.
Deslongchamps et al., The Oxidation of Acetals by Ozone. Canadian J Chem. 1974;52:3651-3664.
Dias et al., Antisense oligonucleotides: Basic concepts and mechanisms. Mol. Cancer Therap., 2002, vol. 1:347-355.
Difabio et al., Structure of the Capsular Polysaccharide Antigen of Type IV Group B *Streptococcus*; Can. J. Chem. 67:877(1989).
Doig et al., The efficacy of the heat killing of *Mycobacterium tuberculosis*. J Clin Pathol. Oct. 2002;55(10):778-9.
European Communication pursuant to Article 94(3) EPC dated Feb. 5, 2014 for European application 10767863.3 filed on Apr. 23, 2010 in the name of California Institute of Technology. 7 pages.
European Communication pursuant to Rules 70(2) and 70a(2) EPC dated Dec. 27, 2010 for European application 08847489.5 filed on Nov. 9, 2008 in the name of California Institute of Technology. 7 pages.
European Communication pursuant to Rules 70(2) and 70a(2) EPC dated Feb. 12, 2013 for European application 10767863.3 filed on Apr. 23, 2010 in the name of California Institute of Technology. 1 page.
Extended European Search Report for European Application No. 10767863.3 dated Jan. 24, 2013. 10 pages.
European Search Report dated Jan. 30, 2015 for European application 10767863.3 filed on Apr. 23, 2010 in the name of California Institute of Technology. 5 pages.
Extended European Search Report for the European Application No. 11784368.0, dated Dec. 2, 2013, 13 pages.
Examination Report dated May 5, 2017 in European Patent Application No. 08847489.
Examination Report for European patent application No. 11784368.0, dated Jul. 8, 2016. 7 pages.
Examination Report dated Jan. 24, 2018 in European Patent Application No. 147952048.
Examination Report dated Jan. 18, 2019 in European Patent Application No. 147952048.
Examination Report dated Sep. 23, 2014 in European Patent Application No. 11766746.9.
Examination Report dated Nov. 10, 2015 in European Patent Application No. 11766746.9.
Extended European Search Report dated Sep. 13, 2013 in European Application No. 11766746.9.

(56) References Cited

OTHER PUBLICATIONS

Extended European Search Report dated Dec. 8, 2018 in European Application No. 08847489.
Extended European Search Report for Application No. 12811896.5, dated Jun. 1, 2015. 11 pages.
Extended European Search Report for European Application No. 12837738.9 dated Mar. 18, 2015 8 pages.
Extended European Search Report for European Application No. 14795204.8, dated Dec. 8, 2016, 9 pages.
Falk, P.G., et al. (1998). Creating and maintaining the gastrointestinal ecosystem: what we know and need to know from gnotobiology. Microbiol Mol Biol Rev 62, 1157-1170.
Final Office Action for U.S. Appl. No. 12/766,787, filed Apr. 23, 2010 on behalf of June L. Round et al. dated Aug. 4, 2015. 29 pages.
Final Office Action for U.S. Appl. No. 12/766,787, filed Apr. 23, 2010 on behalf of June L. Round et al. dated Nov. 26, 2012. 12 pages.
Final Office Action for U.S. Appl. No. 13/082,183, filed Apr. 7, 2011 on behalf of Yue Shen et al. dated Jan. 9, 2014. 9 pages.
Final Office Action for U.S. Appl. No. 13/112,725, filed May 20, 2011 on behalf of June L. Round, dated Jan. 7, 2015. 15 pages.
Final Office Action for U.S. Appl. No. 13/112,725, filed May 20, 2011 on behalf of June L. Round, dated Oct. 24, 2013. 8 pages.
Final Office Action for US Application No. U.S. Appl. No. 13/112,725, filed May 20, 2011 on behalf of California Institute of Technology, dated Nov. 2, 2016. 29 Pages.
Final Office Action for U.S. Appl. No. 13/360,702, filed Jan. 28, 2012 on behalf of Sarkis K. Mazmanian et al. dated Dec. 3, 2013. 14 pages.
Final Office Action for U.S. Appl. No. 13/573,695, filed Oct. 3, 2012 on behalf of Sarkis K. Mazmanian et al. dated Jan. 28, 2014. 12 pages.
Final Office Action dated Dec. 28, 2017 in U.S. Appl. No. 14/660,827.
Final Office Action dated Jun. 15, 2018 in U.S. Appl. No. 14/264,607.
Final Office Action dated Oct. 22, 2018 in U.S. Appl. No. 14/803,598.
Final Office Action dated Jun. 28, 2019 in U.S. Appl. No. 15/179,810.
Final Office Action dated Sep. 16, 2020 in U.S. Appl. No. 16/386,522.
Finberg et al., Decay-accelerating factor expression on either effector or target cells inhibits cytotoxicity by human natural killer cells. J Immunol. Sep. 15, 1992;149(6):2055-60.
Fink, et al. "Human antigen-presenting cells respond differently to gut-derived probiotic bacteria but mediate similar strain-dependent NK and T cell activation" FEMS Immunology and Medical Microbiology, 2007, vol. 51, No. 3; pp. 535-546.
Fontenot, J.D., et al. (2003). Foxp3 programs the development and function of CD4+CD251 + regulatory T cells. Nat Immunol 4, 330-336.
Fournier et al., Isolation of type 5 capsular polysaccharide from *Staphylococcus aureus*. Ann Inst Pasteur Microbial. Sep.-Oct. 1987;138(5):561-7.
Fridkis-Hareli et al., Binding motifs of copolymer 1 to multiple sclerosis- and rheumatoid arthritis-associated HLA-DR molecules. J Immunol. Apr. 15, 1999;162(8):4697-704.
Fridkis-Hareli et al., Binding of random copolymers of three amino acids to class 11 MHC molecules. Int Immunol. May 1999;11(5):635-41.
Fridkis-Hareli et al., Direct binding of myelin basic protein and synthetic copolymer 1 to class 11 major histocompatibility complex molecules on living antigen-presenting cells—specificity and promiscuity. Proc Natl Acad Sci USA. May 24, 1994;91(11):4872-6.
Fridkis-Hareli et al., Synthetic copolymer 1 and myelin basic protein do not require processing prior to binding to class 11 major histocompatibility complex molecules on living antigen-presenting cells. Cell Immunol. Jul. 1995;163(2):229-36.
Froicu, M et al. "A crucial role for the vitamin D receptor in experimental inflammatory bowel diseases" Mol. Endocrinol, 2003. 17(12) oo.2386-2392.
Froicu, M., et al. Vitamin D receptor is required to control gastrointestinal immunity in IL-10 knockout mice. Immunology, 2006. 117(3) p. 310-8.

Gallorini, et al., "Toll-like receptor 2 dependent immunogenicity of glycoconjugate vaccines containing chemically derived zwitterionic polysaccharides," PNAS vol. 106: 17481-17486.Oct. 13, 2009. 6 Pages.
Gally DL et al. Environmental regulation of the fim switch controlling type 1 fimbrial phase variation in *Escherichia coli* K-12: effects of temperature and media. (1993) J Bacteriol 175:6186-93.
Garrett et al., "Colitis-Associated Colorectal Cancer Driven by T-bet Deficiency in Dendritic Cells," Cancer Cell, vol. 16, 208-19 (2009).
Garrett et al., "Enterobacteriaceae Act in Concert with the Gut Microbiota to Induce Spontaneous and Maternally Transmitted Colitis," Cell Host Microbe, vol. 8, 292-300 (2010).
Gelu-Simeon, et al., Evaluation and predictive factors of thyroid disorder due to interferon alpha in the treatment of hepatitis C. World J Gastroenterol 2009; 15(3):328-333.
GenBank Accession No. AJ277832; Hutloff Jan. 19, 2001.
GenBank Accession No. CAC06612; Hutloff Jan. 19, 2001.
GenBank Accession No. NM012092; Dec. 20, 2003.
GenBank Accession No. NP036224; Dec. 20, 2003.
GIBSON 111 et al., The capsular polysaccharide complex of Bacteroides fragilis induces cytokine production from human and murine phagocytic cells. Infect Immun. Mar. 1996;64(3): pp. 1065-1069.
Gibson et al., "Chapter 5: trans-Galactooligosaccharides as Prebiotics". Handbook of Functional Dairy Products. Edited by Colette Shortt and John O'Brien. Published by CRC Press. 2004. 18 pages.
Glazebrook et al., A novel exopolysaccharide can function in place of the calcofluor-binding exopolysaccharide in nodulation of alfalfa by Rhizobium meliloti. Cell. Feb. 24, 1989;56(4):661-672.
Golgher et al., Galactofuranose-containing glycoconjugates of epimastigote and trypomastigote forms of Trypanosoma cruzi. Mol Biochem Parasitol. Aug. 1993;60(2):249-64.
Gondek, D.C., et al. (2005). Cutting edge: contact-mediated suppression by CD4+CD25+ regulatory cells involves a granzyme B-dependent, perforin-independent mechanism. J. Immunol.; vol. 174, 1783-1786.
Gonzalez-Hernandez et al., Peripheral blood CD161 + T cells from asthmatic patients are activated during asthma attack and predominantly produce IFN-gamma. Scand J Immunol. Apr. 2007;65(4):368-75.
Goverman J (2009) Autoimmune T cell responses in the central nervous system. Nat Rev Immunol 9: 393-407.
Goverman J, et al. (1993) Transgenic mice that express a myelin basic protein-specific T cell receptor develop spontaneous autoimmunity. Cell 72: 551-560.
Grabow, Bacteriophages: Update on application as models for viruses in water. Water SA 200;27(2):251-268.
Grivennikov et al., "IL-6 and Stat3 Are Required for Survival of Intestinal Epithelial Cells and Development of Colitis-Associated Cancer," Cancer Cell, vol. 15, 103-113 (2009).
Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.
Hall, J.A., et al. (2008). Commensal DNA limits regulatory T cell conversion and is a natural adjuvant of intestinal immune responses. Immunity 29, 637-649.
Hamelmann et al., Noninvasive measurement of airway responsiveness in allergic mice using barometric plethysmography. Am J Respir Crit Care Med. Sep. 1997;156(3 Pt 1):766-75.
Hampe, J., et al. (2001 ). Association between insertion mutation in NOD2 gene and Crohn's disease in German and British populations. Lancet 357. 1925-1928.
Hampe, J., et al. (2007). A genome-wide association scan of nonsynonymous SNPs identifies a susceptibility variant for Crohn disease in ATG 16L 1. Nat Genet 39, 207-211.
Haregewoin et al., Human gamma delta+ T cells respond to mycobacterial heat-shock protein.Nature. Jul. 27, 1989;340(6231 ):309-12.
Harrington L. et al., "Interleukin 17-producing CD4+ effector T cells develop via a lineage distinct from the T helper type 1 and 2 lineages" *Nature Immunology*, Nov. 2005, vol. 6, No. 11, pp. 1123-1132, 10 pages.

(56) References Cited

OTHER PUBLICATIONS

Harth et al. Treatment of *Mycobacterium* tuberculosis with antisense oligonucleotides to glutamine synthetase mRNA inhibits glutamine synthetase activity, formation of poly-L glutamate/glutamine cell wall structure, and bacterial replication. Proc Natl. Acad. Sci. 97: 418-423, 2000.
He, B., et al. (2007). Intestinal bacteria trigger T cell-independent immunoglobulin A(2) class switching by inducing epithelial-cell secretion of the cytokine April. Immunity 26, 812-826.
Hertl et al., T cell control in autoimmune bullous skin disorders. J Clin Investi. May 2006; 116( 5):1159-66. Review.
Hewison M, et al. (2003) Differential regulation of vitamin D receptor and its ligand in human monocyte-derived dendritic cells. J Immunol 170: 5382-5390.
Hirata et al., Cytokine synthesis of human monocytes stimulated by triple or single helical conformer of an antitumour (1->3)-beta-D-glucan preparation, sonifilan. Zentralbl Bakteriol. Nov. 1998;288(3):403-13.
Hodge et al., Allium sativum (garlic) suppresses leukocyte inflammatory cytokine production in vitro: potential therapeutic use in the treatment of inflammatory bowel disease. Cytometry. Aug. 1, 2002;48(4):209-15.
Hofstetter et al., Th17 Cells in MS and Experimental Autoimmune Encephalomyelitis. Int MS J. Apr. 2009;16(1):12-8.
Hooper, L.V. (2009). Do symbiotic bacteria subvert host immunity? Nat Rev Microbiol 7, 367-374.
Hooper, L.V. et al. (2001) Commensal host-bacterial relationships in the gut. Science 292, 1115-1118.
Hori, S. et al. "Control of regulatory T cell development by the transcription factor Foxp3" Science vol. 299, No. 5609 pp. 1057-1061 (2003).
Horstman et al., "Enterotoxigenic *Escherichia coli* secretes active heat-labile enterotoxin via outer membrane vesicles", J Bio Chem., Apr. 28, 2000, pp. 12489-12496, 275.
Hu et al., "Inflammation-induced tumorigenesis in the colon is regulated by caspase-1 and NLRC4," Proc. Natl. Acad. Sci., vol. 107, 21635-21640 (2010).
Huibregtse et al.., Immunopathogenesis of IBD: insufficient suppressor function in the gut? Gut. Apr. 2007;56(4):584-92. Epub Oct. 17, 2006.
Hutloff et al., ICOS is an inducible T-cell co-stimulator structurally and functionally related to CD28. Nature. Jan. 21, 1999;397(6716):263-6.
International Preliminary Report on Patentability for Application No. PCT/US2008/082928, dated May 11, 2010, 6 pages.
International Preliminary Report on Patentability for Application No. PCT/US2010/032300, dated Oct. 25, 2011, 6 pages.
International Preliminary Report on Patentability for Application No. PCT/US2012/023050, dated Jul. 30, 2013, 5 pages.
International Preliminary Report on Patentability for Application No. PCT/US2014/037392 dated Nov. 10, 2015.8 pages.
International Preliminary Report on Patentability for International Application No. PCT/US2016/037044 filed Jun. 10, 2016 on behalf of California Institute of Technology, dated Dec. 12, 2017. 9 pages (English Only).
International Search Report for International Application PCT/US2016/037044 filed Jun. 10, 2016 on behalf of California Institute of Technology, dated Sep. 22, 2016. 4 pages.
International Search Report and Written Opinion for Application No. PCT/US2011/037476, dated Aug. 26, 2011, 9 pages.
Isaksson et al., Conditional DC depletion does not affect priming of encephalitogenic Th cells in EAE. Eur J Immunol. Oct. 2012;42(10):2555-63. doi: 10.1002/eji.201142239. Epub Aug. 8, 2012.
Ishikawa, H et al., "Effect of intestinal microbiota on the induction of regulatory CD25 CD4+ T+ cells" Clin Exp Immunol 153, 127-135 (2008).
Itokazu et al., Abscess formation as a complication caused by postoperative osteomyelitis of the femur. Arch Orthop Trauma Surg. 1998;118(1-2):99-102. Review.
Itzkowitz & Harpaz, "Diagnosis and Management of Dysplasia in Patients With Inflammatory Bowel Diseases," Gastroenterology, vol. 126, 1634-1648 (2004).
Ivanov, 11 et al. "The Orphan Nuclear Receptor RORγt Directs the Differentiation Program of Proinflammatory IL-17+ T Helper Cells" Cell 126; 1121-1133 (2006).
Izcue, A., et al. (2009). Regulatory lymphocytes and intestinal inflammation. Annu Rev Immunol 27, 313-338.
Japanese Decision of Rejection dated Oct. 29, 2013 for Japanese application 2010-533311 filed on Apr. 23, 2010 in the name of California Institute of Technology.
Japanese Notice for Reasons for Rejection dated Mar. 24, 2015 for Japanese application 2014-038746 filed on Nov. 9, 2008 in the name of California Institute of Technology.
Japanese Notification of Reasons for Refusal dated Feb. 12, 2014 for Japanese application 2012-507451 filed on Apr. 23, 2010 in the name of California Institute of Technology.
Japanese Official Decision of Refusal dated Feb. 10, 2015 for Japanese application 2012-507451 filed on Apr. 23, 2010 in the name of California Institute of Technology.
Jawad et al., "Inflammatory Bowel Disease and Colon Cancer," Recent Results Cancer Rec., vol. 185, 99-115 (2011).
Jeffery LE, et al. (2009) 1,25-Dihydroxyvitamin D3 and IL-2 combine to inhibit T cell production of inflammatory cytokines and promote development of regulatory T cells expressing CTLA-4 and FoxP3. J Immunol 183: 5458-5467.
Jennings et al., Immunochemistry of groups A, B, and C meningococcal polysaccharide-tetanus toxoid conjugates. J Immunol. Sep. 1981;127(3): 1011-8.
Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.
Jia et al., Gut microbiota: a potential new territory for drug targeting. Nat Rev Drug Discov. Feb. 2008;7(2):123-9. doi: 10.1038/nrd2505.
Johnson et al., Bacterial capsular polysaccharide prevents the onset of asthma through T-cell activation. Glycobiology. Apr. 2015;25(4):368-75. doi: 10.1093/glycob/cwul 17. Epub Oct. 27, 2014.
Jonuleit et al., Identification and functional characterization of human CD4(+)CD25(+) T cells with regulatory properties isolated from peripheral blood. J Exp Med. Jun. 4, 2001 ;193(11):1285-94.
Jonuleit et al., The regulatory T cell family: distinct subsets and their interrelations. J Immunol. Dec. 15, 2003;171(12):6323-7.
Joshi S, et al. (2011) 1,25-dihydroxyvitamin 0(3) ameliorates Th17 autoimmunity via transcriptional modulation of interleukin-17A. Molecular and cellular biology 31: 3653-3669.
Jotwani et al., Pathogenicity of Bacteroides fragilis group in rat intra-abdominal abscesses. Microbial Immunol. 1992;36(10):1041-9.
Kakalacheva K, et al. (2011) Environmental triggers of multiple sclerosis. FEBS letters 585: 3724-3729.
Kakalacheva K, et al. (2011) Viral triggers of multiple sclerosis. Biochimica et biophysica acta 1812: 132-140.
Kalka-Moll et al., "Effect of Molecular Size on the Ability of Zwitterionic Polysaccharides to Stimulate Cellular Immunity," J. Immunol., vol. 164, 719-24 (2000).
Kalka-Moll et al., Bacteriodes Fragilis NCTC 9343 Capsular Polysaccharide PS A and the Effect of Chain Length of T cell Proliferation. Abstracts of the 98th Gen Mtg of the American Soc for Microbial. 1998;98:123. Abstract B-405.
Kalka-Moll et al., Immunochemical and biological characterization of three capsular polysaccharides from a single Bacteroides fragilis strain. Infect Immun. Apr. 2001;69(4):2339-44.
Kasper et al., Capsular polysaccharides and lipopolysaccharides from two Bacteroides fragilis reference strains: chemical and immunochemical characterization. J Bacterial. Feb. 1983;153(2):991-7.
Kasper et al., Protective efficacy of immunization with capsular antigen against experimental infection with Bacteroides fragilis. J Infect Dis. Nov. 1979;140(5):724-3 I.
Kasper et al., Surface antigens as virulence factors in infection with Bacteroides fragilis. Rev Infect Dis. Mar.-Apr. 1979;1(2):278-90.

(56) References Cited

OTHER PUBLICATIONS

Kasper et al., The polysaccharide capsule of Bacteroides fragilis subspecies fragilis: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kayama H. et al., "Regulation of intestinal homeostasis by innate and adaptive immunity" International Immunology, vol. 24, No. 11, pp. 673-680,Sep. 2012, 8 pages.
Kennedy et al., Prevention of experimental postoperative peritoneal adhesions by N,0-carboxymethyl chitosan. Surgery. Nov. 1996;120(5):866-70.
Kernodle et al. Expression of an antisense hla fragment in *Staphylococcus aureus* reduces alpha-toxin production in vitro and attenuates lethal activity in a murine model. Infection and Immunity 179-184. 1997.
Kesty et al., "Incorporation of heterologous outer membrane and periplasmic proteins into *Escherichia coli* outer membrane vesicles", J Bio Chem., Jan. 16, 2004, pp. 2069-2076, 279.
Kim, J.M., et al. (2007). Regulatory T cells prevent catastrophic autoimmunity throughout the lifespan of mice. Nat Immunol 6, 191-197.
Kinoshita et al., Retinoic acid reduces autoimmune renal injury and increases survival in NZB/W FI mice. J Immunol. Jun. 1, 2003;170(11):5793-8.
Knetsch et al., Polymers with tunable toxicity: a reference scale for cytotoxicity testing of biomaterial surfaces. J Biomed Mater Res A. Sep. 15, 2007;82(4):947-57.
Knirel et al., Somatic antigens of Pseudomonas aeruginosa. The structure of 0-specific polysaccharide chains of lipopolysaccharides of P. aeruginosa 03 (Lanyi), 025 (Wokatsch) and Fisher immunotypes 3 and 7. Eur J Biochem. Sep. 15, 1987;167(3):549-61.
Knirel et al., The structure of O-specific polysaccharides and serological classification of Pseudomonas aeruginosa (a review). Acta Microbial Hung. 1988;35(1):3-24. Review.
Koch, M.A., et al. (2009). The transcription factor T-bet controls regulatory T cell homeostasis and function during type 1 inflammation. Nat Immunol 10, 595-602.
Kong, J., et al., Novel role of the vitamin D receptor in maintaining the integrity of the intestinal mucosal barrier. Am J Physiol Gastrointest Liver Physiol, 2008. 294(1): p. G208-16.
Krause et al., An Inhibitor of Cell Proliferation Associated with Adhesion Formation Is Suppressed by N,0-Carboxymethyl Chitosan. J Investi Surg. 1988;11:105-113.
Krutzik SR, et al. (2008) "IL-15 links TLR2/1-induced macrophage differentiation to the vitamin D-dependent antimicrobial pathway". J Immunol 181: 7115-7120.
Kuehn, M.J et al. "Bacterial outer membrane vesicles and the host-pathogen interaction" Genes and Development vol. 19, No. 22 pp. 2645-2655 (2005).
Kulicke et al., Correlation between immunological activity, molar mass, and molecular structure of different (1->3)-beta-D-glucans. Carbohydr Res. Jan. 2, 1997;297(2):135-43.
Kuper et al., "Infections as a major preventable cause of human cancer," J. Intern. Med., vol. 248, 171-183 (2000).
Kurup et al., Antibody response to low-molecular-weight antigens of Aspergillus fumigatus in allergic bronchopulmonary aspergillosis. J Clin Microbial. Jun. 1989;27(6):1312-6.
Lagishetty, V. et al. "Vitamin D deficiency in mice impairs colonic antibacterial activity and predisposes to colitis." Endocrinology.; Jun. 2010; vol. 151(6) pp. 2423-2432.
Lee et al., "Bacterial colonization factors control specificity and stability of the gut microbiota," Nature, vol. 501, 426-429 (2013).
Lee et al., Effects of In Vitro and In Vivo and Growth Conditions on Expression of Type 8 Capsular Polysaccharide by *Staphylococcus aureus*, Infection and Immunity, 61: 1853-1858, 1993.
Lee S.A., et al., "Plasma Interleukin-1beta, -6, -8 and Tumor Necrosis Factor-alpha as Highly Informative Markers of Pelvic Inflammatory Disease," Clinical Chemistry and Laboratory Medicine, Jul. 2008, vol. 46 (7), 3 pages.

Lee YK, et al. (2010) Has the microbiota played a critical role in the evolution of the adaptive immune system? Science 330: 1768-1773.
Lee YK, et al. (2011) Proinflammatory T-cell responses to gut microbiota promote experimental autoimmune encephalomyelitis. Proc Natl Acad Sci U S A 108 Suppl 1: 4615-4622.
Ley et al., Evolution of mammals and their gut microbes. Science. Jun. 20, 2008;320(5883): 1647-51. doi: 10.1 126/science. 1155725. Epub May 22, 2008.
Lindberg et al., Virulence factors in infections with *Bacteroides fragilis*: isolation and characterization of capsular polysaccharide and lipopolysaccharide. Scand J Infect Dis Suppl. 1982;35:45-52.
Liu et al., "Toll-like receptor 2 signaling modulates the functions of CD4+ CD25+ regulatory T cells", Proc. Natl. Acad. Sci. USA, May 2, 2006, pp. 7048-7053, vol. 103 No. 18.
Liu, N. et al. "Altered endocrine and autocrine metabolism of vitamin D in a mouse model of gastrointestinal inflammation." Endocrinology, 2008; 149(10): pp. 4799-4808.
Liu et al., "Glucuronoxylomannan promotes the generation of antigen-specific T regulatory cell that suppresses the antigen-specific Th2 response upon activation,", J. Cell. Mol. Med. vol. 13: 1765-1774.0nline Nov. 2008. 10 Pages.
Lysnyansky et al. Juxtaposition of an active promoter to via genes via site-specific DNA inversions generates antigenic variation in Mycoplasma bovis. (2001) J Bacteriol 183:5698-5708.
Macpherson et al., IgA responses in the intestinal mucosa against pathogenic and nonpathogenic microorganisms. Microbes Infect. Oct. 2001;3(12):1021-35.
Macpherson et al., Interactions between commensal intestinal bacteria and the immune system. Nat Rev Immunol. Jun. 2004;4(6):478-85.
Macpherson et al., Mucosal antibodies in inflammatory bowel disease are directed against intestinal bacteria. Gut. Mar. 1996;38(3):365-75.
Macpherson, A.J .et al. (2004). Induction of protective IgA by intestinal dendritic cells carrying commensal bacteria. Science 303, 1662-1665.
Maier, B.R., et al. (1972). Experimental Shigella infections in laboratory animals. I. Antagonism by human normal flora components in gnotobiotic mice. Infect Immun 6, 168-173.
Makela et al., IL-10 is necessary for the expression of airway hyperresponsiveness but not pulmonary inflammation after allergic sensitization. Proc Natl Acad Sci USA. May 23, 2000;97(11):6007-12.
Mamessier et al., "Cytokines in atopic diseases: revisiting the Th2 dogma" Eur J Dermatol. Mar.-Apr. 2006; 16(2):pp. 103-113.
Mantovani et al., "Cancer-related inflammation," Nature, vol. 454, 436-444 (2008).
Maynard CL, et al. (2009) Contrasting roles for all-trans retinoic acid in TGF-beta-mediated induction of Foxp3 and IL10 genes in developing regulatory T cells. The Journal of experimental medicine 206:343-357.
Maynard, C.L., et al. (2007). Regulatory T cells expressing interleukin 10 develop from Foxp3+ and Foxp3-precursor cells in the absence of interleukin 10. Nat Immunol 8, 931941.
Mayne CG, et al. (2011) "1,25-Dihydroxyvitamin D3 acts directly on the T lymphocyte vitamin D receptor to inhibit experimental autoimmune encephalomyelitis". European journal of immunology 41:822-832.
Mazmanian et al., Capsular polysaccharides of symbiotic bacteria modulate immune responses during experimental colitis. J Pediatr Gastroenterol Nutr. Apr. 2008;46 Suppl 1:E11-2. doi: 10.1097/01. mpg.0000313824.70971.a7.
Mazmanian, S.K. Host-bacterial symbiosis prevents intestinal inflammatory disease. California Institute of Technology. Amgen (Jul. 2008).
McClain et al. Inversion-independent phase variation of type 1 fimbriae in *Escherichia coli*. (1993) J Bacteriol 175(14):4335-44.
McMurchy A.N., et al. (2012) Suppression assays with human T regulatory cells: a technical guide. European journal of immunology 42: 27-34.
Meisel-Mikolajczyk et al., Human T cell adhesion to endothelium stimulated by membrane components extracted from strains of

(56) References Cited

OTHER PUBLICATIONS

*Bacteroides vulgatus* (member of *B. fragilis* group). Arch Immunol Ther Exp (Warsz). 1993;41 (2):129-31.
Meltzer, et al., "Pneumococcal Polysaccharides Interact with Human Dendritic Cell,". Infect. Immun. vol. 74: 1890-1895. Mar. 2006. 7 Pages.
Mertens, J., et al., *Streptococcus pneumoniae* Serotype 1 Capsular Polysaccharide Induces CD8+CD28-Regulatory T Lymphocytes by TCR Crosslinking, PLOS Pathoqens, (Sep. 2009) vol. 5, Issue 9, e1000596, p. 1-15.
Miller et al., Severe asthma and the omalizumab option. Clinical and Molecular Allergy 2008, 6:4.
Min, B., et al. (2007). Gut flora antigens are not important in the maintenance of regulatory T cell heterogeneity and homeostasis. Eur. J. Immunol. 37; pp. 1816-1923.
Mojtabavi et al., Long-lived Th2 memory in experimental allergic asthma. J Immunol. Nov. 1, 2002; 169(9):4 788-96.
Montz et al., Interleukin 10: ability to minimize postoperative intraperitoneal adhesion formation in a murine model. Fertil Steril. Jun. 1994;61(6):1136-40.
Moore, The List Goes on, New Additions to the Autoimmune Disease Raster. http://autoimmunedisease.suiteIOI.com/blog.cfm/ the list goes on. pp. 1-3. Aug. 7, 2007.
Moorman et al., National Surveillance of Asthma: United States, 2001-2010. National Center for Health Statistics. Vital Health Stat. 2012;3(35) 67 pages.
Mor et al., Identification of aldolase as a target antigen in Alzheimer's disease. J Immunol. Sep. 1, 2005;175(5):3439-45.
Mora et al., Generation of gut-homing IgA-secreting B cells by intestinal dendritic cells. Science. Nov. 17, 2006;314(5802):1157-60.
Mora et al., Selective imprinting of gut-homing T cells by Peyer's patch dendritic cells. Nature. Jul. 3, 2003;424(6944):88-93.
Morales-Tirado V, et al. (2011) 1alpha,25-dihydroxyvitamin D3 (vitamin D3) catalyzes suppressive activity on human natural regulatory T cells, uniguely modulates cell cycle progression, and augments FOXP3. Clinical immunology 138: 212-221.
Mulholland et al., Strategies for the control of pneumococcal diseases. Vaccine. Jul. 30, 1999;17 Suppl I:S79-84. Review.
Nagaraj S. et al., "Reciprocal Relationship between Myeloid-Derived Suppressor Cells and T Cells" *Journal of Immunology*, Dec. 2013, pp. 17-23 8 pages.
Nakayama-Imaohji, H. et al. "Identification of the site-specific DNA invertase responsible for the phase variation of SusC/SusD family outer membrane proteins in Bacteroides fragilis" J. Bacterial.; 2009; vol. 191; No. 19; pp. 6003-6011.
Natori et al., Agelasphins, novel antitumor and immunostimulatory cerebrosides from the marine sponge Agelas mauritianus. Tetrahedron. 1994;50(9):2771-2784.
NCBI Sequence View "Toxin" [*Salmonella typhimurium* LT2]. Retrieved Aug. 16, 2007 from http://www.ncbi.nim.nih.oov/entrez/ viewer.fcoi?db=protein&id= 17233414, pp. 1-2.
Nielsen et al., Applications of peptide nucleic acids. CurrOpin Biotechnol. Feb. 1999;10(1):71-5. Review.
No Author Listed, Acute Respiratory Disease Syndrome: What is acute respiratory disease syndrome? American Lung Association. 3 pages. http://www.lungusa.org/site/apps/nlnet/content3.aspz?c= dvLUK900E&b=2058817&content. Sep. 24, 2008.
No Author Listed, Excerpts from Immunobiology, in ed.. "Chapter 9. pp. 335-361; Chapter 1. pp. 2-9; Chapter 15. pp. 622-631" 2008.
No Author Listed, Lupus study. Meet A Lupus Researcher. www. lupusstudy.org/updates.php. Nov. 2005;!-2.
No Author Listed, Polyethylene Glycols (PEGs). Accessed Mar. 7, 05. 1 page. http://www.mindfully.org/Plastic/Polymers/Polyethylene-Glycols-PEGs.htm.
No Author Listed, The Merck Index. Eleventh Edition 1989:734-735.
No Author Listed, VAXA, Systemic lupus erythematosus (SLE), damaging and unpredictable. http://www.vaxa.com/arthritis-systemic-lupus-erythematosus.cfm. 1 page. Accessed Apr. 3, 2008.
Non-Final Office Action for U.S. Appl. No. 12/766,787, filed Apr. 23, 2010 on behalf of June L. Round et al. dated Jan. 20, 2015. 18 pages.
Non-Final Office Action for U.S. Appl. No. 12/766,787, filed Apr. 23, 2010 on behalf of June L. Round et al. dated May 8, 2012. 9 pages.
Non-Final Office Action for U.S. Appl. No. 12/766,787, filed Apr. 23, 2010 on behalf of June L. Round et al. dated Sep. 30, 2013. 19 pages.
Non-Final Office Action for U.S. Appl. No. 12/831,131, filed Jul. 6, 2010 on behalf of June L. Round et al. dated Aug. 26, 2014. 20 pages.
Non-Final Office Action for U.S. Appl. No. 13/082,183, filed Apr. 7, 2011 on behalf of Yue Shen et al. dated Aug. 13, 2013. 7 pages.
Non-Final Office Action for U.S. Appl. No. 13/082,183, filed Apr. 7, 2011 on behalf of Yue Shen et al. dated Jan. 20, 2015. 7 pages.
Non-Final Office Action for U.S. Appl. No. 13/112,725, filed May 20, 2011 on behalf of June L. Round, dated Mar. 18, 2016. 11 pages.
Non-Final Office Action for U.S. Appl. No. 13/112,725, filed May 20, 2011 on behalf of June L. Round, dated May 30, 2013. 7 pages.
Non-Final Office Action for U.S. Appl. No. 13/112,725, filed May 20, 2011 on behalf of June L. Round, dated May 8, 2014. 12 pages.
Non-Final Office Action for U.S. Appl. No. 13/360,702, filed Jan. 28, 2012 on behalf of Sarkis K. Mazmanian et al. dated Mar. 11, 2015. 13 pages.
Non-Final Office Action for U.S. Appl. No. 13/360,702, filed Jan. 28, 2012 on behalf of Sarkis K. Mazmanian et al. dated Mar. 18, 2013. 13 pages.
Non-Final Office Action for U.S. Appl. No. 13/573,695, filed Oct. 3, 2012 on behalf of Sarkis K. Mazmanian et al. dated Aug. 28, 2013. 11 pages.
Non-Final Office Action for U.S. Appl. No. 14/015,769, filed Aug. 30, 2013 on behalf of Sarkis K. Mazmanian et al. dated Dec. 31, 2014. 7 pages.
Non-Final Office Action dated Aug. 9, 2017 in U.S. Appl. No. 14/264,607.
Non-Final Office Action dated Jan. 18, 2019 in U.S. Appl. No. 14/264,607.
Non-Final Office Action dated Mar. 16, 2017 in U.S. Appl. No. 14/631,760.
Non-Final Office Action dated Mar. 22, 2017 in U.S. Appl. No. 14/660,827.
Non-Final Office Action dated Dec. 27, 2018 in U.S. Appl. No. 14/660,827.
Non-Final Office Action dated May 11, 2018 in U.S. Appl. No. 14/803,598.
Non-Final Office Action for U.S. Appl. No. 15/011,151, filed Jan. 29, 2016 on behalf of California Institute of Technology dated Aug. 30, 2017 20 pages.
Non-Final Office Action dated Sep. 28, 2018 in U.S. Appl. No. 15/179,810.
Non-Final Office Action dated Oct. 14, 2020 in U.S. Appl. No. 15/179,810.
Non-Final Office Action dated Mar. 5, 2019 in U.S. Appl. No. 15/706,604.
Non-Final Office Action dated Nov. 17, 2019 in U.S. Appl. No. 16,514,796.
Non-Final Office Action dated Jun. 8, 2020 in U.S. Appl. No. 16/386,522.
Non-Final Office Action dated Sep. 1, 2020 in U.S. Appl. No. 16/562,358.
Norman; "Thyroiditis-Inflammation of the thyroid gland"; Endocrineweb 2009; www.endocrineweb.com/throiditis.html, 1-4. Downloaded Jul. 28, 2009.
Notice of Allowance for U.S. Appl. No. 13/573,695, filed Oct. 3, 2012 on behalf of Sarkis K. Mazmanian et al. dated Feb. 13, 2015. 9 pages.
Notice of Allowance for U.S. Appl. No. 13/573,695, dated May 15, 2015, 2 pages.
Notice of Allowance dated May 1, 2020 in U.S. Appl. No. 16/514,796.
Notice of Allowance dated Jul. 7, 2018 in European Patent Application No. 11766746.9.

(56) References Cited

OTHER PUBLICATIONS

Notice of Allowance dated Sep. 16, 2016 in Japanese Patent Application No. 2013-503958.
Notice of Allowance dated Jan. 9, 2018 in Japanese Patent Application No. 2016-126806.
Notice of Allowance dated Feb. 10, 2020 in Japanese Patent Application No. 2018-020819.
Notice of Reasons for Refusal dated Apr. 25, 2017 in Japanese Patent Application No. 2016-126806.
Notice of Reasons for Refusal dated Dec. 14, 2018 in Japanese Patent Application No. 2018-020819.
Notice of Reasons for Refusal dated Oct. 10, 2019 in Japanese Patent Application No. 2018-020819.
Notice of Reasons for Refusal dated Mar. 23, 2015 in Japanese Patent Application No. 2013-503958.
Notice of Reasons for Refusal dated Dec. 28, 2017 in Japanese Patent Application No. 2016-513092.
Notice of Reasons for Refusal dated Mar. 18, 2020 in Japanese Patent Application No. 2019-061261.
Notification of Reason for Refusal for Japanese Patent Application No. 2013-511406, dated Apr. 12, 2016. 7 pages (Japanese original + English translation).
Notification of Reasons for Refusal for Japanese Patent Application No. 2013-511406, dated May 12, 2015. 6 pages (Japanese original+ English translation).
Noverr MC, et al. (2004) Does the microbiota regulate immune responses outside the gut? Trends Microbiol 12: 562-568.
Nylander A, et al. (2012) "Multiple sclerosis". The Journal of Clinical Investigation; vol. 122; DO. 1180-1188.
Ochoa-Reparaz J, et al. (2009) Role of gut commensal microflora in the development of experimental autoimmune encephalomyelitis. J Immunol 183: 6041-6050.
Ochoa-Reparaz J, et al. (2010) A polysaccharide from the human commensal Bacteroides fragilis protects against CNS demyelinating disease. Mucosal Immunol 3: 487-495.
Ochoa-Reparaz J, et al. (2010) Central nervous system demyelinating disease protection by the human commensal Bacteroides fragilis depends on polysaccharide A expression. J Immunol 185: 4101-4108.
Ochoa-Reparaz, J. et al. "The role of subcellular fractions of commensal *Bacteroides fragilis* in the control of experimental autoimmune encephalomyelitis" Multiple Sclerosis; Sep. 2009; vol. 15; (Abstract Only).
O'Connor et al., Translational mini-review series on Th17 cells: CD4 T helper cells: functional plasticity and differential sensitivity to regulatory T cell-mediated regulation. Clin Exp Immunol. Feb. 2010;I59(2):137-47. doi: 10.1111/j.1365-2249.2009.04040.x. Epub Nov. 11, 2009.
Oda et al., A comprehensive map of the toll-like receptor signaling network. Mol Syst Biol. 2006;2:2006.0015. Epub Apr. 18, 2006.
Office Action for Japanese patent application No. JP2015-116494, dated Jul. 12, 2016. 8 pages (Japanese original + English translation).
Oh et al., CD4 T-helper cells engineered to produce IL-10 prevent allergen-induced airway hyperreactivity and inflammation. J Allergy Clin Immunol. Sep. 2002;110(3):460-8.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1->3)-beta-D-glucans in mice. Biol Pharm Bull. Jan. 1995;18(1):126-33.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk, A. et al., Evidence for T Cell-dependent Immunity to Bacteroides fragilis in an Intraabdominal Abscess Model; J. Clin Investi. 69:9-16 (1982).

Ozenci et al., Multiple sclerosis: levels of interleukin-10-secreting blood mononuclear cells are low in untreated patients but augmented during interferon-beta-1 b treatment. Scand J Immunol. May 1999;49(5):554-61.
Palmer MT, et al. (2011) Lineage-specific effects of 1,25-dihydroxyvitamin D(3) on the development of effector CD4 T cells. The Journal of biological chemistry 286: 997-1004.
Pantosti et al., Bacteroides fragilis strains express multiple capsular polysaccharides. J Clin Microbial. Jul. 1993;31(7):1850-5.
Paoletti et al., Effects of chain length on the immunogenicity in rabbits of group B *Streptococcus* type 111 oligosaccharide-tetanus toxoid conjugates. J Clin Investi. Jan. 1992;89(1):203-9.
Paole I 11 et al., Neonatal Mouse Protection against Infection with Multiple Group B Streptococcal (GBS) Serotypes by Maternal Immunization with a Tetravalent GBS Polysaccharide-Tetanus Toxoid Conjugate Vaccine, Infection and Immunity, 62:3236-3243, 1994.
Park et al., Interleukin-2 and soluble interleukin-2 receptor in bronchoalveolar lavage fluid from patients with bronchial asthma. Chest. Aug. 1994;106(2):400-6.
Patrick et al. "Mutational analysis of genes implicated in LPS and capsular polysaccharide biosynthesis in the opportunistic pathogen Bacteroides fragilis" Microbiology. Apr. 2009;155(Pt 4):1039-49.
Patrick et al., "A comparison of the haemagglutinating and enzymic activities of Bacteroides fragilis whole cells and outer membrane vesicles", Apr. 1996, pp. 191-202, vol. 20, Issue 4, Elsevier, Amsterdam, Netherlands.
Patrick et al., "Separation of capsulate and non-capsulate Bacteriodes fragilis on a discontinuous density gradient", J Med Microbial. , 1983, pp. 239-241, 16(2), The Pathological Society of Great Britain and Ireland, London, United Kingdom.
Pavliak et al., Structural elucidation of the capsular polysaccharide of Bacteroides fragilis strain 23745MI. Carbohydr Res. Oct. 2, 1995;275(2):333-41.
PCT Application No. PCT/US2011/031606 Search Report and Written Opinion dated Dec. 15, 2011.
PCT International Search Report and Written Opinion for International Patent Application No. PCT/US2012/023050, dated May 21, 2012. 7 pages.
PCT International Search Report and Written Opinion for PCT Application No. PCT/US2014/037392 filed May 8, 2014 on behalf of California Institute of Technology, dated Sep. 19, 2014. 28 pages.
PCT International Search Report for PCT/US2010/032300 filed Apr. 23, 2010 on behalf of California Institute of Technology et al. dated Jan. 31, 2011. 5 pages.
PCT Written Opinion for PCT/US2010/032300 filed Apr. 23, 2010 on behalf of California Institute of Technology et al. dated Jan. 31, 2011. 5 pages.
Pedersen LB, et al. (2007) 1,25-dihydroxyvitamin D3 reverses experimental autoimmune encephalomyelitis by inhibiting chemokine synthesis and monocyte trafficking. J Neurosci Res 85: 2480-2490.
Perumal et al., Protective effect of interleukin-2 on experimental intra-abdominal abscess development due to Bacteriodes Fragilis. Clinical Research. 1990;38(2):550A.
Pierrot-Deseilligny C, et al. Is hypovitaminosis Done of the environmental risk factors for multiple sclerosis? Brain; 2010; 133: 1869-1888.
Pillay J. et al., "Immune suppression by neutrophils and granulocytic myeloid-derived suppressor cells: similarities and differences" Cellular and Molecular Life Sciences, Feb. 2013, pp. 3813-3827 15 pages.
Popivanova et al., "Blocking TNF-a in mice reduces colorectal carcinogenesis associated with chronic colitis," J. Clin. Invest., vol. 118, 560-570 (2008).
Popovic et al., Inhibition of autoimmune encephalomyelitis by a tetracycline. Ann Neural. Feb. 2002;51(2):215-23.
Power C, et al. (2010) The human microbiome in multiple sclerosis: pathogenic or protective constituents? The Canadian journal of neurological sciences Le journal canadien des sciences neurologiques 37 Suppl 2: S24-33.
Pragani & Seeberger, "Total Synthesis of the *Bacteroides fragilis* Zwitterionic Polysaccharide A 1 Repeating Unit," JACS 2011, 133, 102-107.

(56) References Cited

OTHER PUBLICATIONS

Prieto et al., A new ganglioside in human meconium detected by antiserum against the human milk sialyloligosaccharide, LS-tetrasaccharide b, Archives of Biochemistry and Biophysics, 241:281-289, 1985.
Prucha et al., "Presence of Hypogammaglobulinemia—A Risk Factor of Mortality in Patients with Severe Sepsis, Septic Shock, and SIRS," Prague Medical Report 2013, 114(4), 246-257.
Rabe et al., Pharmacological treatment of asthma today. Eur Respir J Suppl. 2001 ;34:34s-40s.
Raetz et al., Lipopolysaccharide endotoxins. Annu Rev Biochem. 2002;71 :635-700. Epub Nov. 9, 2001.
Raghuwanshi, A. et al. "Vitamin D and Multiple Sclerosis" Journal of Cellular Biochemistry; 2008; vol. 105; pp. 338-343.
Raman et al. Vitamin D and gastrointestinal diseases: inflammatory bowel disease and colorectal cancer in Ther Adv. Gastroenterology, Jan. 10, 2011 (Jan. 10, 2011) vol. 4, pp. 49-62.
Ranua et al., Serum IgA, IgG, and IgM concentrations in patients with epilepsy and matched controls: a cohort-based cross-sectional study. Epilepsy Behav. Mar. 2005;6(2):191-5.
Reid, R.R., et al., "Endotoxin shock in antibody-deficient mice: unraveling the role of natural antibody and complement in the clearance of lipopolysaccharide," *Journal of immunology*, 1997. 159(2): p. 970-5. Abstract Only.
Rescigno, M. et al., "Dendritic cells express tight junction proteins and penetrate gut epithelial monolayers to sample bacteria" Nat Immunol 2, 361 (2001).
Restriction Requirement for U.S. Appl. No. 12/766,787, filed Apr. 23, 2010 on behalf of June L. Round et al. dated Mar. 15, 2012. 9 pages.
Restriction Requirement for U.S. Appl. No. 13/082,183, filed Apr. 7, 2011 on behalf of Yue Shen et al. dated May 31, 2013. 7 pages.
Restriction Requirement for U.S. Appl. No. 13/112,725, filed May 20, 2011 on behalf of June L. Round, dated Mar. 18, 2013. 7 pages.
Restriction Requirement for U.S. Appl. No. 13/360,702, filed Jan. 28, 2012 on behalf of Sarkis K. Mazmanian et al. dated Feb. 1, 2013. 6 pages.
Restriction Requirement for U.S. Appl. No. 13/573,695, filed Oct. 3, 2012 on behalf of Sarkis K. Mazmanian et al. dated May 23, 2013. 9 pages.
Restriction Requirement for U.S. Appl. No. 14/755,327, filed Jun. 30, 2015 on behalf of Sarkis K. Mazmanian et al. dated Aug. 11, 2016. 8 pages.
Restriction Requirement dated Aug. 18, 2014 in U.S. Appl. No. 14/015,769.
Restriction Requirement dated Jan. 26, 2015 in U.S. Appl. No. 14/274,607.
Restriction Requirement for U.S. Appl. No. 14/803,598, filed Jul. 20, 2015 on behalf of California Institute of Technology dated Feb. 14, 2018. 7 pages.
Restriction Requirement for U.S. Appl. No. 15/499,805, filed Apr. 27, 2017 on behalf of California Institute of Technology dated May 3, 2019 7 pages.
Restriction Requirement dated May 4, 2018 in U.S. Appl. No. 15/178,810.
Riesenfeld et al., Biosynthesis of heparin. Assay and properties of the microsomal N-acetyl-Dglucosaminyl N-deacetylase. J Biol Chem. Feb. 10, 1980;255(3):922-8.
Rodgers et al., "Prescribing an antibiotic? Pair it with probiotics", The Journal of Family Practice, Mar. 2013, pp. 148-150, vol. 62, No. 3.
Roncarolo et al., Type IT regulatory cells. Immunol Rev. Aug. 2001;182:68-79. Review.
Round et al., "Inducible Foxp3+ regulatory T cell development by a commensal bacterium of the intestinal microbiota", PNAS, Jul. 6, 2010, pp. 12204-12209, vol. 107 No. 27.
Round JL, et al. (2009) Coordination of tolerogenic immune responses by the commensal microbiota. J Autoimmun.
Round JL, et al. (2011) The Toll-like receptor 2 pathway establishes colonization by a commensal of the human microbiota. Science 332: 974-977.
Runia TF, et al. (2012) Lower serum vitamin D levels are associated with a higher relapse risk in multiple sclerosis. Neurology 79: 261-266.
Rypens et al., Percutaneous drainage of abdominal abscesses in pediatric Crohn's disease. AJR Am J Roentgenol. Feb. 2007;188(2):579-85.
Sakaguchi S, et al. (2008) Regulatory T cells and immune tolerance. Cell 133: 775-787.
Sakaguchi, S et al. (2006) Foxp3+ CD25+ CD4+ natural regulatory T cells in dominant self-tolerance and autoimmune disease. Immunol. Rev. 212, pp. 8-27.
Salyers et al., Conjugative transposons: an unusual and diverse set of integrated gene transfer elements. Microbial Rev. Dec. 1995;59(4):579-90. Review.
Scheiffele and Fuss. (2001) Induction of TNBS colitis in mice. Current Protocols in lmmunology. 15.19.1-15.19.14.
Schembri MA et al. Orientation-dependent enhancement by H-NS of the activity of the type 1 fimbrial phase switch promoter in *Escherichia coli*. (1998) Mol Gen Genet 259:336-44.
Schlegel et al., A synthetic random basic copolymer with promiscuous binding to class 11 major histocompatibility complex molecules inhibits T-cell proliferative responses to major and minor histocompatibility antigens in vitro and confers the capacity to prevent murine graft-versus-host disease in vivo. Proc Natl Acad Sci USA. May 14, 1996;93(10):5061-6. Erratum in: Proc Natl Acad Sci USA Aug. 6, 1996;93(16):8796.
Schneider et al., De nova design of molecular architectures by evolutionary assembly of drug derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from Trimeresurus wagleri which blocks the nicotinic acetylcholine receptor. Biophys J. Jan. 1996;70(1):3-13.
"Sepsis" from National Institute of General Medical Sciences, dated Jan. 2018 (3 pages).
Shaklee et al., Hydrazinolysis of heparin and other glycosaminoglycans. Biochem. J. (1984); 217:187-197.
Shapiro et al., Cellular control of abscess formation: role of T cells in the regulation of abscesses formed in response to Bacteroides fragilis. J Immunol. Jul. 1, 1986;137(1):341-6.
Shapiro et al., Cellular immunity to Bacteroides fragilis capsular polysaccharide. J Exp Med. Apr. 1, 1982;155(4) :1188-97.
Sharpe et al., The B7-CD28 superfamily. Nat Rev Immunol. Feb. 2002;2(2): 116-26. Review.
Shevach, CD4+ CD25+ suppressor T cells: more questions than answers. Nat Rev Immunol. Jun. 2002;2(6):389-400. Review.
Sigmundsdottir H, et al. (2007) DCs metabolize sunlight-induced vitamin D3 to 'program' T cell attraction to the epidermal chemokine CCL27. Nature immunology 8: 285-293.
Silvestro et al. "Effects of subinhibitory concentrations of clindamycin on the morphological, biochemical and genetic characteristics of Bacteroides fragilis" FEMS Microbiol. Lett. 2006; vol. 257; No. 2; pp. 189-194.
Simmons et al., Synthesis and membrane permeability of PNA-peptide conjugates. Bioorg Med Chem Lett. 1997;7(23):3001-6.
Slack, E., et al. (2009). Innate and adaptive immunity cooperate flexibly to maintain host-microbiota mutualism. Science 325, 617-620.
Smith SG et al. Functional analysis of the FimE integrase of *Escherichia coli* K-12: isolation of mutant derivatives with altered DNA inversion preferences. (1999) Mol Microbiol 34:965-79.
Smits, H.H. et al. "Selective probiotic bacteria induce IL-10-producing regulatory T cells in vitro by modulating dendritic cell function through dendritic cell-specific intercellular adhesion molecule 3-grabbing nonintegrin" J Allergy Clin Immunol. (2005) pp. 1260-1267.

(56) References Cited

OTHER PUBLICATIONS

Solomon AJ, et al. "Multiple Sclerosis and Vitamin D: A Review and Recommendations" Curr. Neurol Neurosci Rep.; 2010; vol. 10; pp. 389-396.
Spach KM, et al. (2005) Vitamin D3 confers protection from autoimmune encephalomyelitis only in female mice. J Immunol 175: 4119-4126.
Spach KM, et al. (2004) Gene expression analysis suggests that 1,25-dihydroxyvitamin D3 reverses experimental autoimmune encephalomyelitis by stimulating inflammatory cell apoptosis. Physiol Genomics 18: 141-151.
Sprinz, H. et al. (1961) The response of the germfree guinea pig to oral bacterial challenge with Escherichia coli and Shigella flexneri. Am J. Pathol. 39, 681-695.
Stein et al., Thymus-independent and thymus-dependent responses to polysaccharide antigens. J Infect Dis. Jun. 1992;165 Suppl I:S49-52. Review.
Stephen et al. "Effect of 87-2 and CD40 Signals from Activated Antigen-Presenting Cells on the Ability of Zwitterionic Polysaccharides to Induce T-Cell Stimulation" 2005; Inf. Immun. vol. 73; pp. 2184-2189.
Stewart N, et al. (2012) Interferon-beta and serum 25-hydroxyvitamin D interact to modulate relapse risk in MS. Neurology 79: 254-260.
Stromnes IM, et al. (2006) Active induction of experimental allergic encephalomyelitis. Nat Protoc 1: 1810-1819.
Stromnes et al., Passive induction of experimental allergic encephalomyelitis. Nat Protoc. 2006; 1(4):1952-60.
Suri-Payer et al., CD4+CD25+ T cells inhibit both the induction and effector function of autoreactive T cells and represent a unique lineage of immunoregulatory cells. J Immunol. Feb.1, 1998; 160(3):1212-8.
Szu et al., Relation between structure and immunologic properties of the Vi capsular polysaccharide. Infect Immun. Dec. 1991;59(12):4555-61.
Taconic, "Swiss Webster Outbred," Taconic Biosciences 2019, in 9 pages.
Takatori, N. "Probiotics, beneficial bacteria, and inflammatory bowel disease; What do we actually know?" Nutritional Bytes, 2009, vol. 13, pp. 1-6.
Tanaka, H. et al. "Human monocyte-derived dendritic cells induce naive T cell differentiation into T helper cell type 2 (Th2) of Th1/Th2 effectors: role of stimulator/responder ratio" Journal of Experimental Medicine; vol. 192; No. 3; Aug. 7, 2000; pp. 405-411.
Tang et al., Th type 1-stimulating activity of lung macrophages inhibits Th2-mediated allergic airway inflammation by an IFN-gamma-dependent mechanism. J Immunol. Feb. 1, 2001; 166(3): 1471-81.
Tang, et al. "In-vitro-expanded Antigen-specific Regulatory T cells suppress autoimmune diabetes" J. Exp. Med. vol. 199; No. 11; Jun. 7, 2004; pp. 1455-1465.
Taylor et al., Stoichiometric depolymerization of polyuronides and glycosaminoglycuronans to monosaccharides following reduction of their carbodiimide-activated carboxyl groups. Biochemistry. Apr. 11, 1972;11 (8): 1383-8.
Teitelbaum et al., Immunomodulation of experimental autoimmune encephalomyelitis by oral administration of copolymer 1. Proc Natl Acad Sci USA. Mar. 30, 1999;96(7):3842-7.
Teitelbaum et al., Specific inhibition of the T-cell response to myelin basic protein by the synthetic copolymer Cop 1. Proc Natl Acad Sci USA. Dec. 1988;85(24):9724-8.
Teitelbaum et al., Synthetic copolymer 1 inhibits human T-cell lines specific for myelin basic protein. Proc Natl Acad Sci USA. Jan. 1, 1992;89(1):137-41.
Teitelbaum et al., Unprimed spleen cell populations recognize macrophage-bound antigen with opposite net electric charge. Proc Natl Acad Sci USA. Apr. 1977;74(4): 1693-6.
Telesford, et al., "A commensal symbiotic factor derived from Bacteroides fragilis promotes human CD39+Foxp3+ T cells and Treg function," Gut Microbes, vol. 6: 234-242.Published online Jul. 31, 2015. 10 Pages.

Thomas et al., Randomised controlled trial of short bursts of a potent topical corticosteroid versus prolonged use of a mild preparation for children with mild or moderate atopic eczema. BMJ. 2002;324(7640):1-7.
Tong et al., "Mouse Models of Colorectal Cancer," Chin. J. Cancer, vol. 30, 450-62 (2011).
Torisu M., et al., "Significant Prolongation of Disease-Free Period Gained by Oral Polysaccharide K (PSK) Administration after Curative Surgical Operation of Colorectal Cancer," Cancer Immunology, Immunotherapy, vol. 31(5), Sep. 1, 1990, 8 pages, XP055323922.
Tournoy et al., Endogenous interleukin-10 suppresses allergen-induced airway inflammation and nonspecific airway responsiveness. Clin Exp Allergy. Jun. 2000;30(6):775-83.
Toussirot, E., et al., Bacterial extract (OM-89) specific and non specific immunomodulation in rheumatoid arthritis patients, Autoimmunity 2006, 39: 299-306 Abstract Only.
Triantafillidis et al., "Colorectal Cancer and Inflammatory Bowel Disease: Epidemiology, Risk Factors, Mechanisms of Carcinogenesis and Prevention Strategies," Anticancer Res., vol. 29, 2727-37 (2009).
Troy, E. et al .. "Beneficial effects of Bacteroides fragilis polysaccharides on the immune system." Front Biosci., Jan. 1, 2010, vol. 15; pp. 25-34.
Troy, E et al., "Orientations of the Bacteroides fragilis capsular polysaccharide biosynthesis locus promoters during symbiosis and infection", Journal of Bacteriology, Nov. 2010, vol. 192, No. 21, pp. 5832-5836.
Tzianabos et al. "T-Cells Activated by Zwitterionic Molecules prevent abscesses induced by pathogenic bacteria" J. Biol. Chem. 2000; vol. 275; No. 10; pp. 6733-6740.
Tzianabos et al., Bacterial structure and functional relation to abscess formation. Infect Agents Dis. Oct. 1994;3(5):256-65. Review.
Tzianabos et al., Characteristics of bacterial polysaccharides that activate T cells. The International Carbohydrate Symposium XVII. Jul. 21, 1994. 1 page.
Tzianabos et al., Effect of surgical adhesion reduction devices on the propagation of experimental intra-abdominal infection. Arch Surg. Nov. 1999;134(11):1254-9.
Tzianabos et al., IL-2 mediates protection against abscess formation in an experimental model of sepsis. J lmmunol.Jul. 15, 1999;163(2):893-7.
Tzianabos et al., Protection against Experimental Intraabdominal Sepsis by Two Polysaccharide Immunomodulators. J Infect Dis. Jul. 1998;178(1):200-6.
Tzianabos et al., Structure-function relationships for polysaccharide-induced intra-abdominal abscesses. Infect Immun. Aug. 1994;62(8):3590-3.
Tzianabos et al., T Cell Activation by Zwitterionic polysaccharides and peptide mimetics prevents intrabdominal abscess formation. Abstracts of the 99th General Meeting of the American Society for Microbiology. Chicago, US: May 30-Jun. 3, 1999. Jun. 28, 1999; 1 page.
Tzianabos, A.O., Polysaccharide Immunomodulators as Therapeutic Agents: Structural Aspects and Biologic Function, Clin. Microbial. Rev. 13(4):523-533 (2000).
Tzianabos, AO et al., Polysaccharide-mediated protection against abscess formation in experimental intra-abdominal sepsis. J Clin. Investi. (1995) 96:2727-31.
Tzianabos, et al., Structural rationale for the modulation of abscess formation by Staphylococcus aureus capsular polysaccharides. Proc Natl Acad Sci USA. Jul. 31, 2001 ;98(16):9365-70. Epub Jul. 24, 2001.
Uronis et al., "Modulation of the Intestinal Microbiota Alters Colitis-Associated Colorectal Cancer Susceptibility," PLoS ONE, vol. 4, e6026 (2009).
Van Scott et al., IL-10 reduces Th2 cytokine production and eosinophilia but augments airway reactivity in allergic mice. Am J Physiol Lung Cell Mol Physiol. Apr. 2000;278(4):L667-74.
Vann et al., The structure of the capsular polysaccharide (K5 antigen) of urinary-tract-infective Escherichia coli 010:K5:H4. A polymer similar to desulfo-heparin. Eur J Biochem. May 15, 1981;116(2):359-64.

(56) References Cited

OTHER PUBLICATIONS

Vázquez et al., "Therapeutic drug monitoring of vacomycin in severe sepsis and septic shock," International Journal of Clinical Pharmacology and Therapeutics 2008, 46, 140-145.
Veldhoen, M et al. "TGF beta in the context of an inflammatory cytokine milieu supports de novo differentiation of IL-17-producing T cells." Immunity; vol. 24; pp. 179-189.
Velez et al., Type I *Streptococcus pneumoniae* carbohydrate utilizes a nitric oxide and MGC 11-dependent pathway for antigen presentation. Immunol. 2008; 127:73-82.
Verdu et al., Oral administration of antigens from intestinal flora anaerobic bacteria reduces the severity of experimental acute colitis in BALB/c mice. Clin Exp Immunol. Apr. 2000;120(1):46-50.
Vignali, DA et al. "How regulatory T cells work." Nat. Rev. Immunol.; 2008; vol. 8; pp. 523-532.
Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.
Viret et al., Molecular cloning and characterization of the genetic determinants that express the complete Shigella serotype D (Shigella sonnei) lipopolysaccharide in heterologous live attenuated vaccine strains. Mol Microbial. Jan. 1993;7(2):239-52.
Wagner et al., Use of reporter cells to study endogenous retinoid sources in embryonic tissues. Methods Enzymol. 1997;282:98-107.
Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.
Wang et al., Ozonolysis for selectively depolymerizing polysaccharidescontaining β-d-aldosidic linkages. Proc Natl Acad Sci USA. Jun. 9, 1998; 95(12): 6584-6589.
Wang et al., Structural basis of the abscess-modulating polysaccharide A2 from Bacteroides fragilis. Proc Natl Acad Sci USA. Dec. 5, 2000;97(25): 13478-83.
Wang et al., Structure characterization of an abscessogenic capsular polysaccharide from Bacteriodes fragilis by NMR spectroscopy. XIX International Conference of NMR in Biological Systems. Florence, Italy Aug. 20-25, 2000. Abstract.
Ward et al., The nucleotide sequence of the tnpA gene of Tn21, Nucleic Acids Research, vol. 15(4), 1987, 1799-1806.
Wehr et al., Anti-low-density lipoprotein antibodies in alcoholics without and with liver disease and in social drinkers. Alcohol & Alcoholism. Jan.-Feb. 1997;32(1):43-9.
Weinacht et al. Phase variation of the capsular polysaccharides of Bacteroides fragilis is dictated by site-specific recombinases. 2002 General Meeting of the American Society for Microbiology, May 19-23, 2002. Abstract.
Wen, L et al. "Innate immunity and intestinal microbiota in the development of Type 1 diabetes" Nature; 2008; vol. 455; pp. 1109-1113.
Wessels et al., Structural Determination and Immunochemical Characterization of the Type V Group B *Streptococcus* Capsular Polysaccharide, The Journal of Biological Chemistry, 266:6714-6719, 1991.
Wessels et al., Structure and immunochemistry of an oligosaccharide repeating unit of the capsular polysaccharide of Type 111 group B *Streptococcus*. A revised structure for the type 111 group B streptococcal polysaccharide antigen. J Biol Chem. Jun. 15, 1987;262(17):8262-7.
Wexler, Bacteroides: the good, the bad, and the nitty-gritty. Clin Microbiol Rev. Oct. 2007;20(4):593-621.
Whitfield, Biosynthesis and assembly of capsular polysaccharides in *Escherichia coli*. Annu Rev Biochem. 2006;75:39-68.
Wiegandt et al., Carbohydrate Components of Extraneuronal Gangliosides from Bovine and Human Spleen, and Bovine Kidney, European Journal of Biochemistry, 15:287-292, 1970.
Wilier CJ, et al. (2003) Twin concordance and sibling recurrence rates in multiple sclerosis. Proc Natl Acad Sci USA 100: 12877-12882.
Wingate K. et al., "25-Hydroxyvitamin D Concentrations in Children with Crohn's Disease Supplemented with Either 2000 or 400 IU Daily for 6 Months: A Randomized Controlled Study" The Journal of Pediatrics, vol. 164, No. 4,Apr. 2014, pp. 860-865 6 pages.
Wiriz et al., Mouse models of inflammatory bowel disease. Adv Drug Deliv Rev. Sep. 30, 2007;59( 11):1073-83. Eoub Aug. 16, 2007.
Woessner et al., Long-term antibiotic treatment with roxithromycin in patients with multiple sclerosis. Infection. Dec. 2006;34(6):342-4.
Written Opinion for International Application PCT/US2016/037044 filed Jun. 10, 2016 on behalf of California Institute of Technology, datd Sep. 22, 2016. 8 pages.
Wu HJ, et al. (2010) Gut-residing segmented filamentous bacteria drive autoimmune arthritis via T helper 17 cells. Immunity 32: 815-827.
Wujek et al., A carbohydrate polymer that effectively prevents epidural fibrosis at laminectomy sites in the rat. Exp Neural. Nov. 1991;114(2):237-45.
Xavier et al. "Unravelling the pathogenesis of inflammatory bowel disease", Nature, Jul. 26, 2007, pp. 427-434, 448.
Xu J et al., A genomic view of the human-Bacteroides thetaiotaomicron symbiosis. Science. Mar. 28, 2003;299(5615):2074-6.
Yamakazi et al. "Dendritic cells are specialized accessory cells along with TGF-beta for the differentiation of Foxp3+ CD4+ regulatory T cells from peripheral Foxp3- precursors" Blood. 2007; 110: 4293-4302.
Yamazaki, T. et al. "CCR6 regulates the migration of inflammatory and regulatory T cells" J. Immunology; 2008; vol. 181; pp. 8391-8401.
Yang J. et al., "Targeting Th17 cells in autoimmune diseases" Cell Press, vol. 35, No. 10,Oct. 2014, pp. 493-500 8 pages.
Yokoyama et al., Adhesion behavior of rat lymphocytes to poly(ether)-poly(amino acid) block and graft copolymers. J Biomed Mater Res. Sep. 1986;20(7):867-78.
Yoshii, Cytotoxic effects of acrylates and methacrylates: relationships of monomer structures and cytotoxicity. J Biomed Mater Res. Dec. 15, 1997;37(4):517-24.
Zabad et al., The clinical response to minocycline in multiple sclerosis is accompanied by beneficial immune changes: a pilot study. Mult Scler. May 2007;13(4):517-26. Epub Feb. 9, 2007.
Zaleznik et al., A soluble suppressor T cell factor protects against experimental intraabdominal abscesses. J Clin Investi. Mar. 1985;75(3):1023-7.
Zaph, C., et al. (2008). Commensal-dependent expression of IL-25 regulates the IL-23-IL-17 axis in the intestine. J Exp Med 205, 2191-2198.
Zehnder D, et al. (1999) Expression of 25-hydroxyvitamin D3-1 alpha-hydroxylase in the human kidney. J Am Soc Nephrol 10: 2465-2473.
Zehnder D, et al. (2001) Extrarenal expression of 25-hydroxyvitamin d(3)-1 alpha-hydroxylase. J Clin Endocrinol Metab 86: 888-894.
Zhang et al., Degradation of Wood Polysaccharide Model Compounds During Ozone Treatment. Journal of Pulp and Paper Science. Jan. 1997;23(1):J23-J27.
Zhang X., et al., "Calcium, Vitamin D and Colorectal Cancer Chemoprevention," Bailliere's Best Practice and Research, Clinical Gastroenterology, vol. 25(4), Jan. 1, 2011, 10 pages.
Zhang et al., IL-10 is involved in the suppression of experimental autoimmune encephalomyelitis by CD25+CD4+ regulatory T cells. Int Immunol. Feb. 2004;16(2):249-56.
Zhao H et al. In vivo phase variation of MR/P fimbrial gene expression in Proteus mirabilis infecting the urinary tract. (1997) Mol Micro biol 23: 1009-19.
Zhou, L et al. "TGF-beta-induced Foxp3 inhibits T(H)17 cell differentiation by antagonizing RORgammat function" Nature; 2008; vol. 453; pp. 236-240.
Zhu et al., Oral administration of type-11 collagen peptide 250-270 suppresses specific cellular and humoral immune response in collagen-induced arthritis. Clin Immunol. Jan. 2007; 122(1 ):75-84. Epub Oct. 11, 2006.

(56) References Cited

OTHER PUBLICATIONS

Zouali, M. et al., "Marginal Zone B-Cells, A Gatekeeper of Innate Immunit", Frontiers in Immunology, vol. 2, Article 63, 10 pages, (2011).
Davila et al., "Efficacy and Toxicity Management of 19-28z CAR T Cell Therapy in B Cell Acute Lymphoblastic Leukemia," Sci Transl Med 2014, 6(224), in 23 pages.
Final Office Action dated Apr. 5, 2021 in U.S. Appl. No. 15/179,810.
Final Office Action dated Feb. 9, 2021 in U.S. Appl. No. 16/562,358.
Head & Jurenka, "Inflammatory Bowel Disease Part I: Ulcerative Colitis—Pathophysiology and Conventional and Alternative Treatment Options," Alternative Medicine Review 2003, 8(3), 247-283.
Non-Final Office Action dated Apr. 19, 2021 in U.S. Appl. No. 16/386,522.
Notification of Reasons for Refusal dated Feb. 26, 2021 in Japanese Patent Application No. 2020-006703.
Notification of Reasons for Refusal dated Jan. 26, 2021 in Japanese Patent Application No. 2019-061261.
Notification of Reasons for Refusal dated Mar. 5, 2021 in Japanese Patent Application No. 2020-006706.
Restriction Requirement dated Jan. 14, 2021 in U.S. Appl. No. 16/386,522.
Examination Report dated Apr. 7, 2021 in Canadian Patent Application No. 2,911,826.
Final Office Action dated Oct. 4, 2021 in U.S. Appl. No. 16/562,358.
Final Office Action dated Oct. 21, 2021 in U.S. Appl. No. 16/388,522.
Fichtner-Feigl et al., "Treatment of murine Th1- and Th2-mediated inflammatory bowel disease with NF-$_K$B decoy oligonucleotides," The Journal of Clinical Investigation 2005, 115(11), 3057-3071.
LI & He, "I L-10 and its related cytokines for treatment of inflammatory bowel disease," World Journal of Gastroenterology 2004, 10(5), 620-625.
Non-Final Office Action dated May 18, 2021 in U.S. Appl. No. 16/562,358.
Non-Final Office Action dated Aug. 23, 2021 in U.S. Appl. No. 15/179,810.
Notice of Allowance dated Aug. 20, 2021 in Japanese Patent Application No. 2020-006703.
Notice of Allowance dated Aug. 27, 2021 in Japanese Patent Application No. 2019-061261.
Notice of Allowance dated Oct. 25, 2021 in Japanese Patent Application No. 2020-006706.
Notification of Reasons for Refusal dated Aug. 13, 2021 in Japanese Patent Application No. 2020-006706.

* cited by examiner

FIG. 1A
FIG. 1B
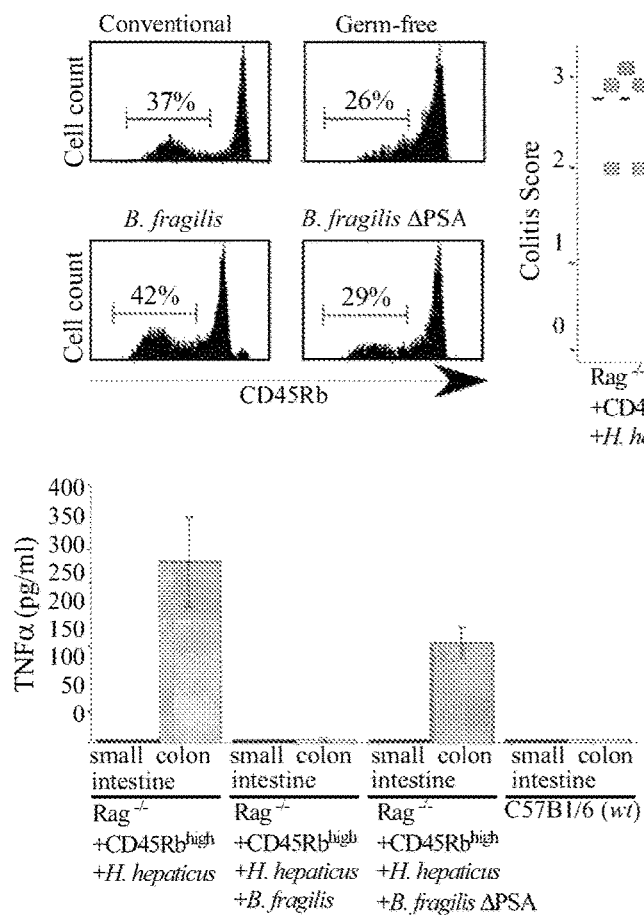
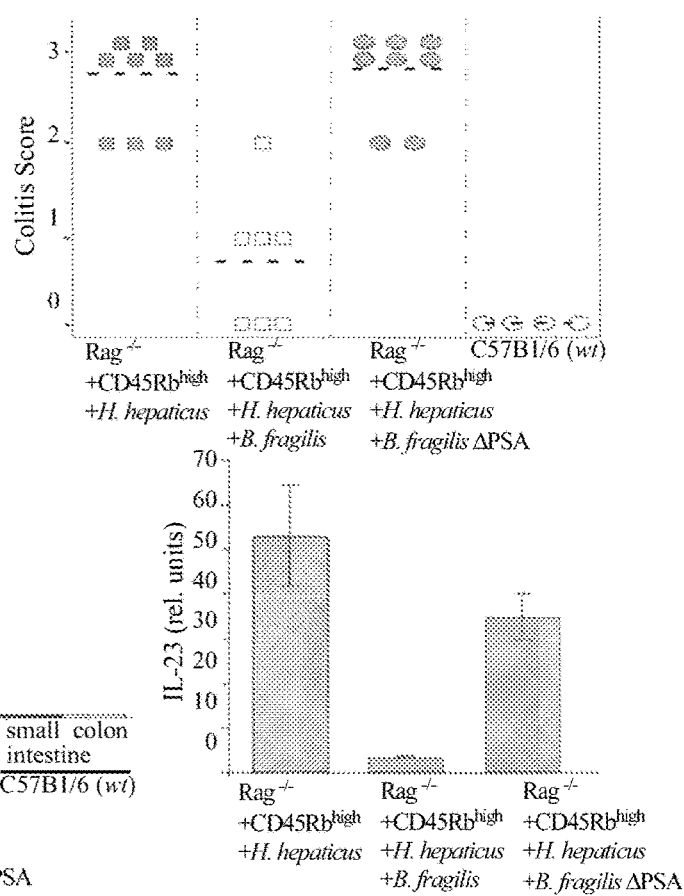
FIG. 1C
FIG. 1D

FIG. 4A
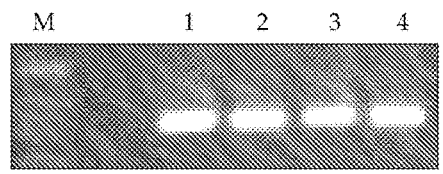
FIG. 4B
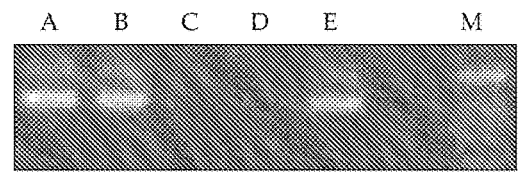
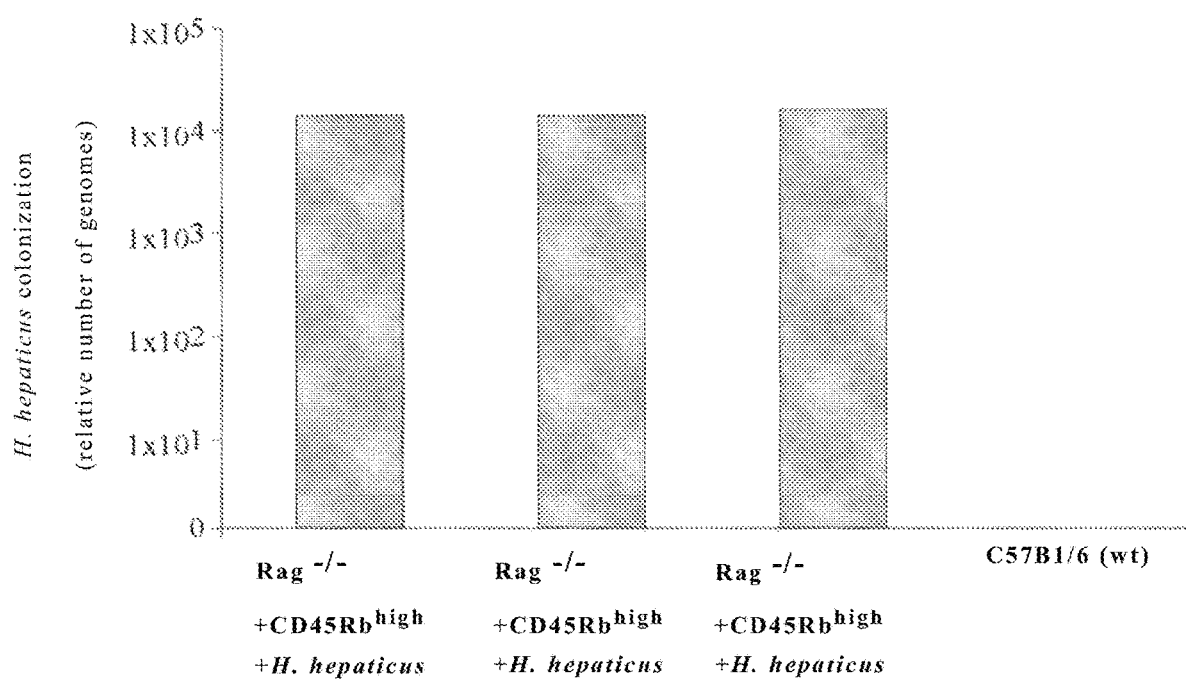
FIG. 5

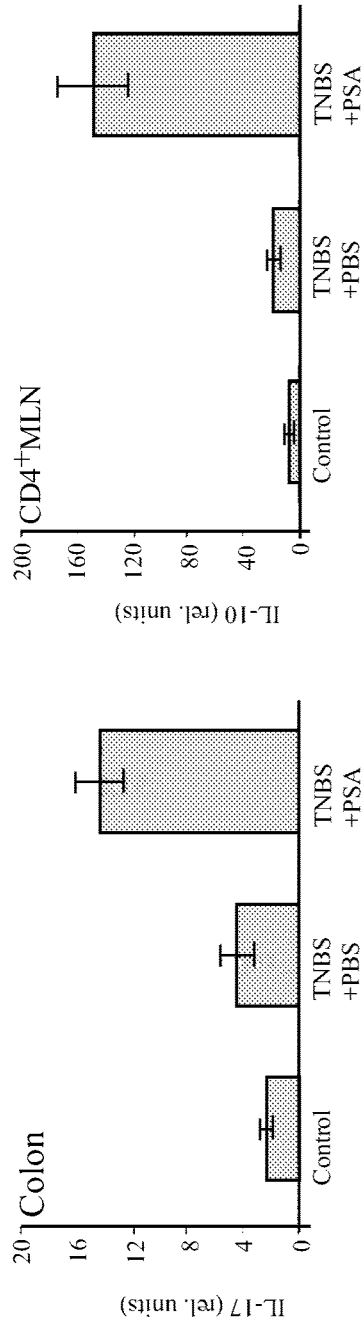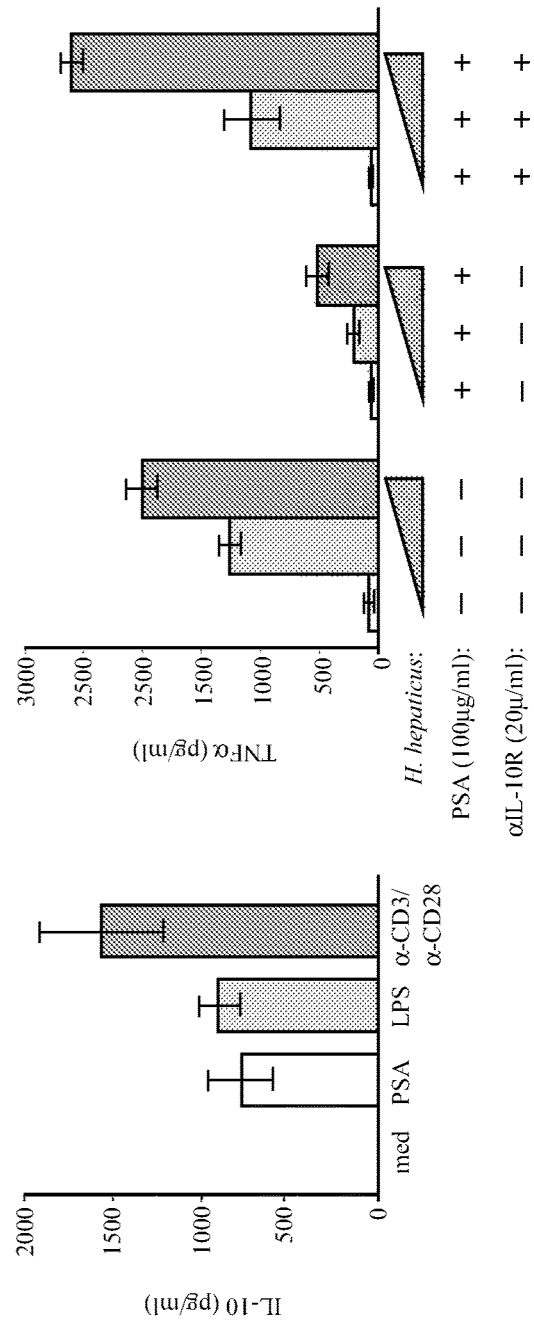
FIG. 8A
FIG. 8B
FIG. 8C
FIG. 8D

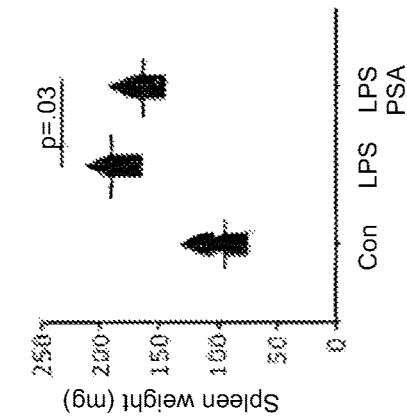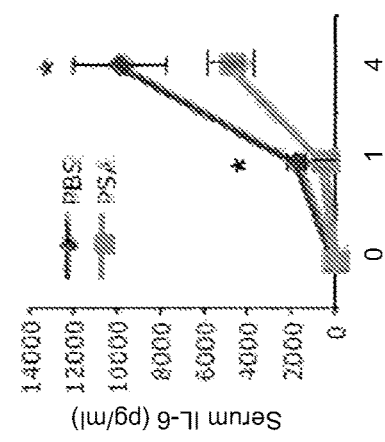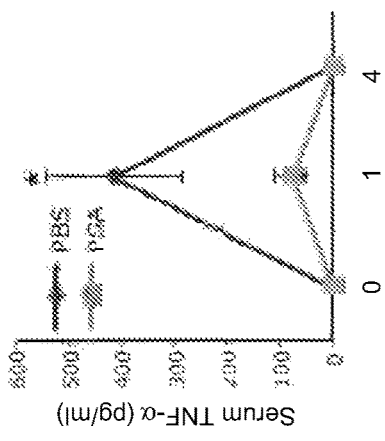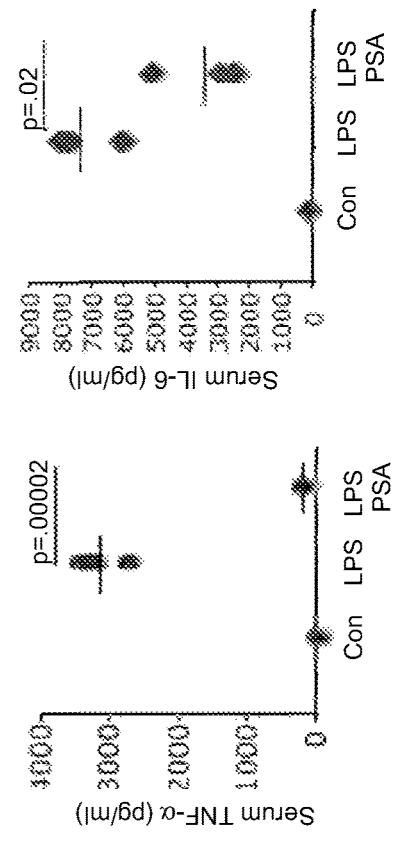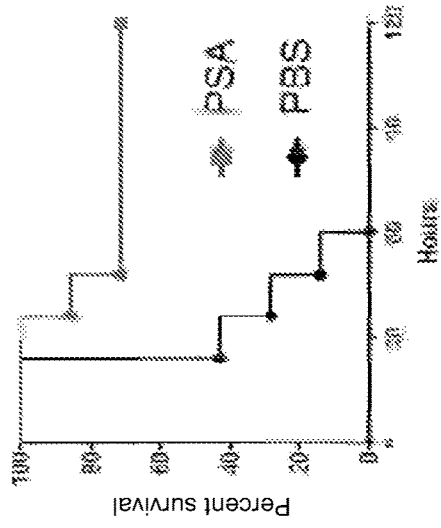
FIG. 17A FIG. 17B FIG. 17C
FIG. 17D FIG. 17E FIG. 17F

IMMUNOMODULATING COMPOUNDS AND RELATED COMPOSITIONS AND METHODS

CROSS REFERENCE

This application claims benefit and is a Continuation of application Ser. No. 14/660,827 filed Mar. 17, 2015, now abandoned, which is a continuation of U.S. patent application Ser. No. 13/464,876, filed on May 4, 2012, now abandon, which is a continuation of U.S. patent application Ser. No. 12/267,602, filed on Nov. 9, 2008, now abandon, which claims benefit of U.S. Provisional Application No. 61/196,046, filed on Oct. 14, 2008, 61/008,407, filed on Dec. 20, 2007, and 61/002,705, filed on Nov. 9, 2007 which applications are incorporated herein by reference in their entirety.

FEDERALLY SPONSORED RESEARCH AND DEVELOPMENT

This invention was made with Government support under Grant A1039576 awarded by the National Institutes of Health. The government has certain rights in the invention.

FIELD

The present disclosure relates to the immune system, and, in particular, to an immunomodulating compound able to control T cell differentiation and/or cytokines production associated with an immunitary response in an individual.

BACKGROUND

T cells belong to a group of white blood cells known as lymphocytes, and play a central role in cell-mediated immunity. In particular, T helper cells (also known as effector T cells or Th cells) are a sub-group of lymphocytes (a type of white blood cell or leukocyte) that plays an important role in establishing and maximizing the capabilities of the immune system and in particular in activating and directing other immune cells. More particularly, Th cells are essential in determining B cell antibody class switching, in the activation and growth of cytotoxic T cells, and in maximizing bactericidal activity of phagocytes such as macrophages.

Different types of Th cells have been identified that originate in outcome of a differentiation process and are associated with a specific phenotype. Following T cell development, matured, naïve (meaning they have never been exposed to the antigen to which they can respond) T cells leave the thymus and begin to spread throughout the body. Once the naïve T cells encounter antigens throughout the body, they can differentiate into a T-helper 1 (Th1), T-helper 2(Th2), T-helper 17 (Th17) or regulatory T cell (Treg) phenotype.

Each of these Th cell types secretes cytokines, proteins or peptides that stimulate or interact with other leukocytes, including $T_h$ cells. However, each cell type has a peculiar phenotype and activity that interferes and often conflict with the other.

Th1, Th2, and Th17 (inflammatory T-helper or inflammatory Th), promote inflammation responses trough secretion of pro-inflammatory cytokines, such as IL-1, IL-6, TNF-a, IL-17, IL21, IL23, and/or through activation and/or inhibition of other T cell including other Th cells (for example Th1 cell suppresses Th2 and Th17, Th2 suppresses Th1 and Th17). Tregs instead, are a component of the immune system that suppresses biological activities of other cells associated to an immune response. In particular, Tregs can secrete immunosuppressive cytokines TGF-beta and Interleukin 10, and are known to be able to limit or suppress inflammation.

An imbalance in the profile of any of the inflammatory T-helper cells is usually associated with a condition in an individual. For example, an increase profile for Th1 or Th17 leads to autoimmunity, whereas an increased Th2 cell profile leads to allergies and asthma. In particular, imbalance of Th17 cell profile has been associated with several autoimmunitary conditions. Treg cells suppress inflammation induced by all 3 other T cell lineages, and thus are crucial for preventing uncontrolled inflammation, which leads to disease. Therefore, a balanced T-helper profile is critical for health in individuals.

SUMMARY

Provided herein, are immunomodulating compounds and related methods and compositions that are suitable to balance a T-helper cell profile, and in particular to balance the cell profile of at least one of Th1, Th2, Th17 and Treg cells in an individual. More particularly, provided herein are methods and compositions based on the surprising immunomodulating properties of PSA polysaccharide A (PSA) and other zwitterionic polysaccharides (ZPs) that make those polysaccharides suitable for treatment, prevention and control of inflammations and inflammatory conditions in an individual.

According to a first aspect, a method to balance a T-helper cell profile in an individual is disclosed. The method comprises administering to the individual an effective amount of a zwitterionic polysaccharide.

According to a second aspect, a method to balance a cell profile of at least one Th cell selected from the group consisting of Th1, Th2, Th17 and Treg, in an individual is disclosed. The method comprises administering to the individual an effective amount of a zwitterionic polysaccharide.

According to a third aspect, a method to control cytokine production in an individual, is disclosed, the cytokine being at least one of IL-1, IL-6, TNF-a, IL-17, IL21, IL23. The method comprises administering to the individual an effective amount of a zwitterionic polysaccharide.

According to a fourth aspect, a method to control inflammation associated with a Th-cell profile imbalance in an individual is disclosed. The method comprises administering to the individual an effective amount of a zwitterionic polysaccharide.

According to a fifth aspect, a method to treat or prevent conditions associated with an imbalanced cell profile of at least one Th cell selected from the group consisting of Th1, Th2, Th17 and Treg in an individual is disclosed. The method comprises administering to the individual an effective amount of a zwitterionic polysaccharide.

According to a sixth aspect, a method to treat or prevent conditions associated with production of at least one of IL-1, IL-6, TNF-a, IL-17, IL21, IL23 cytokines in an individual, is disclosed. The method comprises administering to the individual an effective amount of a zwitterionic polysaccharide.

According to a seventh aspect, an anti-inflammatory composition is disclosed. The anti-inflammatory composition comprises a zwitterionic polysaccharide and a suitable vehicle, wherein the zwitterionic polysaccharide is comprised in an amount of from about 1 to about 100 µg.

The compositions and methods herein disclosed can be used in several embodiments to simultaneously control and balance the profile of Th1, Th2, Th17 and Treg cells in an individual, thus preventing or treating conditions associated with an imbalanced profile for those cytokines in the individual.

The compositions and methods herein described can be used in connection with medical, pharmaceutical, veterinary applications as well as fundamental biological studies and various applications, identifiable by a skilled person upon reading of the present disclosure, wherein investigating the possible role of a zwitterionic polysaccharide is desirable The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1D shows an exemplary ZP mediated protection from experimental colitis in individuals according to some embodiments herein disclosed. FIG. 1A shows diagrams summarizing the results of mono-association of germ-free mice with wild-type B. fragilis and B. fragilis DPSA (mean percentages±Standard Deviation (SD) for 3 experiments: conventional, 38.4%±2.2; germ-free, 26.7%±1.3; B. fragilis, 40.8%±3.1; B. fragilis DPSA, 28.8%±2.6). All cells gated on $CD4^+$ splenocytes. FIG. 1B shows a diagram illustrating the results of co-colonization experiments of H. hepaticus with B. fragilis and B. fragilis DPSA (two-tailed p value, 0.004; Mann-Whitney U test). Combined data from 2 independent experiments are shown. Error bars show SD for triplicate samples. FIG. 1C shows a diagram illustrating the results of ELISA test of colon organ cultures to detect TNFa levels in animals co-colonized with H. hepaticus and wild-type B. fragilis or B. fragilis DPSA. FIG. 1D shows a diagram illustrating the results of a Q-PCR for IL-23p19 performed on splenocytes, normalized to L32 expression. Error bars show SD for triplicate samples.

FIG. 2 shows diagrams illustrating the results of ELISA tests for the detection of the pro-inflammatory cytokines IL-12p40 (top) and IL-1b (bottom) in animals co-colonized with H. hepaticus and wild-type B. fragilis or B. fragilis DPSA over those in control animals (C57BL/6). Results are from one trial of 2 independent experiments. Error bars indicate SD values from studies of colons recovered from 4 animals per group.

FIG. 4A-4B shows control experiments supporting various embodiments herein described. FIG. 4A shows an ethidium bromide—stained gel electrophoresis of H. hepaticus—specific Q-PCR performed following co-colonization with wild-type and various mutants of B. fragilis after 8 weeks. M: Marker. 1: $Rag2^{-/-}$ animals with $CD4^+$–$CD45Rb^{high}$ T cell transfer colonized with H. hepaticus alone. 2: $Rag2^{-/-}$ animals with $CD4^++CD45Rb^{high}$ T cell transfer colonized with H. hepaticus and B. fragilis 9343 (wt). 3: $Rag2^{-/-}$ animals with $CD4^++CD45Rb^{high}$ T cell transfer colonized with H. hepaticus and B. fragilis DPSA. 4: C57BL/6 mice colonized with H. hepaticus alone. Note: H. hepaticus readily colonized animals but did not induce disease (FIG. 1). Primers for H. hepaticus 16S rDNA: (HB-15) 5'-GAAACTGTTACTCTG-3' (SEQ ID NO: 1) and (HB-17) 5'-TCAAGCTCCCCGAAGGG-3'(SEQ ID NO: 2). FIG. 4B shows ethidium bromide—stained gel electrophoresis of B. fragilis—specific Q-PCR performed following co-colonization with wild-type and various mutants of B. fragilis after 8 weeks. A: $Rag2^{-/-}$ animals with $CD4^+$ $CD45Rb^{high}$ T cell transfer colonized with H. hepaticus and B. fragilis 9343 (wt). B: $Rag2^{-/-}$ animals with $CD4^+$ $CD45Rb^{high}$ T cell transfer colonized with H. hepaticus and B. fragilis DPSA. C: $Rag2^{-/-}$ animals with $CD4^+$ $CD45Rb^{high}$ T cell transfer colonized with H. hepaticus alone. D: C57BL/6 mice colonized with H. hepaticus alone. E: B. fragilis genomic DNA (positive control). M: Marker. Primers for B. fragilis ssr3 (finB) gene: (ssr3-F) 5'-TAT-TTGCGAGAAGGTGAT-3' (SEQ ID NO: 3) and (ssr3-r) 5'-TAAACGCTTTGCTGCTAT-3'(SEQ ID NO: 4).

FIG. 5 effects associated to a ZP-mediated protection according to some embodiments herein disclosed. In particular, FIG. 5 shows a diagram illustrating the results of Q-PCR experiments directed to quantitate H. hepaticus in animals co-colonized with H. hepaticus and wild-type B. fragilis or B. fragilis DPSA. The results was assessed according to Young et al., 2004[1] as $\log^{10}$ number of copies of a known gene (cytolethal distending toxin). Animals contained equivalent levels of H. hepaticus at the end of the experiment.

FIG. 6A shows a diagram illustrating the results of a colonization with H. hepaticus in absence (second column) or in presence of purified PSA (third column) (Kruskal-Wallis comparisons of all groups: p>0.05 for dissimilar results, p<0.01 for similar results; Mann-Whitney U test: two-tailed p value, 0.0002). FIG. 6B shows a diagram illustrating results of experiments directed to detect wasting disease in $Rag2^{-/-}$ animals following transfer of $CD4^+CD45Rb^{high}$ T cells and colonization with H. hepaticus (PBS+Hh) in presence or absence of PSA as indicated. ANOVA indicates that comparisons between all indicated groups (asterisks) are statistically significant. FIG. 6C shows the architecture of colonic sections from wild-type animals (left panel); following transfer of $CD4^+CD45Rb^{high}$ T cell into Helicobacter-colonized $Rag2^{-/-}$ mice (middle panel); oral PSA treatment of Helicobacter—colonized animals (right panel). Images in each row are the same magnification.

FIG. 7A shows a diagram illustrating the correlation between oral PSA administration and body weight related to TNBS-treated PBS controls. ANOVA values for all indicated groups (asterisks) are statistically significant. Error bars show SD between 4 animals per group. FIG. 7B shows colon sections from TNBS+PBS-treated groups, from TNBS+

PSA-treated animals and from a control (representative sections from animals in 2 independent experiments). FIG. 7C-7D show diagram illustrating the results of Q-PCR of purified CD4+ T cells from MLNs with IL-17A (FIG. 7C) and TNFa (FIG. 7D) in presence or absence of PSA during disease. Error bars are from duplicate runs of 3 independent experiments. FIG. 7E-7F show diagrams illustrating transcriptional expression of IL17A (FIG. 7E) and TNFα (FIG. 7F) from homogenized colons of TNBS+PBS-treated groups, from TNBS+PSA-treated animals and from a control. Error bars are from duplicate runs of 3 independent experiments.

FIG. 8A-8D shows a ZP mediated control of cytokine expression according to some embodiments herein disclosed. FIG. 8A shows a diagram illustrating the results of Q-PCR assay of colons for IL-10 in wild type mice treated with ethanol (control), TNBS, or TNBS and PSA. Error bars show SD for triplicate samples. FIG. 8B shows a diagram illustrating Q-PCR results for IL-10 expression in CD4− T cells purified from MLNs of TNBS-treated groups. Error bars show SD for triplicate samples. FIG. 8C shows a diagram illustrating the effects of incubation of BMDC/T cell co-cultures with purified PSA LPS and a-CD3/a-CD28 on IL-10 production. Error bars show SD for triplicate samples. FIG. 8D shows a diagram illustrating the results of an infection of BMDC-T cell co-cultures with increasing concentrations of $H.$ $hepaticus$ (multiplicity of infection: 0.1, 1.0, and 10, as depicted by triangles) on TNFa release in presence (middle three bars) or absence (left three bars) of PSA and following the addition of aIL-10R right three bars. Error bars show SD values of experiments run in triplicate.

FIG. 9 shows a diagram illustrating the results for an IL-10 ELISA of supernatants of primary BMDC-T cell co-cultures incubated for 48 hours with $H.$ $hepaticus$ alone or with $H.$ $hepaticus$ and $B.$ $fragilis$ (wild-type or ΔPSA) at a multiplicity of infection of 5. Error bars show SD values for samples run in duplicate and represent 3 independent experiments.

FIG. 10 shows a diagram illustrating the results of an infection of BMDC-T cell co-cultures with increasing concentrations of live $H.$ $hepaticus$ (multiplicity of infection: 0.1, 1.0, and 10, as depicted by triangles) on release of the cytokine IL-1b in presence (middle three bars) or absence (left three bars) of PSA and following the addition of aIL-10R right three bars. Error bars show SD values for experiments run in triplicate.

FIG. 11A-11B show diagrams illustrating results of ELISA detection for pro-inflammatory cytokines TNFα (Panel a) and IL-17A (Panel b) in IL-10$^{-/-}$ mice left uncolonized (control) or colonized with $H.$ $hepaticus$ (to induce inflammation) either alone or in combination with $B.$ $fragilis$ (wild-type or APSA). Error bars show SD for triplicate samples. FIG. 11C shows a diagram illustrating the colitis scores in Rag$^{-/-}$ animals with CD4$^+$CD45Rb$^{high}$ T cell transfer colonized with $H.$ $hepaticus$ with or without PSA and in presence of neutralizing antibodies to IL-10 block (α-IL10R). Data represent 2 independent experiments. FIG. 11D shows a diagram illustrating colitis scores in Rag$^{-/-}$ animals with CD4$^+$CD45Rb$^{high}$ T cell transferred from IL-10$^{-/-}$ mice colonized with $H.$ $hepaticus$ with PSA or PBS. Results are shown for 1 representative trial of 2 independent experiments. FIG. 11E shows histologic colon sections Rag$^{-/-}$ animals with CD4$^+$CD45Rb$^{high}$ T cell transferred from IL-10$^{-/-}$ mice colonized with $H.$ $hepaticus$ with PSA or PBS. All images are the same magnification. FIG. 11F shows a diagram illustrating the mean body weights for groups of Rag$^{-/-}$ animals (n=4) with CD4$^+$CD45Rb$^{high}$ T cell transferred from IL-10$^{-/-}$ mice colonized with $H.$ $hepaticus$ with PSA or PBS.

FIG. 12 shows a diagram illustrating the variation on body weight in groups of 4 C57BL/6 mice treated with PSA (or PBS) and then subjected to rectal administration of TNBS or vehicle (control). Mean body weights (shown as percentages of initial weight) are shown for each group; SD values indicate that, in the absence of IL-10, PSA cannot restore TNBS-induced weight loss. ANOVA demonstrates that weight loss in both TNBS-treated groups is statistically different from that in control animals.

FIG. 13 shows results of histologic analysis of H&E-stained sections from a representative animal of groups of 4 C57BL/6 mice treated with PSA (or PBS) and then subjected to rectal administration of TNBS or vehicle (control). Results represent 2 independent experiments.

FIG. 14A shows a diagram illustrating the colonic histological score detected in untreated mice (control) and in mice treated with TNBS or TNBS/PSA. Each dot represents an individual mouse and the line indicates the average score of the group. FIG. 14B shows a diagram illustrating the percent of survival in time of Balb/c mice undergoing TNBS induced colitis. n=16 mice in each group. FIG. 14C shows an image of the spleen of untreated mice (control) and mice treated with TNBS or TNBS/PSA FIG. 14D shows a diagram illustrating the relative units of TNF-α, IL-6, IL-17A and IL-10 within CD4+ splenocytes in untreated mice (control) and in mice treated with TNBS or TNBS/PSA. These data are representative of three independent experiments.

FIG. 15A shows a diagram illustrating the percent survival of mice undergoing TNBS induced colitis. n=10 mice in each group. FIG. 15B shows a diagram illustrating variation of the spleen weight in untreated mice (Etoh) and in mice treated with TNBS or TNBS/PSA systemically administered. The weight of the spleen was used as an indicator of size. Each diamond represents the weight of the spleen from an individual animal. The bar indicates the average weight of the group. P values were determined by students T test.

FIG. 16A shows a diagram illustrating TNF-α production in CD4+ T lymphocytes residing within the mesenteric lymph nodes (MLN) splenocytes in untreated mice (control) and in mice treated with TNBS or TNBS/PSA. Cells were collected from the MLN and stained with antibodies recognizing CD4 or TNF-a. Numbers within quadrants represent the percentage of cells. FIG. 16B shows a diagram illustrating analysis of the expression of IL-12, IL-23, and IL-17 in colon of untreated mice (control) and mice treated with TNBS or TNBS/PSA. FIG. 16C show a diagram illustrating TNF-α production in CD4+ T lymphocytes residing within the spleen of untreated mice (control) and of mice treated with TNBS or TNBS/PSA. Numbers within quadrants represent the percentage of cells. FIG. 16D a diagram illustrating analysis of the expression of IL-12, IL-6, and IL-17 in spleen of untreated mice (control) and mice treated with TNBS or TNBS/PSA.

FIG. 17A-17F shows inhibition of inflammation and death associated with systemic septic shock following administration of ZPS according to some embodiments herein disclosed. FIG. 17A: shows a diagram illustrating TNF-a serum levels in mice 1 and 4 hours post-administration of 100 μg of LPS alone. Mice were either pre-treated with PBS or 50 μg of PSA three times every other day before LPS administration. * indicates statistical significance as determined by a students t test. SD was determined from the serum of individual mice. These data are representative of three independent experiments. FIG. 17B: shows a diagram illustrating IL-6 serum levels in mice 1 and 4 hours post-administration of 100 μg of LPS. Pre-treatment as in panel a * indicates statistical significance as determined by a students t test. SD was determined from the serum of individual mice. These data are representative of three independent experiments. FIG. 17C: shows a diagram illustrating variation of the spleen weight in untreated mice (con) and in mice administered LPS within the intraperiotenal cavity (LPS) and pre-treated with PBS or PSA as in panel a. Each dot represents the weight of the spleen from an individual mouse. P values were determined by a students T test. FIG. 17D: shows a diagram illustrating the survival rate of animals undergoing septic shock induced by high dose (500 μg) administration of LPS and pre-treated with PSA or PBS. N=12 mice in each group. FIG. 17E: shows a diagram illustrating the serum concentrations of TNF-a in mice post-administration of 500 μg of LPS alone or pre-treated with PSA or PBS. p values were determined by students T test. Each dot represents an individual mouse. FIG. 17F shows a diagram illustrating the serum concentrations of IL-6 in mice post-administration of 500 μg of LPS alone and pre-treated with PSA or PBS. p values were determined by students T test. Each dot represents an individual mouse.

FIG. 18A: shows a diagram illustrating TNF-a serum levels in mice pre-treated with PBS or PSA and administered LPS. Serum was collected 1 and 4 hours post-administration of LPS in IL-10$^{-/-}$ mice. * indicates statistical significance as determined by a students t test. SD was determined from the serum of individual mice. FIG. 18B: shows a diagram illustrating IL-6 serum level in mice pre-treated with PSA or PBS. Serum was collected 1 and 4 hours post-administration of LPS in IL-10$^{-/-}$ mice. * indicates statistical significance as determined by a students t test. SD was determined from the serum of individual mice FIG. 18C: shows a diagram illustrating percent survival in mice post-administration of LPS alone or together with PSA in IL-10 $^{-/-}$ mice. N=8 mice in each group.

DETAILED DESCRIPTION

Figure 2:
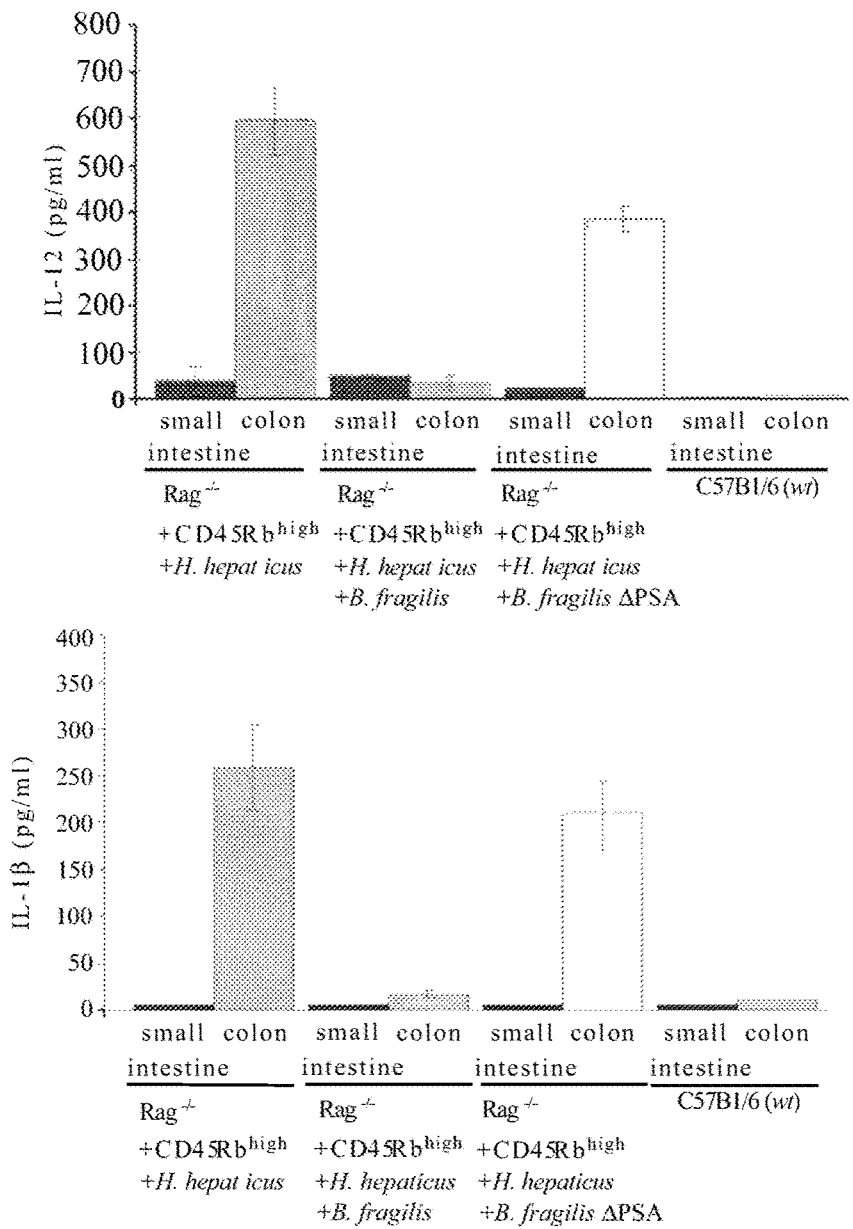
FIG. 2 shows an exemplary ZP mediated cytokine control according to some embodiments herein disclosed. In particular.

Methods and compositions are herein disclosed that allow balancing a T-helper cell profile in an individual, based on the use of PSA or another zwitterionic polysaccharide.

The term "T-helper" as used herein with reference to cells indicates a sub-group of lymphocytes (a type of white blood cell or leukocyte) including different cell types identifiable by a skilled person. In particular, T-helper cell according to the present disclosure include effector $T_h$ cells (such as Th1, Th2 and Th17)—i.e. Th cells that secrete cytokines, proteins or peptides that stimulate or interact with other leukocytes, including $T_h$ cells—and suppressor Th cells (such as Treg) i.e. Th cells that suppress activation of the immune system and thereby maintain immune system homeostasis and tolerance to self-antigens. Mature $T_h$ cells are believed to always express the surface protein CD4. T cells expressing CD4 are also known as CD4$^+$ T cells. CD4$^+$ T cells are generally treated as having a pre-defined role as helper T cells within the immune system, although there are known rare exceptions. For example, there are sub-groups of suppressor T cells, natural killer T cells, and cytotoxic T cells that are known to express CD4 (although cytotoxic examples have been observed in extremely low numbers in specific disease states, they are usually considered non-existent).

The term "cell profile as used herein indicates a detectable set of data portraying the characterizing features of a cell that distinguish the characterized cell from another. In particular, when referred to a T helper cell, the wording "cell profile" indicates a detectable set of data related to a marker cytokine that is produced by the Th cell and characterizes the Th cell with respect to another. For example, marker cytokine for Th1 cell is Interferon-g; marker cytokine for Th2 is IL-4, marker cytokine for Th7 is Tl-17 and marker cytokine for Treg is IL-10. Accordingly, the wording "Th17 cell profile" as used herein indicates the detectable set of data, such as presence and amount, related to production of IL-17 in a certain organ or tissue of the individual wherein the presence and/or activity of Th1 cell is investigated. Similar definitions apply to the other Th cell types. On the other hand, when the wording "cell profile" is referred to a subset of Th cell including more then one Th cell type, the wording "T-helper cell profile" indicates a detectable set of data related to each marker cytokine that is produced by and characterizes each, of the T-helper cells of the subset.

The term "balance" as used herein with reference to a "Th cell profile" as used herein indicates the activity of bringing the cell profile to a status associated with absence of an inflammatory response. Similarly the term "balanced Th profile" indicates the Th cell profile status associated with absence of an inflammatory response and in particular to the detectable set of data related to a marker cytokine that is produced by the T helper cell and characterizes the T helper cell with respect to another in absence of an inflammatory response. When the term "T-helper cell" profile refers to a subset of Th cell including more then one Th cell type, the term "balanced Th profile" refers instead to the relative ratio between the detectable set of data related to each marker cytokine that is produced by and characterizes each, of the T-helper cells. For example, a "balanced Th cell profile" referred to a Th cells subset comprising Th1, Th2 and Th17 indicates the relative ratio of data related to Interferon-gamma, IL-4 and IL17 associated with absence of an inflammatory response.

The term "zwitterionic polysaccharide" as used herein indicates synthetic or natural polymers comprising one or more monosaccharides joined together by glicosidic bonds, and including at least one positively charged moiety and at least one negatively charged moiety. Zwitterionic polysaccharides include but are not limited to polymers of any length, from a mono- or di-saccharide polymer to polymers including hundreds or thousands of monosaccharides. In some embodiments, a zwitterionic polysaccharide can include repeating units wherein each repeating unit includes from two to ten monosaccharides, a positively charged moiety (e.g. an free positively charged amino moiety) and a negatively charged moiety (such as sulfonate, sulfate, phosphate and phosphonate). In some embodiment ZPs can have a molecular weight comprised between 500 Da and 2,000,000 Da. In some embodiments, the ZPs can have a molecular weight comprised between 200 and 2500. Exemplary ZPS include but are not limited to PSA and PSB from *Bacteroides Fragilis*, CP5/CD8 from *Staphylococcus aureus*, and Sp1/CP1 from *Streptococcus pneumonia*. Zwitterionic polysaccharides can be isolated from natural sources, and in particular from bacterial sources, e.g. by purification. Zwitterionic polysaccharides can also be produced by chemical or biochemical methods, as well as by recombinant microorganism technologies all identifiable by a skilled person. Thus, those methods and technologies will not be further described herein in detail.

The wording "polysaccharide A" as used herein indicates a molecule produced by the PSA locus of *Bacteroides Fragilis* and derivatives thereof which include but are not limited to polymers of the repeating unit {→3)α-d-AAT-Galp(1→4)[β-d-Galf(1→3)]-d-GalpNAc(1  3)β-d-Galp (1→}, where AATGal is acetamido-amino-2,4,6-trideoxy-galactose, and the galactopyranosyl residue is modified by a pyruvate substituent spanning O-4 and O-6. The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining functional properties of the first polysaccharide. Accordingly, a derivative polysaccharide of PSA, usually differs from the original polysaccharide by modification of the repeating units or of the saccharidic component of one or more of the repeating units that might or might not be associated with an additional function not present in the original polysaccharide. A derivative polysaccharide of PSA retains however one or more functional activities that are herein described in connection with PSA in association with the anti-inflammatory activity of PSA.

In some embodiments, the zwitterionic polysaccharide can be PSA and/or PSB. In some embodiments, the effective amount of ZP and in particular PSA and/or PSB is from about 1-100 micrograms to about 25 grams of body weight and the T-helper cell profile is balanced by balancing at least one of Th1, Th2, Th17 and Treg, in particular at least one of Th1, Th 2 and Treg and Th17. More particularly, in some embodiments, balance Th cell profile can be performed by balancing the Th17 cell profile In some embodiments, a ZP can be used to control cytokine production associated with inflammation in an individual. In particular, in some embodiments, ZPs can be administered to inhibit production of pro-inflammatory cytokine molecules such as TNF-a, IL1 or IL-6, IL21, IL23 and IL17.

The term "control" as used herein indicates the activity of affecting and in particular inhibiting a biological reaction or process, which include but are not limited to biological and in particular biochemical events occurring in a biological system, such as an organism (e.g. animal, plant, fungus, or micro-organism) or a portion thereof (e.g. a cell, a tissue, an organ, an apparatus).

The terms "inhibiting" and "inhibit", as used herein indicate the activity of decreasing the biological reaction or process. Accordingly, a substance "inhibits" a certain biological reaction or process if it is capable of decreasing that biological reaction or process by interfering with said reaction or process. For example, a substance can inhibit a certain biological reaction or process by reducing or suppressing the activity of another substance (e.g. an enzyme) associated to the biological reaction or process, e.g. by binding, (in some cases specifically), said other substance. Inhibition of the biological reaction or process can be detected by detection of an analyte associated with the biological reaction or process. The term "detect" or "detection" as used herein indicates the determination of the existence, presence or fact of an analyte or related signal in a limited portion of space, including but not limited to a sample, a reaction mixture, a molecular complex and a substrate. A detection is "quantitative" when it refers, relates to, or involves the measurement of quantity or amount of the analyte or related signal (also referred as quantitation), which includes but is not limited to any analysis designed to determine the amounts or proportions of the analyte or related signal. A detection is "qualitative" when it refers, relates to, or involves identification of a quality or kind of the analyte or related signal in terms of relative abundance to another analyte or related signal, which is not quantified.

The term "cytokine" as used herein indicates a category of signaling proteins and glycoproteins extensively used in cellular communication that are produced by a wide variety of hematopoietic and non-hematopoietic cell types and can have autocrine, paracrine and endocrine effects, sometimes strongly dependent on the presence of other chemicals. The cytokine family consists mainly of smaller, water-soluble proteins and glycoproteins with a mass between 8 and 30 kDa. Cytokines are critical to the development and functioning of both the innate and adaptive immune response. They are often secreted by immune cells that have encountered a pathogen, thereby activating and recruiting further immune cells to increase the system's response to the pathogen.

Detection of inhibition of cytokine production can be performed by methods known to a skilled person including but not limited to ELISA, Q-PCR and intracellular cytokine staining detected by FACs and any other methods identifiable by a skilled person upon reading of the present disclosure.

In some embodiments, a ZP can be administered to inhibit production of at least one of TNF-a, IL-6, IL-17, IL-21 and IL-23. In particular, in some of those embodiments ZP can be administered systemically and in particular, orally, sub cutaneously, intra peritoneally, and intravenously. In some embodiments ZP can be administered in an amount between about 1 and about 100 micrograms/25 grams of body weight.

Methods and compositions are herein disclosed that allow control of an inflammation associated with an imbalanced Th cell profile and or to production of at least one of the pro-inflammatory cytokines IL-1, IL-6, TNF-a, IL-17, IL21, IL23, and TGF-β in an individual.

The term "inflammation" and "inflammatory response as used herein indicate the complex biological response of vascular tissues of an individual to harmful stimuli, such as pathogens, damaged cells, or irritants, and includes secretion of cytokines and more particularly of pro-inflammatory cytokine, i.e. cytokines which are produced predominantly by activated immune cells such as microglia and are involved in the amplification of inflammatory reactions. Exemplary pro-inflammatory cytokines include but are not limited to IL-1, IL-6, TNF-a, IL-17, IL21, IL23, and TGF-β. Exemplary inflammations include acute inflammation and chronic inflammation. The wording "acute inflammation" as used herein indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). The wording "chronic inflammation" as used herein indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. An inflammation can be controlled in the sense of the present disclosure by affecting and in particular inhibiting anyone of the events that form the complex biological response associated with an inflammation in an individual. In particular, in some embodiments, an inflammation can be controlled by affecting and in particular inhibiting cytokine production, and more particularly production of pro-inflammatory cytokines, following administration of a zwitterionic polysaccharide.

More particularly, in some embodiments, a ZP can be used to control an inflammation associated with IL-1, IL-6, TNF-a, IL-17, IL21, IL23, and/or TGF-β mediated inflammation in an individual. The wording "cytokine mediated inflammation" as used herein indicates an inflammation wherein the complex biological response to a harmful stimulus is controlled by cytokine molecules, such as pro-inflammatory cytokine molecules (e.g. TNF-a, IL1 and/or IL-6) and anti-inflammatory cytokine molecules (e.g. IL-10). Exemplary cytokine mediated inflammation include but are not limited to conditions mediated by IL-1, IL-6, TNF-α, IL-12p35, IL-17A, IL-21, IL-22, IFN-γ and/or IL-23p19.

In some embodiments, the cytokine is at least one of TNF-a, IL-17, IL-21, and IL-23 and the cytokine mediated inflammation is a IBD, asthma, type 1 diabetes, multiple sclerosis, obesity, type 2 diabetes, hay fever, food allergies, skin allergies, or rheumatoid arthritis. Reference is also made to Mazmanian et al 2008[43], in particular the figures and related portion of the paper herein incorporated by reference in its entirety.

In some embodiments, the inflammation is a systemic inflammation. Systemic inflammations include but are not limited to an inflammatory response in the circulatory system, an inflammatory response which is not confined in a specific organ, and an inflammatory response that extends to a plurality (up to all) tissues and organs in an individual.

In some embodiments, a ZP can be used to control an inflammation associated with an imbalance of T-helper cell profile and in particular to a Th17 cell profile, including but not limited to rheumatoid arthritis, respiratory diseases, allograft rejection, systemic lupus erythematosis, tumorgenesis, multiple sclerosis, systemic sclerosis and chronic inflammatory bowel disease.

In some embodiments, PSA can be administered systemically to the individual. The wording "systemic administration" as used herein indicates a route of administration by which PSA is brought in contact with the body of the individual, so that the desired effect is systemic (i.e. non limited to the specific tissue where the inflammation occurs). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

In some embodiments, administration is performed intravenously by introducing a liquid formulation including a ZP in a vein of an individual using intravenous access methods identifiable by a skilled person, including access through the skin into a peripheral vein. In some embodiments, administration of a ZP is performed intraperitoneally, by injecting a ZP in the peritoneum of an individual, and in particular of animals or humans. Intraperitoneal administration is generally preferred when large amounts of blood replacement fluids are needed, or when low blood pressure or other problems prevent the use of a suitable blood vessel for intravenous injection. In some embodiments administration is performed intragastrically, including administration through a feeding tube. In some embodiments, administration of a ZP is performed intracranially. In some embodiments a ZP can be administered topically by applying the ZP usually included in an appropriate formulation directly where its action is desired. Topical administration include but is not limited to epicutaneous administration, inhalational administration (e.g. in asthma medications), enema, eye drops (E.G. onto the conjunctiva), ear drops, intranasal route (e.g. decongestant nasal sprays), and vaginal administration.

In some embodiments, the inflammation is an inflammation of in a tissue and in particular in pancreas, lungs, joints, skin, brains and central nervous system, and eyes.

In some embodiments, PSA is used in a method of treating or preventing a condition associated with inflammation in an individual. The method comprises administering to the individual a therapeutically effective amount of the PSA. The term "individual" as used herein includes a single biological organism wherein inflammation can occur including but not limited to animals and in particular higher animals and in particular vertebrates such as mammals and in particular human beings.

The term "condition" as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated with an inflammation include but are not limited to inflammatory bowel disease, including but not limited to Chron's disease and ulcerative colitis, asthma, dermatitis, arthritis, myasthenia gravis, Grave's disease, sclerosis, psoriasis.

The term "treatment" as used herein indicates any activity that is part of a medical care for or deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

An effective amount and in particular a therapeutically effective amount of PSA is for example in the range of between about 1 µg to about 100 µg of PSA per 0.025 kilograms of body weight. In some embodiments, the effective amount is in a range from about 0.001 µg to about 1,000 µg per 0.25 kilograms of body weight.

In some embodiments, PSA is comprised in a composition together with a suitable vehicle. The term "vehicle" as used herein indicates any of various media acting usually as solvents, carriers, binders or diluents for PSA comprised in the composition as an active ingredient.

In some embodiments, where the composition is to be administered to an individual the composition can be a pharmaceutical anti-inflammatory composition, and comprises PSA and a pharmaceutically acceptable vehicle.

In some embodiments, PSA can be included in pharmaceutical compositions together with an excipient or diluent. In particular, in some embodiments, pharmaceutical compositions are disclosed which contain PSA, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb PSA. Suitable excipients also include any substance that can be used to bulk up formulations with PSA to allow for convenient and accurate dosage. In addition to their use in the single-dosage quantity, excipients can be used in the manufacturing process to aid in the handling of PSA. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In certain embodiments, compositions and, in particular, pharmaceutical compositions can be formulated for systemic administration, which includes enteral and parenteral administration.

Exemplary compositions for parenteral administration include but are not limited to sterile aqueous solutions, injectable solutions or suspensions including PSA. In some embodiments, a composition for parenteral administration can be prepared at the time of use by dissolving a powdered composition, previously prepared in lyophilized form, in a biologically compatible aqueous liquid (distilled water, physiological solution or other aqueous solution).

Exemplary compositions for enteral administration include but are not limited to a tablet, a capsule, drops, and suppositories.

The Examples section of the present disclosure illustrates examples of the compositions and methods herein described as well as the studies carried out by applicants in order to investigate the functional and physical interactions of PSA Further advantages and characteristics of the present disclosure will become more apparent hereinafter from the following detailed disclosure in the Examples given by way or illustration only with reference to an experimental section.

EXAMPLES

The methods and system herein disclosed are further illustrated in the following examples, which are provided by way of illustration and are not intended to be limiting.

In particular, in the following examples, the following materials and methods were used.

Bacterial strains and animals. *B. fragilis* NCTC9343 and *H. hepaticus* ATCC51149 were obtained from the American Type Culture Collection. Conventionally reared SPF mice of strains C57BL/6NTac, C57BL/6NTac IL-10$^{-/-}$, and B6.129S6-Rag2$^{tm1/Fwa}$ N12 (Rag2$^{-/-}$) were purchased from Taconic Farms (Germantown, N.Y.) and screened negative for *B. fragilis* and *H. hepaticus*. Swiss-Webster germ-free (SWGF) mice were purchased from Taconic Farms. Upon delivery in sterile shipping containers, the mice were transferred to sterile isolators (Class Biologically Clean, Madison, Wis.) in our animal facility. Animals were screened weekly for bacterial, viral, and fungal contamination as previously described[40]. All animals were cared for under established protocols and the IACUC guidelines of Harvard Medical School and the California Institute of Technology.

Model of inflammation: Three models of intestinal inflammation were used: 1) CD4$^+$CD45Rb$^{high}$ T cells were purified from the spleens of wild-type or IL-10$^{-/-}$ donor mice by flow cytometry and transferred into Rag$^{-/-}$ (C57Bl/6) recipients as described. 2) TNBS colitis was induced by pre-sensitization of wild-type (C57Bl/6) mice on the skin with a TNBS/acetone mix. Seven days after sensitization, 2.5% TNBS in ethanol was administered rectally; mice were sacrificed 3-6 days later. 3) IL10$^{-/-}$ mice were colonized (by oral gavage) with *H. hepaticus* alone or in combination with wild-type *B. fragilis* or *B. fragilis* ΔPSA.

Assays and scoring systems: Cytokines from the spleen, colons, or MLNs were assayed by ELISA, Q-PCR, or flow cytometry. Colitis was assessed with tissue sections (fixed, paraffin embedded, sectioned onto a slide, and stained with hematoxylin and eosin) and was scored by a blinded pathologist (Dr. R. T. Bronson, Harvard Medical School) according to a standard scoring system: 0, no thickening of colonic tissues and no inflammation (infiltration of lymphocytes); 1, mild thickening of tissues but no inflammation; 2, mild thickening of tissues and mild inflammation; 3, severe thickening and severe inflammation. BMDCs were purified from femurs of mice after extraction and washing in PBS. Cells were cultured for 8 days in C-RPMI-10 in the presence of GM-CSF (20 ng/mL; Biosource, Camarillo, Calif.). $CD4^+$ T cells were purified by negative selection over a magnetic column (Miltenyi or R& D Systems).

Flow cytometry, fluorescence-activated cell sorting (FACS), and staining. Lymphocytes were isolated from mouse spleens that were mechanically disrupted into single-cell preparations. Red blood cells were lysed, and splenocytes ($1 \times 10^6$) were incubated with various combinations of antibodies (BD Pharmingen, San Diego, Calif.) at 2 mg/mL for 30 min at 4° C. Cells were then washed and either fixed or used directly. For intracellular cytokine flow cytometry, samples were analyzed on a model FC500 cytometer (Beckman Coulter, Fullerton, Calif.) or a FacsCalibur (Becton Dickson), and data were analyzed with RXP Analysis Software (Beckman Coulter) or FlowJO. FACS was performed on a BD FACSAria, and cell purity was always >99%.

In vitro cytokine assays. For colon organ cultures, procedures were followed as previously reported[41]. For co-culture, $CD4^+$ T cells were purified from splenic lymphocytes (prepared as described above) with a $CD4^+$ T Cell Subset Kit (R&D Systems, Minneapolis, Minn.) used as instructed by the manufacturer. Cell purity was always >95%. BMDCs were purified from femurs of mice after extraction and washing in PBS. Cells were cultured for 8 days in C-RPMI-10 in the presence of GM-CSF (20 ng/mL; Biosource, Camarillo, Calif.). Medium was replaced after 4 days, and adherent cells were cultured for an additional 4 days, at which point nonadherent cells were recovered, washed, and used directly. Cells were >95% $CD11c^+$ at the time of use. Purified $CD4^-$ T cells ($1 \times 10^6$) were mixed with purified $CD11^+$ BMDCs ($1 \times 10^6$) in a 48-well plate and were incubated at 37° C. in an atmosphere containing 5% $CO_2$. Various stimuli were used, as described in Results. ELISA was performed with pre-coated plate kits (BD Pharmingen) according to the manufacturer's guidelines. In some assays, H. hepaticus, with or without wild-type B. fragilis or B. fragilis ΔPSA, was added at various concentrations.

Induction of experimental colitis. As assessed by PCR, $Rag2^{-/-}$ and control C57Bl/6 mice were negative for H. hepaticus colonization at the time of delivery. Splenic lymphocytes were harvested from wild-type donor mice, and $CD4^-CD45Rb^{high}$ cells were purified from lymphocyte populations by FACS as described above. Cells were washed with PBS, and $3 \times 10^5$ cells were injected intraperitoneally in a volume of 0.2 mL into recipient H. hepaticus—colonized $Rag2^{-/-}$ animals. For colonization experiments, both H. hepaticus ($1 \times 10^8$ organisms) and B. fragilis ($1 \times 10^8$ organisms) were introduced at the time of cell transfer. Throughout PSA treatment studies, animals received 50 µg of PSA by gavage 3 times per week. Animals were weighed throughout the experiment until sacrifice at 8 weeks.

Induction of intestinal inflammation-TNBS colitis. The backs of wild-type (C57BL/6) male mice were shaved, and pre-sensitization solution (150 µL; acetone with olive oil in a 4:1 ratio mixed with 5% TNBS in a 4:1 ratio) was slowly applied. Seven days after sensitization, mice were anesthetized with isofluorene and TNBS solution (100 µL; 1:1 5% TNBS with absolute ethanol) administered rectally through a 3.5F catheter (Instech Solomon; SIL-C35). Mice were analyzed 4-6 days after TNBS administration.

Histologic tissue analysis. Mouse tissues in Bouin's fixative (VWR, West Chester, Pa.) were embedded in paraffin, sectioned (6-µm slices), mounted onto slides, and stained with hematoxylin and eosin. Sections were evaluated in blinded fashion by a single pathologist (Dr. R. T. Bronson, Harvard Medical School).

Quantitative real-time PCR. RNA was extracted with Trizol per the manufacturer's instructions (Invitrogen). RNA (1 µg) was reverse transcribed into cDNA with an iScript cDNA synthesis kit (Bio-Rad). cDNA was diluted by addition of 60 µL of water, and a 2-µL volume of this solution was used for Q-PCR. Q-PCR was performed using IQ SYBR Green supermix (Bio-Rad) and primers were used at 0.2 µm. Q-PCR was performed on a Bio-Rad iCycler IQ5. Sequences of Q-PCR primers were as follows 5'-3': IL-23 (p19) F: AGC TAT GAA TCT ACT AAG AGA GGG ACA (SEQ ID NO: 5) R: GTC CTA GTA GGG AGG TGT GAA GTT G (SEQ ID NO: 6). IL-17A F: TTA AGG TTC TCT CCT CTG AA(SEQ ID NO: 7) R: TAG GGA GCT AAA TTA TCC AA. (SEQ ID NO: 8) TNFα F: ACG GCA TGG ATC TCA AAG AC (SEQ ID NO: 9) R: GTG GGT GAG GAG CAC GTA GT (SEQ ID NO: 10). IL-10 F: CTG GAC AAC ATA CTG CTA ACC G (SEQ ID NO: 11) R: GGG CAT CAC TTC TAC CAG GTA A(SEQ ID NO: 12) RORyT F: CCG CTG AGA GGG CTT CAC (SEQ ID NO: 13) R: TGC AGG AGT AGG CCA CAT TAC A (SEQ ID NO: 14) IL-21 F: ATC CTG AAC TTC TAT CAG CTC CAC (SEQ ID NO: 15) R: GCA TTT AGC TAT GTG CTT CTG TTT C (SEQ ID NO: 16) IL-27 F: CTG TTG CTG CTA CCC TTG CTT (SEQ ID NO: 17) R: CAC TCC TGG CAA TCG AGA TTC (SEQ ID NO: 18).

Example 1

PSA Balances the Th1/Th2 Profile of the Mammalian Immune System

The two subtypes of effector $CD4^+$ T cells, $T_H1$ and $T_H2$, are defined by expression of the cytokines interferon g (IFNg) and interleukin 4 (IL-4), respectively (Janeway et al., 2001). As shown above, PSA induces $CD4^+$ T cell expansion in B. fragilis-colonized mice and in vitro. To further characterize the effects of PSA-mediated T cell activation, we assessed cytokine profiles using purified cellular components. Co-culture of DCs and $CD4^+$ T cells in the presence of PSA yields dose-dependent up-expression of the $T_H1$ cytokine IFNg. The level of IFNg production associated with PSA is comparable to that associated with several known potent IFNg inducers (a-CD3, LPS, and staphylococcal enterotoxin A [SEA]) and requires both DCs and T cells. Specificity is evidenced by the lack of $T_H1$ cytokine production after NAc-PSA treatment.

$T_H1$ cytokine production suppresses $T_H2$ responses; conversely, $T_H2$ cytokine expression inhibits $T_H1$ responses. Normal immune responses require a controlled balance of these opposing signals. Examination of IL-4 expression in response to PSA treatment reveals no cytokine production by purified $CD4^+$ T cells. a-CD3 and the superantigen SEA are potent stimulators of both classes of cytokine. As $T_H2$ cytokine production is a "default pathway" in many systems (Kidd, 2003; Amsen et al. 2004)) and $T_H1$ cytokine production is antagonistic to $T_H2$ expression, the specific stimulation of IFNg by PSA in vitro may provide a mechanism for establishing commensal-mediated homeostasis of the host immune system by balancing $T_H1/T_H2$ responses.

Example 2

PSA Is Required for Appropriate CD4+ T-Helper Cytokine Production During Colonization A proper $T_H1/T_H2$ balance is critical for human and animal health; over- or underproduction of either response is associated with immunologic disorders. We investigated the effects of PSA on $T_H1/T_H2$ cytokine responses in colonized animals, again using germ-free mice. CD4+ T cells from mouse spleens were purified and tested by ELISA for cytokine production. Overproduction of the $T_H2$ cytokine IL-4 in spleens of germ-free mice compared with levels in conventional mice. This result is consistent with previous reports of the appreciably $T_H2$-skewed profile of mice devoid of bacterial contamination and reflects the human neonatal (precolonization) cytokine profile (Kirjavainen and Gibson, 1999; Prescott et al., 1998; Adkins, 2000; Kidd, 2003). This "default" $T_H2$-bias in the absence of bacterial colonization again highlights the profound contributions of the microflora to immune development and provides a model to test the effects of symbiotic bacteria on the establishment of appropriate host cytokine production.

Mice colonized with wild-type *B. fragilis* alone display a level of IL-4 production similar to that in conventional mice with a complex microflora; this similarity shows the organism's sufficiency to correct systemic immune defects. Moreover, mice colonized with *B. fragilis* DPSA produce TH2 cytokines at elevated levels similar to those in germ-free mice. Thus the expression of a single bacterial antigen allows *B. fragilis* to correct the IL-4 cytokine imbalance found in uncolonized animals.

Examination of IFNg production by purified splenic CD4+ T cells reveals that germ-free mice, which are $T_H2$-skewed, are deficient in production of this prototypical $T_H1$ marker when compared to conventional mice. Colonization with wild-type *B. fragilis* alone is sufficient to correct the defect in IFNg expression in germ-free mice, with levels nearly as high as those in conventional mice. Lack of PSA production by the *B. fragilis* mutant during colonization of germ-free mice results in low-level production of $T_H1$ cytokines. These results were corroborated by intracellular cytokine staining of splenic lymphocytes from each group, which confirms that IFNg production is attributable to CD4+ T cells. The production of IL-2, another $T_H1$ cytokine, by CD4+ T cells in gnotobiotic mice also requires PSA production data not shown) Together, these results demonstrate that intestinal colonization of germ-free mice by *B. fragilis* alone is sufficient to establish a proper systemic $T_H1/T_H2$ balance within the host—a fundamental aspect of the mammalian immune response required for health.

Example 3

PSA Suppresses Th-17 Induced Inflammation

Experimental colitis and human IBD result from an initial inflammatory response that—lacking repression—advances in an uncontrolled fashion and ultimately leads to intestinal pathology and disease. To elucidate how PSA affects these primary inflammatory responses, Applicants employed an animal model of chemically induced colonic inflammation. Rectal administration of trinitrobenzene sulphonic acid (TNBS) to wild-type mice mimics the initiation of colitis by eliciting inflammatory T cell responses. Disease was induced by administration of TNBS (or vehicle, as a negative control), and oral treatment of PSA was evaluated.

The results illustrated in FIG. 7 show that the intestinal immune response are beneficially modulated by PSA. In particular, the results illustrated in FIG. 7a show that TNBS-treated animals display weight loss that is statistically significant relative to figures for vehicle-treated and PSA-treated animals, although partial weight loss is observed in the PSA group (FIG. 7a). Histological analysis confirmed PSA protection of colonic tissues against the massive epithelial hyperplasia and loss of colonocyte organization seen after TNBS treatment (FIG. 7b). Studies have shown that pathogenic $T_H17$ cells, which produce IL-17, mediate the induction of experimental colitis[30]. Indeed, IL-17 levels are increased among purified CD4+ T cells from mesenteric lymph nodes (MLNs; FIG. 7c) of diseased animals but not from those of PSA-treated animals. The increased level of TNFa among CD4+ T cells from MLNs of TNBS-treated animals is also reduced in PSA-treated groups (FIG. 7d). Transcriptional analysis of TNBS-treated colons revealed that expression of both IL-17 and TNFa is highly elevated in diseased but not in PSA-protected animals (FIGS. 7e and 7f).

Therefore, the above results show that PSA inhibits intestinal pathology and inflammation in a chemically induced model of experimental colitis.

Example 4

PSA Induces the Differentiation of IL-10 Producing Treg to Suppress Inflammation Protection from experimental colitis is engendered through anti-inflammatory processes that prevent undesirable reactions against the intestinal microbiota[23]. Interleukin-10-deficient (IL-10$^{-/-}$) animals develop colitis[31]. IL-10, one of the most potent anti-inflammatory cytokines, is required for protection in many animal models of inflammation[21, 27, 32].

The results of a series of experiments directed to test the effect of PSA on IL-10 production are illustrated in FIG. 8, and show that PSA induces IL-10 expression in TNBS-treated animals and inhibits pro-inflammatory cytokine production in primary cultured cells through IL-10 production. In particular, as assayed by real-time PCR, transcriptional levels of IL-10 within colons of PSA-treated mice are significantly higher than those in control and TNBS-treated mice (FIG. 8a). IL-10 is produced by many cell types. However, since CD4+ T cells that express IL-10 display immunosuppressive activities that inhibit inflammation during experimental colitis[33], Applicants tested the IL-10 production in CD4+ T. When fresh CD4+ T cells were purified from MLNs of PSA-treated mice (in which inflammation is reduced), highly elevated levels of the IL-10 transcript were observed (FIG. 8b). Applicants then assessed whether PSA is sufficient to induce IL-10 in vitro; when bone marrow—derived dendritic cells (BMDCs) and naïve CD4+ T cells were treated with purified PSA, a specific increase in IL-10 production was observed (FIG. 8c).

Figure 9:
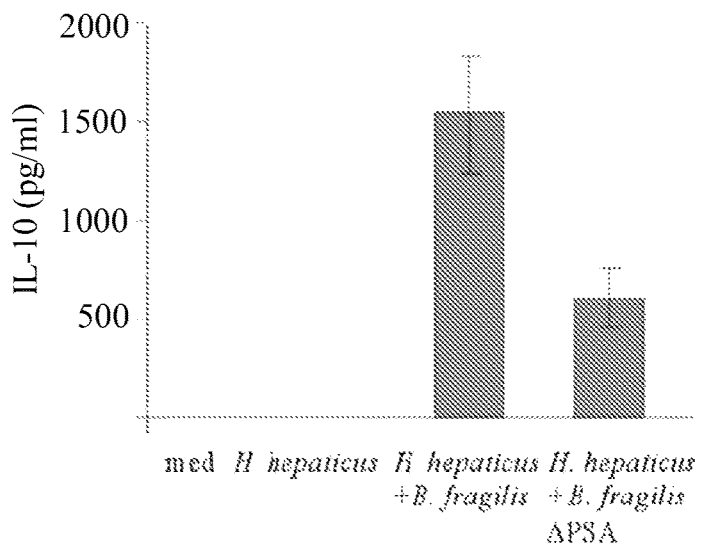
FIG. 9 shows a ZP mediated control of cytokine expression according to some embodiments herein disclosed. In particular.

A further series of experiments illustrated in FIG. 9, shows that PSA from *B. fragilis* induces expression of IL-10 in vitro. In particular, BMDCs and naïve CD4+ T cells were infected with *H. hepaticus* co-cultured with *B. fragilis*, and a specific expression of IL-10 from culture supernatants was observed; co-culture with *B. fragilis* DPSA induces significantly lower levels of IL-10 (FIG. 9). Since PSA induces expression of IL-10 in vitro, to test whether this molecule is required for inhibition of inflammatory responses to *H. hepaticus*, BMDC-T cell co-cultures were infected with live

*H. hepaticus* and measured expression of the critical pro-inflammatory cytokine TNFa. Addition of increasing concentrations of the pathogenic commensal causes a dose-dependent increase in TNFa production, as measured by ELISA of culture supernatants (FIG. 8d; left three bars). Treatment of cells with purified PSA markedly decreases TNFa production in response to *H. hepaticus* (FIG. 8d; middle three bars). Most importantly, co-incubation of cell cultures with *H. hepaticus* and PSA in the presence of a neutralizing IL-10 receptor antibody (aIL-10R) completely reverses this phenotypic effect and increases expression of TNFa (FIG. 8d; right three bars).

Figure 10:
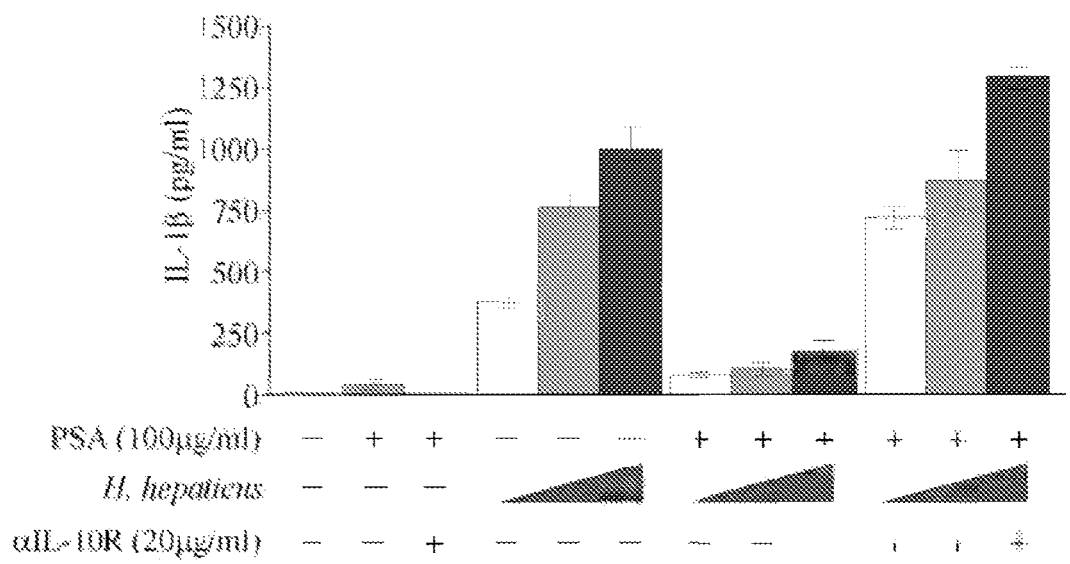
FIG. 10 shows a ZP mediated control of cytokine expression according to some embodiments herein disclosed. In particular.

The results are similar for the related pro-inflammatory cytokine IL-1b, as shown by the results of experiments illustrated in FIG. 10. In particular, infection of BMDC-T cell co-cultures with increasing concentrations of live *H. hepaticus* (see FIG. 10 multiplicity of infection: 0.1, 1.0, and 10, as depicted by triangles) results in release of the cytokine IL-1bTreatment of infected cells with PSA reduces IL-1blevels, as shown in the middle three bars. Neutralization of IL-10 signaling by addition of an IL-10 receptor antibody (aIL-10R) alleviates suppression of in vitro inflammatory responses, resulting in increased levels of IL-1b FIG. 10 left three bars.

Thus, the results illustrated in the present example support the conclusion that IL-10 produced in response to PSA is required for inhibition of inflammatory reactions in cell cultures.

Example 5

Figure 11A:
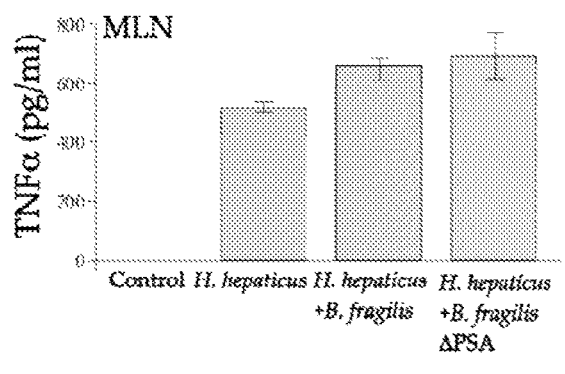
FIG. 11A-11F shows a ZP mediated protection from inflammation according to some embodiments herein disclosed.
Figure 11B:
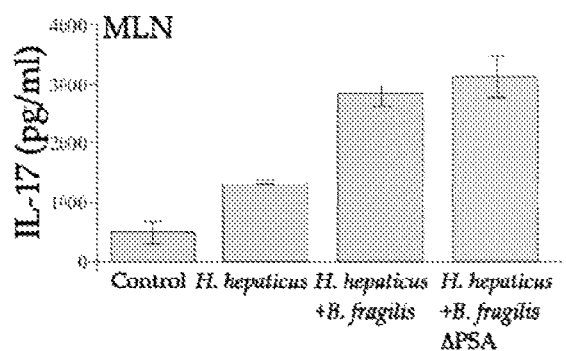
Figure 11C:
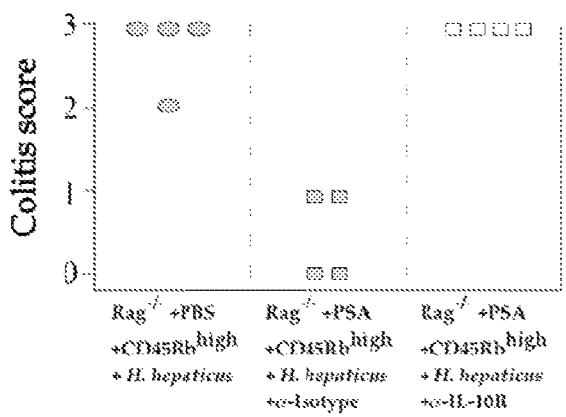

PSA Administration Results in Differentiation of Treg, Inhibition of TNF-a and IL-17 Cytokine Production and in Colitis Suppression Applicants investigated the requirement for IL-10 in suppression of intestinal inflammation. Initially, IL-10$^{-/-}$ animals were colonized with *H. hepaticus* alone or in combination with *B. fragilis* (wild-type or DPSA). Applicants subsequently harvested MLNs and re-stimulated cells in culture with soluble *Helicobacter* antigens in an assay previously developed to measure antigen-specific responses to *H. hepaticus*[27]. In particular, IL-10$^{-/-}$ mice were left uncolonized (control) or were colonized with *H. hepaticus* (to induce inflammation) either alone or in combination with *B. fragilis* (wild-type or APSA). MLNs from experimental groups were pooled and re-stimulated with soluble *Helicobacter* antigen (5 μg/ml) for 48 hours. Secretion of pro-inflammatory cytokines TNFα (a) and IL-17A (b) was analyzed by ELISA The results of these experiments, illustrated in FIGS. 11a-11c, show that *Helicobacter*—colonized animals display increased production of TNFa and IL-17; however, in the absence of IL-10 production in colonized animals, *B. fragilis* co-colonization dos not reduce levels of these pro-inflammatory molecules (FIGS. 11a and b, respectively). As expected, the absence of PSA has no effect. Using the cell transfer model of colitis (see Examples 6 to 8 below, Applicants transferred CD4$^+$CD45Rb$^{high}$ T cells to *Helicobacter-colonized Rag*$^{-/-}$ animals. Administration of aIL-10R to mice (to block IL-10 signaling) during oral treatment with PSA abrogates protection from colitis (FIG. 11c). In particular, colitis scores show that PSA protection requires aIL-10 signaling, as neutralizing antibodies to IL-10 block PSA's suppressive activity. Treatment with IL-10R abrogates PSA-mediated protection. (FIG. 11c).

Figure 12:
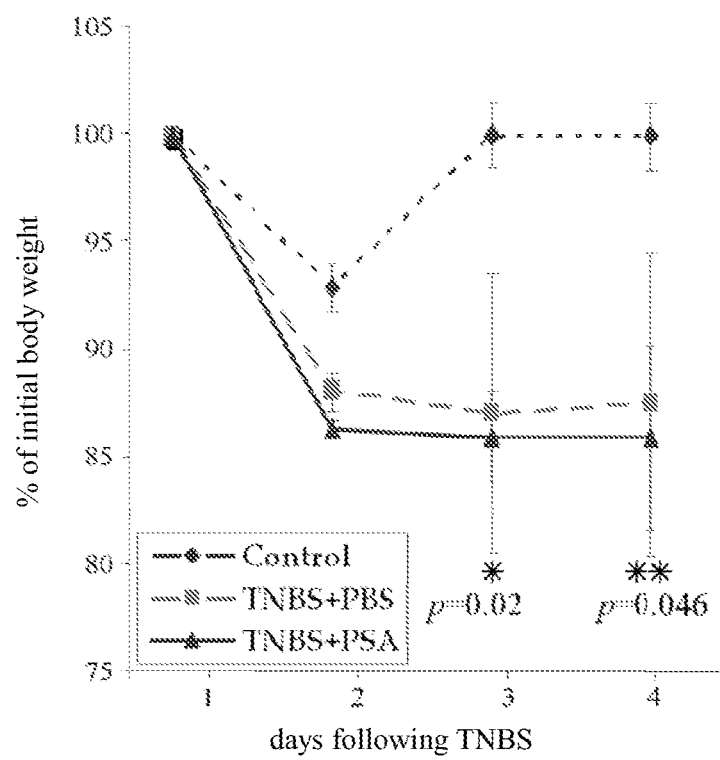
FIG. 12 shows effect of a ZP administration supporting embodiments herein disclosed. In particular.
Figure 13:
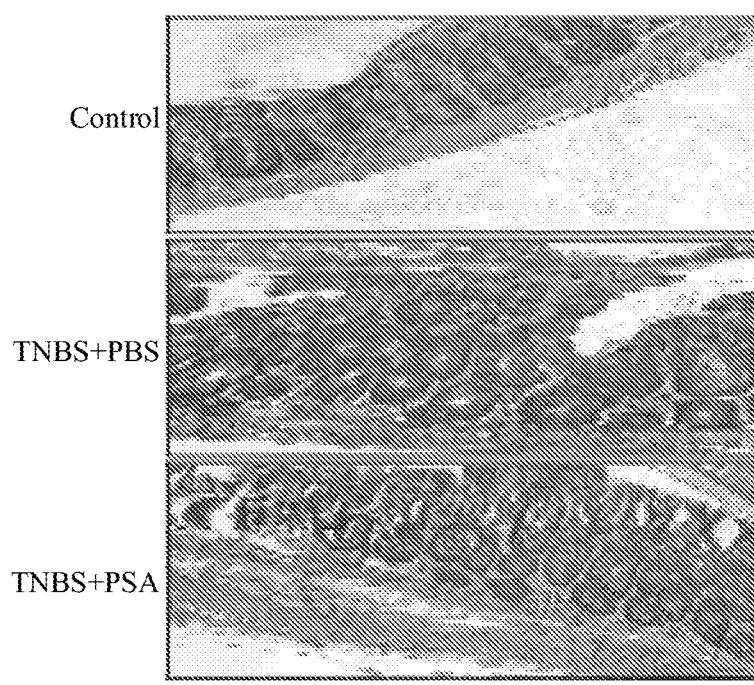
FIG. 13 shows effects of a ZP administration supporting some embodiments herein disclosed. In particular.

Additionally, when IL-10$^{-/-}$ animals were treated with TNBS in the presence or absence of PSA, weight and histology data illustrated in FIGS. 12 and 13, indicated that IL-10 production is required for PSA-elicited reduction of intestinal immune responses. In particular, in a first series of experiments, groups of 4 C57BL/6 mice were treated with PSA (or PBS) and then subjected to rectal administration of TNBS or vehicle (control). SD values illustrated in FIG. 12, indicate that, in the absence of IL-10, PSA cannot restore TNBS-induced weight loss. ANOVA demonstrates that weight loss in both TNBS-treated groups is statistically different from that in control animals and that PSA does not prevent weight loss in TNBS-treated IL-10$^{-/-}$ animals (FIG. 12).

In a second series of experiments, groups of 4 C57BL/6 mice were treated with PSA (or PBS) and then subjected to rectal administration of TNBS or vehicle (control). Histologic analysis of H&E-stained sections from a representative animal from each group is shown in FIG. 13. Thickening of the colon and epithelial hyperplasia are noted in both TNBS-treated groups of IL-10$^{-/-}$ animals, regardless of PSA treatment. Thus, the results illustrated in FIG. 13 show that in the absence of IL-10, PSA does not reduce intestinal injury in TNBS-treated IL-10$^{-/-}$ mice.

The above data suggest that PSA-mediated protection entails the generation and/or expansion of IL-10-producing CD4$^+$ T cells. To determine whether IL-10 production by CD4$^+$ T cells is required for protection, Applicants transferred CD4$^+$CD45Rb$^{high}$ T cells from IL-10$^{-/-}$ donor mice into Rag$^{-/-}$ recipients and then colonized the recipients with *H. hepaticus*.

Figure 11D:
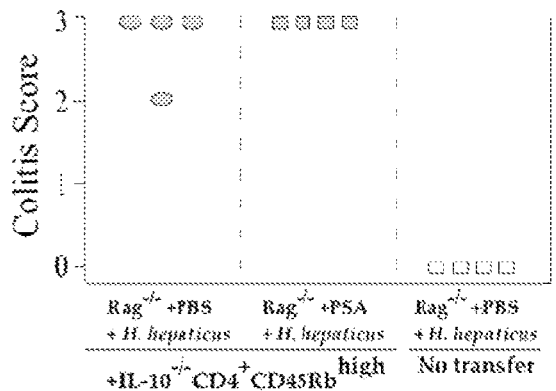
Figure 11E:
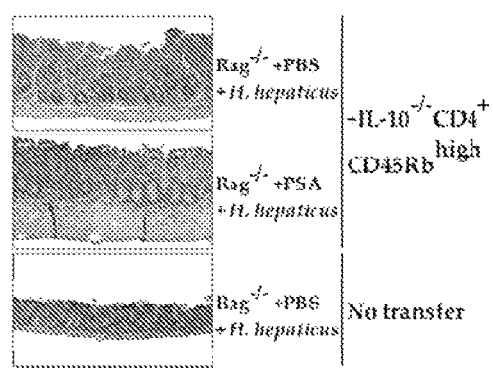
Figure 11F:
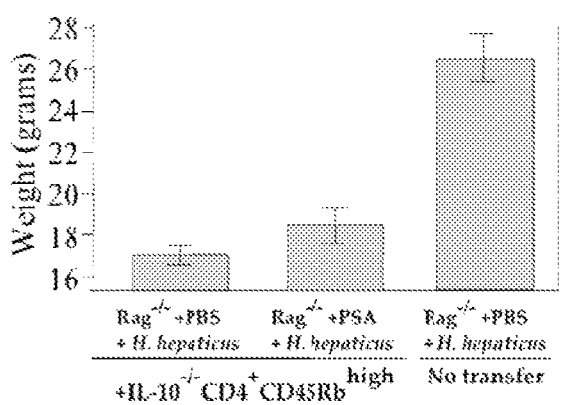

The results illustrated in FIGS. 11d-11f show that, as expected, groups of mice receiving IL-10$^{-/-}$ T cells along with *H. hepaticus* develop severe colitis (FIG. 11d; left bar) and are not protected by PSA (FIG. 11d; middle bar). This result, supported by histological findings in colons, indicates that PSA induces protection from "previously pathogenic" CD4$^+$CD45Rb$^{high}$ T cells in an IL-10-dependent manner (FIG. 11e). Weight analysis at sacrifice shows that colitic PBS- and PSA-treated animals receiving IL-10$^{-/-}$ CD4$^+$CD45Rb$^{high}$ T cells (unlike control animals receiving no transferred cells) develop wasting disease (FIG. 11f). Thus, IL-10 production by CD4$^+$ T cells is required for PSA-mediated protection from experimental colitis. These results constitute the first reported evidence of a symbiotic bacterial molecule that networks with the immune system to coordinate anti-inflammatory responses required for mammalian health.

Example 6

PSA Balances the CD4$^+$CD45Rb$^{high}$/CD4$^+$CD45Rb$^{low}$ T Cells Ratio

CD4$^+$ T cells of the mammalian immune system can be generally divided into a naïve ('uneducated') CD4$^+$CD45Rb$^{high}$ population and an antigen-experienced ('educated') CD4$^+$CD45Rb$^{low}$ population[16].

In a first series of experiments, mono-association of germ-free mice with wild-type *B. fragilis* was performed to analyze the effect on the CD4$^+$CD45Rb$^{low}$ T cells v. CD4$^+$CD45Rb$^{high}$ proportion. In particular, the ability of *B. fragilis* to correct deficiencies in the CD4$^+$CD45Rb$^{low}$ T cell population in spleen.

The results illustrated in FIG. 1a show that association of *B. fragilis* expands the proportions of CD4$^+$CD45Rb$^{low}$ T cells in a PSA-dependent manner Remarkably, Applicants found that splenic cells from germ-free animals include a smaller proportion of CD4+CD45Rb$^{low}$ T cells than do those from age-matched conventional mice with a complete bacterial microbiota (FIG. 1a). Additionally, it appears that mono-colonization of germ-free mice with wild-type B. fragilis alone restores the CD4+CD45Rb profile in animals with a complete bacterial microbiota (FIG. 1a; left panels). Most notably, colonization with a mutant strain defective in the ability to produce PSA (B. fragilis DPSA) does not generate an expansion of the CD4+CD45Rb$^{low}$ T cell population (FIG. 1a; lower right). It is well established that the latter population possesses potent anti-inflammatory properties and confers protection in animal models of inflammation[17]. These results suggested that PSA mediate protection from inflammation.

Example 7

PSA Controls IL23, IL1b and TNF-a Production in Inflamed Tissues, Thus Controlling Th17 and Th1-Mediated Cytokine Production The well-established CD4+CD45Rb transfer model of experimental colitis[18] was employed to investigate whether B. fragilis colonization protects animals from inflammatory disease. In this model, pathogenic CD4-CD45Rb$^{high}$ T cells are separated from protective CD4+CD45Rb$^{low}$ cells and transferred into specific pathogenfree (SPF) Rag$^{-/-}$ mice. Upon cell transfer, mice are colonized with Helicobacter hepaticus[8,9], a pathobiont that is a benign commensal in wild-type animals but an opportunistic pathogen causing colitis in immunocompromised mice. After 8 weeks, animals are sacrificed and colitis is assessed with a standard scoring system[20].

The pathology scores illustrated in FIG. 1b, show that H. hepaticus colonization and CD4+CD45Rb$^{high}$ T cell transfer are sufficient to induce severe colitis in Rag$^{-/-}$ mice (FIG. 1b; first column), as previously reported[19,21]. Co-colonization with wild-type B. fragilis results in significant protection from disease (FIG. 1b; second column), whereas co-colonization with B. fragilis DPSA does not (FIG. 1b; third column).

Tissue damage in colitis is widely believed to result from production of inflammatory cytokines in response to commensal bacteria[22]. The pro-inflammatory cytokines tumor necrosis factor a (TNFa, interleukin-1b (IL-1b and IL-23 are central to disease initiation and progression in this experimental model of colitis[23]. Furthermore, levels of these cytokines are elevated in patients with IBD[24], and therapies neutralizing TNFa have yielded promising results in clinical trials in patients with Crohn's disease[25]. Accordingly, Applicants decided to test the inflammatory cytokine levels during disease by directly culturing intestinal tissues of T cell recipient colonized animals[26]. The results illustrated in FIGS. 1c, 1d, 2 and 3 show that PSA alters cytokine levels in affected tissue.

In particular, the results of ELISA experiments of colon organ cultures illustrated in FIG. 1c show an increased expression of pro-inflammatory cytokine TNFa in diseased colons, with significant reductions in animals co-colonized with wild-type B. fragilis but not with B. fragilis DPSA.

The results of Q-PCR for IL-23p19 performed on splenocytes, normalized to L32 expression illustrated in FIG. 1d show that increases in IL-23 production by splenocytes following disease induction are completely suppressed by intestinal colonization with PSA-producing B. fragilis.

ELISA results for the pro-inflammatory cytokines IL-12p40 and IL-1b in colon and small intestines shown in FIG. 2 show a specific increase in pro-inflammatory cytokines in diseased colons but not in small intestines. This increase is significantly reduced in animals co-colonized with PSA-producing B. fragilis. Conversely, animals colonized with B. fragilis DPSA express greatly increased pro-inflammatory cytokine levels over those in control animals (C57BL/6) (FIG. 2).

Figure 3:
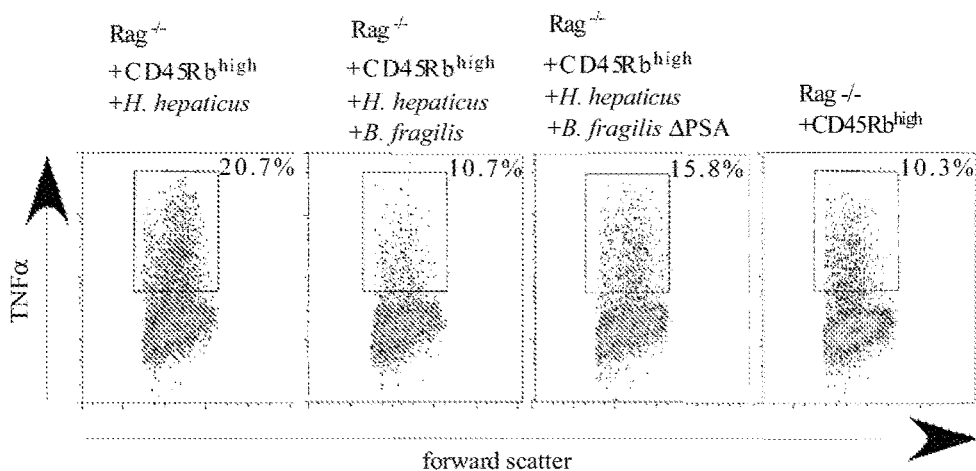
FIG. 3 shows an example of ZP mediated control of TNFa expression by $CD4^+$ T cells according to some embodiments herein disclosed. In particular FIG. 3 $CD4^+$ cells were purified from pooled splenocytes from each group (4 mice per group) and restimulated in vitro with PMA and ionomycin in the presence of brefeldin A for 4 hours. Cells were stained for intracellular TNFa. Cells within the lymphocyte gate were included in the analysis, and numbers indicate the percentage of cells producing TNFa. Purified cells were >90% $CD4^+$. Animals colonized with PSA-producing B. fragilis during protection displayed lower TNFa levels than diseased animals.

The results of experiments illustrated in FIG. 3 show that the expression of the TNFa by CD4- T cells is reduced by wild-type B. fragilis colonization during experimental colitis. CD4+ cells were purified from pooled splenocytes from each group (4 mice per group) and restimulated in vitro with PMA and ionomycin in the presence of brefeldin A for 4 hours. Cells were stained for intracellular TNFα. Cells within the lymphocyte gate were included in the analysis, and numbers indicate the percentage of cells producing TNFa. Purified cells were >90% CD4-. Animals colonized with PSA-producing B. fragilis during protection displayed lower TNFa levels than diseased animals.

Overall these above results show that PSA performs its effect by altering cytokine levels in affected tissues. In particular, levels of the pro-inflammatory cytokines TNFa (FIG. 1c), IL-12p40, and IL-1b (FIG. 2) are elevated in the colons of Rag$^{-/-}$ recipient mice colonized with H. hepaticus but not in sections of small intestine (a site not affected in this model). Consistent with the protection observed by pathophysiologic analysis of experimental colitis, TNFa levels are not elevated when these animals are co-colonized with wild-type B. fragilis. T cell transfer plus co-colonization with H. hepaticus and B. fragilis DPSA results in increased colonic cytokine production similar to that seen in Rag$^{-/-}$ animals colonized with H. hepaticus alone. Moreover, purified splenic CD4+ T cells from H. hepaticus—colonized animals, display increased TNFa production; this condition is corrected by colonization with wild-type B. fragilis but not with the PSA deletion strain (FIG. 3). Expression of IL-23 is critical in the cascade of events leading to experimental colitis[27,28]. Applicants found that increases in IL-23 production by splenocytes following disease induction are completely suppressed by intestinal colonization with PSA-producing B. fragilis (FIG. 1d).

Experiments directed to rule out bacterial clearance were performed to show whether, over the course of the experiments, levels of H. hepaticus and B. fragilis colonization did differ between groups. The results illustrated in FIGS. 4 and 5 show that protection is not the result of bacterial clearance.

In particular, the results shown in FIG. 4 show that experimental animals remain colonized with H. hepaticus and B. fragilis throughout the course of disease. More particularly, the ethidium bromide—stained gel electrophoresis of H. hepaticus—specific Q-PCR of FIG. 4a shows that co-colonization with B. fragilis does not induce clearance of bacteria after 8 weeks. The primers used for H. hepaticus 16S rDNA were: (HB-15) 5'-GAAACTGTTACTCTG-3' (SEQ ID NO: 1) and (HB-17) 5'-TCAAGCTCCCCGAAGGG-3'(SEQ ID NO: 2). Ethidium bromide—stained gel electrophoresis of B. fragilis—specific Q-PCR of FIG. 4b show stable bacterial colonization after 8 weeks; the primers used for B. fragilis ssr3 (finB) gene were: (ssr3-F) 5'-TATTTGCGAGAAGGTGAT-3' (SEQ ID NO: 3) and (ssr3-r) 5'-TAAACGCTTTGCTGC-TAT-3' (SEQ ID NO: 4).

In an additional series of experiments, quantitation of H. hepaticus was performed to verify whether PSA administration affected the presence of the organism. The results of quantitation of *H. hepaticus* colonization experiments of FIG. 5 demonstrate that the organism is present in equal numbers regardless of PSA-mediated protection. In particular, in the experiments of FIG. 5 fecal samples were collected from each experimental group, and total DNA was extracted (Qiagen DNAeasy tissue kit). Equal amounts of DNA (50 ng) were used in Q-PCR (Bio-rad) with *H. hepaticus*—specific primers. Q-PCR for *H. hepaticus* colonization was assessed according to Young et al., 2004[1] as $log^{10}$ number of copies of a known gene (cytolethal distending toxin). Animals contained equivalent levels of *H. hepaticus* at the end of the experiment.

The results illustrated in this example support the conclusion that PSA is a specific immunomodulatory molecule that orchestrates beneficial immune responses to prevent *B. Fragilis* host from developing experimental colitis.

Example 8

PSA Suppresses Inflammation Associated with $CD4^+CD45Rb^{high}$ T Cells

To determine whether PSA is sufficient for protection in the absence of the intact *B. fragilis* organism, Applicants purified PSA to homogeneity[29] and administered it by gavage (orally) to $Rag^{-/-}$ mice. Disease progression was then measured by various pathologic and histologic criteria.

The results of related experiments illustrated in FIG. 6, show that purified PSA orally administered protects against experimental colitis.

Figure 6A:
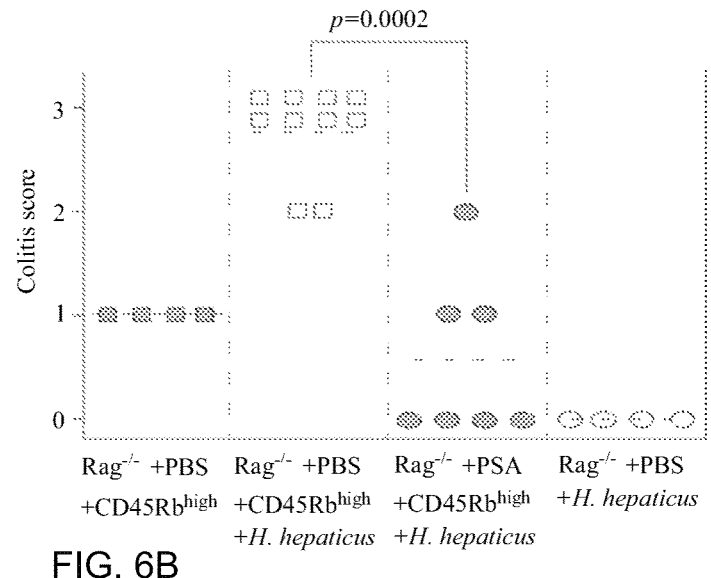
FIG. 6A-6C shows a ZPs mediated protection according to some embodiments herein disclosed.

In particular, in a first series of experiments illustrated in FIG. 6a, colitis scores after $CD4^+CD45Rb^{high}$ T cell transfer in the absence of *H. hepaticus* colonization indicated the development of very mild colitis due to inflammation elicited by the animals' SPF microbiota (FIG. 6a; first column). However, *Helicobacter*-colonized $Rag^{-/-}$ animals that receive $CD4^+CD45Rb^{high}$ T cell transfers develop severe colitis (FIG. 6a; second column). Oral PSA administration almost completely protects animals against *H. hepaticus*—induced colitis (FIG. 6a; third column), reducing disease to levels of control animals without T cell transfer, that known not to develop colitis (FIG. 6a; fourth column).

Figure 6B:
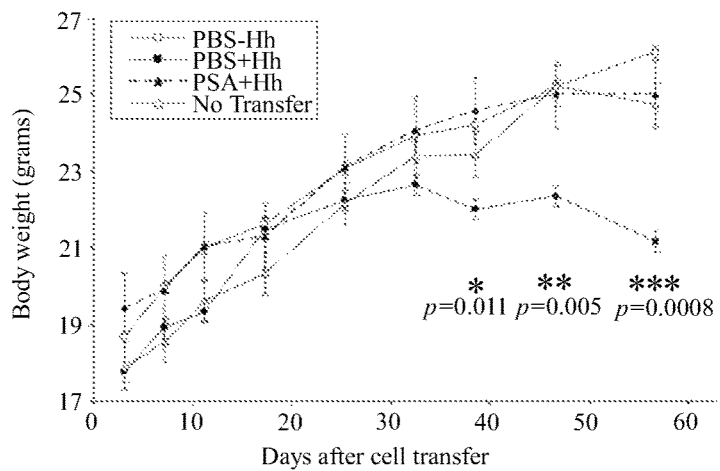

A second set of experiments was then performed to test the inability to gain weight, a hallmark of colitis in this experimental setting[4]. In particular, transfer of $CD4^+CD45Rb^{high}$ T cells and colonization with *H. hepaticus* (PBS+Hh) in $Rag2^{-/-}$ animals was performed and the animals were subsequently tested for wasting disease. The results illustrated in FIG. 6b show that wasting disease in $Rag^{-/-}$ animals follows transfer of $CD4^+CD45Rb^{high}$ cells and colonization with *H. hepaticus* (FIG. 6b; PBS+Hh). These animals also develop intestinal pathology and express pro-inflammatory cytokines (as described above). Oral administration of PSA from the outset completely protects animals against *H. hepaticus*—mediated wasting disease (PSA+Hh). *H. hepaticus* provides the necessary antigens for inflammation induction; no pathology is observed in uncolonized animals (PBS–Hh) or in animals without cell transfer. Therefore these experiments show that oral administration of PSA protects animals against wasting (PSA+Hh).

Figure 6C:
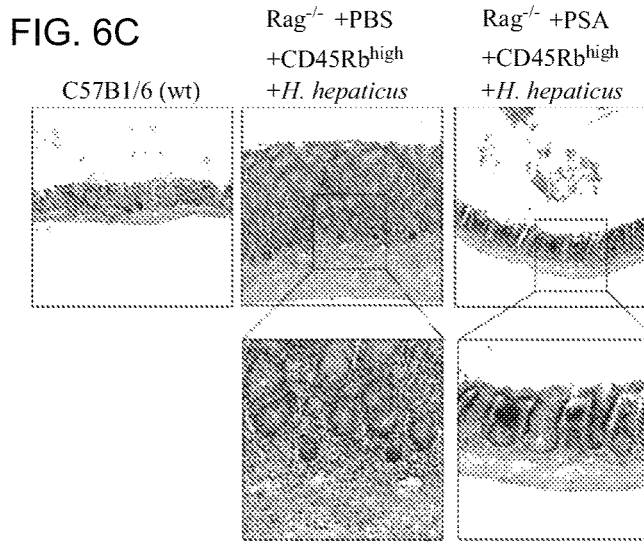
Figure 7A:
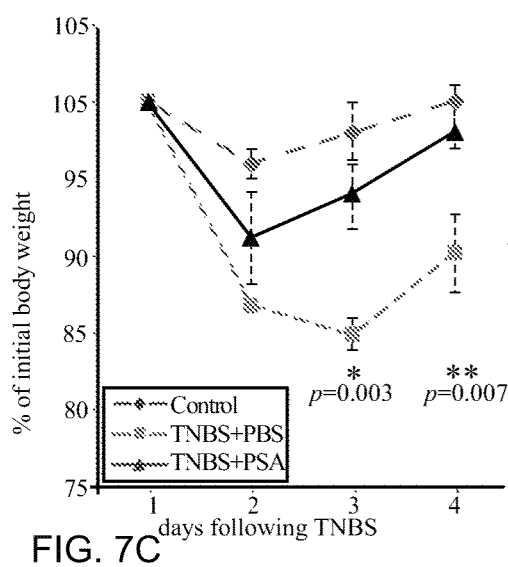
FIG. 7A-7F shows a ZP modulated immune response according to some embodiments herein disclosed.
Figure 7B:
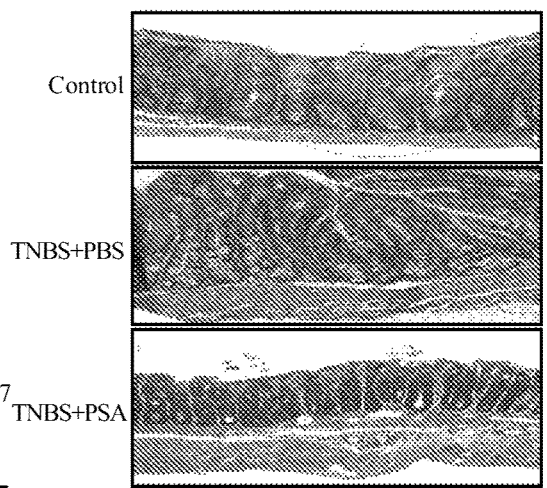
Figure 7C:
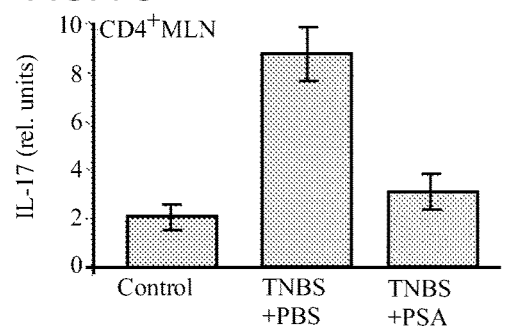
Figure 7D:
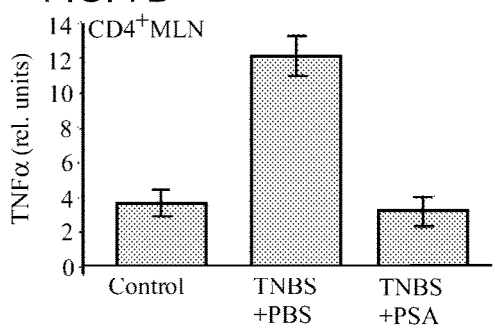
Figure 7E:
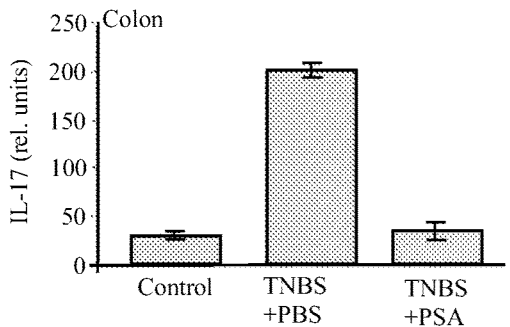
Figure 7F:
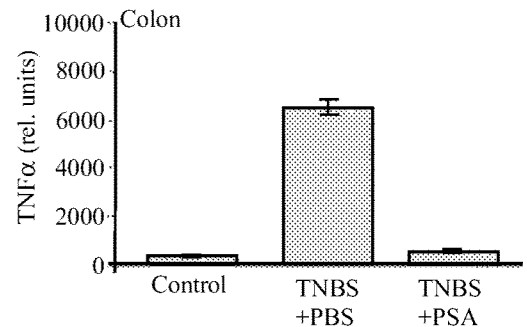

In a further set of experiments, histologic sections of colons of wild-type animals and animals subjected to transfer of $CD4^+CD45Rb^{high}$ T cells and colonization with *H. hepaticus* (PBS+Hh) were examined to verify the presence of inflammation resulting in experimental colitis. The results illustrated in FIG. 6c show that transfer of $CD4^+CD45Rb^{high}$ T cells into *Helicobacter*-colonized $Rag^{-/-}$ mice results in onset of severe colitis, as evidenced by massive epithelial cell hyperplasia and gross thickening of the gut wall (FIG. 6c; second panel). Furthermore, consistent with previous studies, the combination of $CD4^-CD45Rb^{high}$ T cell transfer plus *H. hepaticus* colonization results in infiltration of affected tissues by leukocytes—a hallmark of inflammation and disease (FIG. 6c second panel, bottom)[19, 21]. Additionally, oral administration of PSA to *H. hepaticus*—colonized cell transfer recipients confers complete protection against experimentally induced colonic hyperplasia (FIG. 6c; third panel); furthermore, PSA-treated animals display no leukocyte infiltration in colonic tissues (FIG. 6c third panel, bottom)—a result indicating protection against inflammation.

Taken together, these results indicate that oral administration of PSA prevents colitis and protects mice against the associated weight loss and inflammatory cell infiltration observed in diseased animals.

Example 9

Figure 14A:
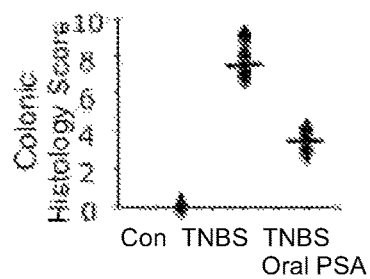
FIG. 14A-14D shows inhibition of inflammation within extra-intestinal immune compartments following oral administration of ZPS according to some embodiments herein disclosed. In particular.

PSA is Effective in Systemic Immune Compartments Suppressing Cytokine Production by Th1 and Th17 Cells In further series of experiments, mice were treated with TNBS or TNB/PSA, orally administered to the mice. The relevant colonic sections were subsequently analyzed by a blinded pathologist who provided a histological score. The results illustrated in FIG. 14a provide further evidence that oral PSA administration reduces colitis.

While oral treatment with purified PSA protects from experimental colitis (FIG. 14a), colonization by a *B. fragilis* mutant that does not make PSA (*B. fragilis*ΔPSA) is unable to protect. During the course of the experiments exemplified in Examples 1 to 8, Applicants noted strong effects of PSA in systemic immune compartments. To further understand these systemic responses Applicants utilized the TNBS induced model in the susceptible Balb/c mouse strain. As this model allows for disease induction in an immune-competent animal, it permits analysis of all immune cells involved in both disease induction and protection.

Balb/c mice were orally administered purified PSA before induction of colitis. Indeed, oral treatment of PSA protected from weight loss associated with experimental colitis and inflammation within the intestine (not shown).

Figure 14B:
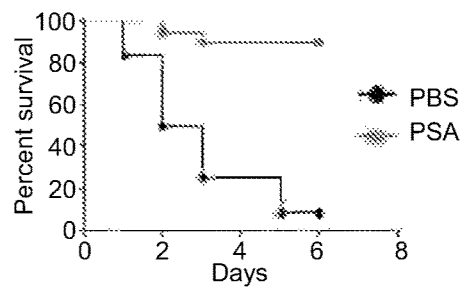
Figure 14C:
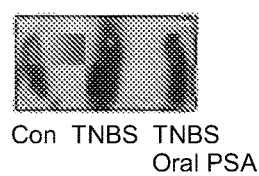
Figure 14D:
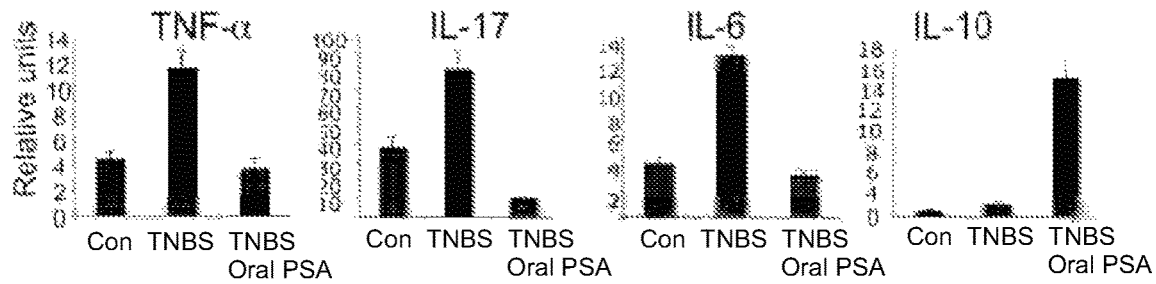

Additionally, pre-treatment of Balb/c mice undergoing TNBS induced colitis, with PSA dramatically increases the survival of animals with disease from 40% to 90%, (see FIG. 14b), further attesting to the powerful anti-inflammatory effects of PSA. Since splenomegaly is commonly seen in this model of IBD and demonstrates the systemic nature of this disease, the Applicants analyzed the spleen of mice treated with TNBS, and TNBS/PSA. The results illustrated in FIG. 14c show that oral administration of ZPS is protects from the splenomegaly. Furthermore, analysis of cytokine expression showed that animals undergoing TNBS induced colitis have severe splenomegaly with increases in the expression of inflammatory cytokines from CD4+ T lymphocytes residing within the spleen, as illustrated in FIG. 14d. Orally administered PSA significantly reduces splenomegaly and the expression of TNF-α, IL-17 and IL-21 in CD4+ T lymphocytes from the spleen during mucosal disease (FIG. 14d). The experiments outlined in Example 5 demonstrate that PSA is able to protect from colitis through induction of IL-10 from CD4+ T cells residing within the intestinal compartments. Consistent with previous data, Applicants find that IL-10 levels are elevated within the CD4+ T lymphocytes in spleen (FIG. 14d). Taken together, these data suggest that PSA residing within the intestine is capable of effecting systemic immunity. In particular these results show that oral administration of ZPS can not only protect from intestinal disease but also suppresses inflammation within extra-intestinal immune compartments, such as the spleen.

Example 10

Parenteral Administration of PSA Protects from Inflammation and Controls TNF-a, IL-17 and IL23 Production in Intestine and Spleen Distinct subsets of cells reside within the intestinal compartment, including CD8αα T cells, mucosal γδ T cells and CD103+ dendritic cells. Recent studies have demonstrated that these various cell types have distinct functions from their systemic immune counterparts. To determine whether PSA acts specifically within the intestine, purified PSA was administered intravenously and mucosal inflammation was induced. In a first series of experiments illustrated in FIG. 15, PSA was administered before inflammation was induced. In a second series of experiments, illustrated in FIG. 16, PSA was administered after inflammation was induced.

Figure 15A:
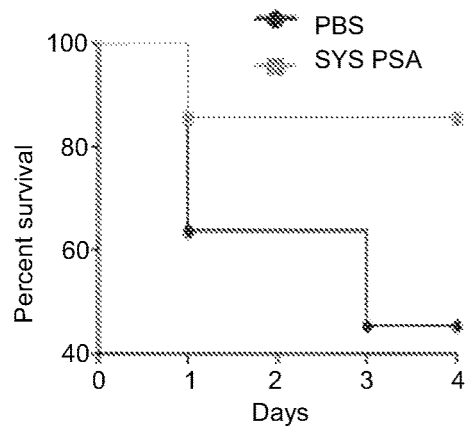
FIG. 15A-15B shows protection from TNBS induced intestinal colitis following administration of ZPS to extra-intestinal sites according to some embodiments herein disclosed. In particular.
Figure 15B:
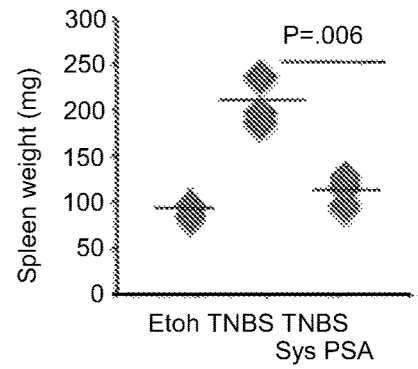
Figure 16A:
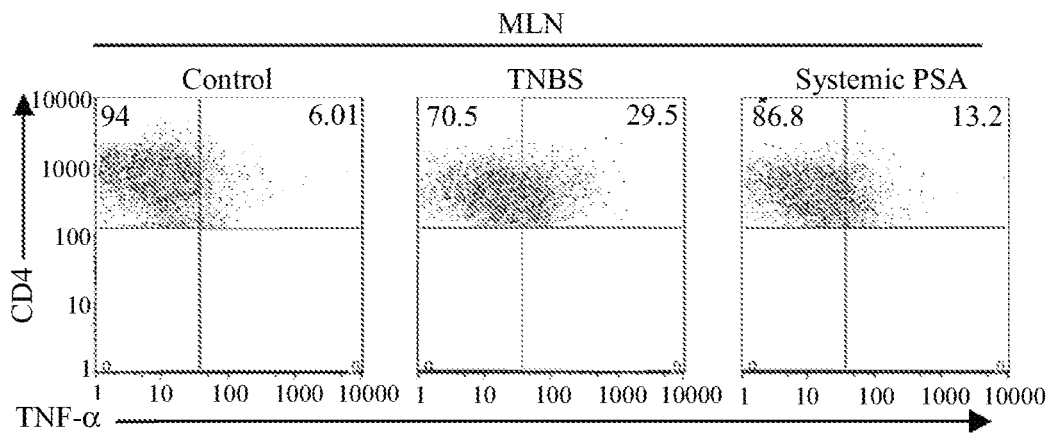
FIG. 16A-16D shows inhibition of inflammatory cytokines at both intestinal and systemic immune compartments following systemic administration of ZPS during TNBS induced colitis according to some embodiments herein disclosed.
Figure 16B:
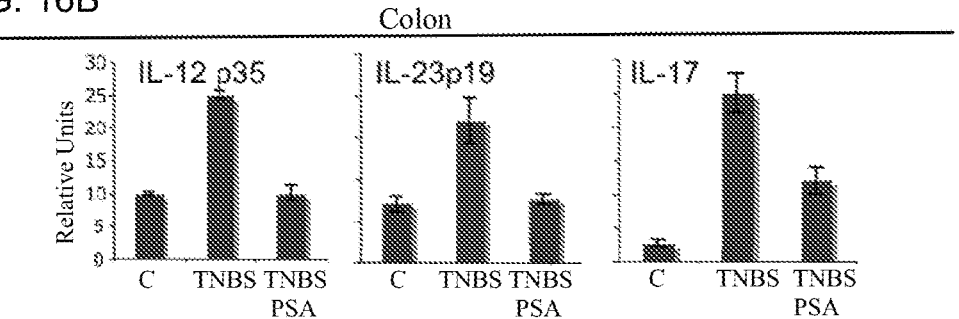
Figure 16C:
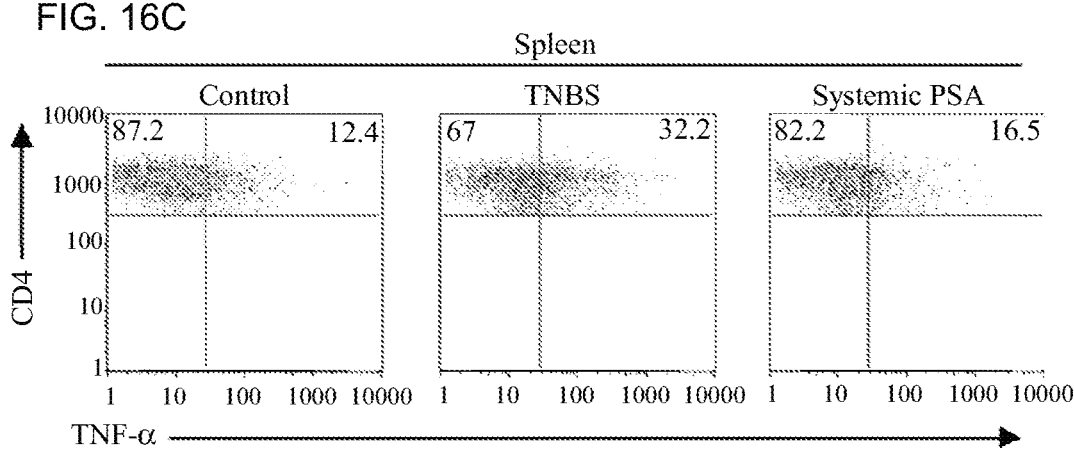
Figure 16D:
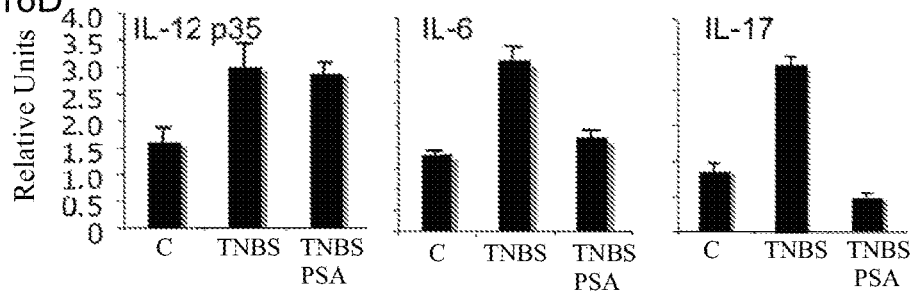

The results illustrated in FIG. 15, show that delivery of ZPS to extra-intestinal sites is able to protect from induced intestinal colitis. In particular, systemic administration of PSA enhances the survival of diseased animals and protects from splenomegaly (60% survival vs. 90%) (FIGS. 15a and 15b). Additionally, it is expected that colons of animals that treated with PSA systemically, have significantly less hyperplasia and inflammatory infiltrate.

The results illustrated in FIG. 16 show that while disease is exacerbated by the increased production of inflammatory cytokines at the site of induction, systemic administration of PSA during TNBS induced colitis suppresses inflammatory cytokines at both intestinal and systemic immune compartments. In particular. TNF-α from Mesenteric Lymph Nodes (MLN) CD4+ T cells is increased in expression during TNBS induced colitis, but is reduced by PSA systemically administered (FIG. 16a). Additionally, inflammatory cytokines IL12p35 IL-23p19 and IL-17 are elevated in the colons of diseased mice, as shown by analysis of transcripts from RNA extracted from colons of mice undergoing TNBS induced colitis, but are reduced by administration of PSA (FIG. 16b). Also in spleen, systemic administration of ZPS reduces the production of TNF-α from CD4+ T lymphocytes within the spleen as shown by the results illustrated in FIG. 16c. Furthermore, systemic administration of ZPS reduces expression of the transcripts IL-17, and IL-6 within the spleen as shown by the results illustrated in FIG. 16d.

Additional experiments also demonstrated that while PSA decreases expression of inflammatory cytokines, intravenous treatment with PSA leads to an elevation in the production of IL-10 within the intestine (supplementary data). These data indicate that systemically administered PSA is capable of extending to mucosal sites and protecting from inflammatory bowel disease.

The data illustrated in this example also show that systemic administration of PSA during TNBS induced colitis suppresses inflammatory cytokines at both intestinal and systemic immune compartments.

Example 11

Parenteral Administration of PSA Modulates Cytokine Expression and Protects from Systemic Inflammation Caused by Th1 and Th17 Cells Endotoxic shock occurs during severe gram-negative bacterial infections and is characterized by hypotension, multi-organ failure and potentially death. This syndrome results from the production of multiple inflammatory cytokines, including TNF-a and IL-6, in response to the lipopolysaccharides (LPS) found in the cell wall of gram negative bacteria. IL-10 has been demonstrated to be a central regulator of the inflammatory response to LPS, indeed a single dose of IL-10 prevents death in murine models of endotoxic shock[42]. The dramatic effects of PSA within the systemic immune compartments lead us to investigate whether PSA could ameliorate systemic inflammation.

To determine whether PSA was capable of suppressing inflammation associated with endotoxic shock Applicants injected Balb/c mice with a low dose (100 ug) of LPS and monitored serum levels of the cytokines TNF-α and IL-6. In particular, serum was collected from mice 1 and 4 hours post-administration of 100 μg or 500 μg of LPS and TNF-α and IL-6 protein levels in the serum were determined by ELISA.

The results illustrated in FIG. 17a to c, show that untreated mice had undetectable levels of serum TNF-α and IL-6 at both time points collected. In particular, consistent with previous studies, in absence of PSA administration, LPS treated mice experienced an over 300 fold increase in serum TNF-α levels that peaked at one hour post injection and decreased to basal levels by four hours post injection (FIG. 17a). In absence of PSA treatment, also IL-6 levels in the serum of LPS injected mice was detectable as early as 1 hour and continues to increase in expression by 4 hours, (FIG. 17b). Remarkably, mice that had been pre-treated with PSA had a significant reduction in serum levels of TNF-α and IL-6 at both time points (FIGS. 17a and 17b), indicating that PSA is able to prevent the early induction of inflammatory cytokines in response to LPS). Additionally, in absence of PSA treatment, splenomegaly occurs within three days of LPS injection and results from the recruitment of inflammatory cell types. Animals pre-treated with PSA, have smaller spleens and express lower levels of inflammatory cytokines at this site (data not shown and FIG. 17c).

This data demonstrates that PSA is capable of suppressing systemic inflammatory responses induced by a low dose administration of LPS.

Example 12

Parenteral Administration of PSA Results in TNF-a Modulation and Treatment Systemic Inflammation Death occurring during endotoxic shock is a result of the elevated levels of inflammatory cytokines that occur within hours of the response to LPS. Indeed, blockage of the inflammatory mediator TNF-α completely rescues animals from LPS induced mortality. That PSA had such a dramatic effect on the levels of the cytokines expressed during low dose administration of LPS, suggested that PSA might prevent death associated with endotoxic shock. Applicants therefore administered high dose levels of LPS (500 that cause death with 24-96 hours and accessed both cytokine levels within the serum and monitored survival.

The results illustrated in FIGS. 17d and 17e, show that while animals that were administered PBS all die within 60 hours of administration of LPS, those animals that received PSA treatment have a significantly increased survival rate (FIG. 17d). Remarkably, while PBS animals have an over 3000 fold induction of TNF-α when administered LPS, those mice receiving PSA have very little TNF-a induction (FIG. 17e). These data demonstrate that PSA is able to suppress the systemic inflammatory response that ensues in response to LPS and is able to protect from septic shock.

As shown in the exemplary experiments of Example 7 PSA mediated protection from IBD is reliant on IL-10 production from a CD4+ T lymphocyte. To determine whether IL-10 is required for protection from LPS induced death Applicants pretreated IL10 deficient animals with PBS or purified PSA and administer levels of LPS that would result in septic shock. The cytokine level and percentage survival were monitored.

Figure 18A:
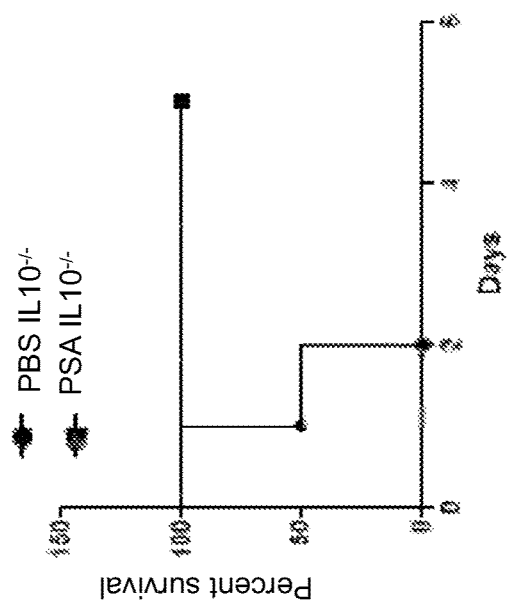
FIG. 18A-18C shows inhibition of inflammation and death associated with systemic septic shock following administration of ZPS according to some embodiments herein disclosed.
Figure 18B:
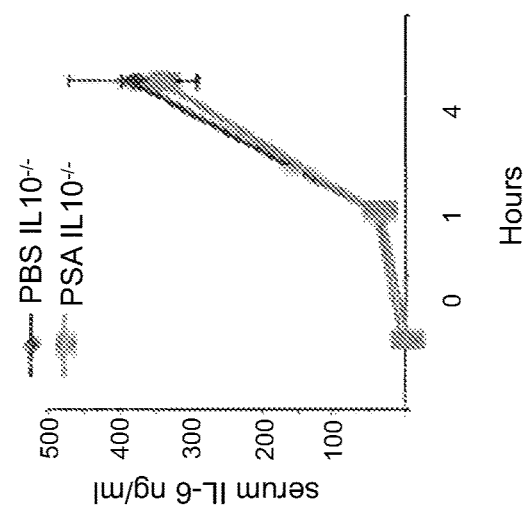
Figure 18C:
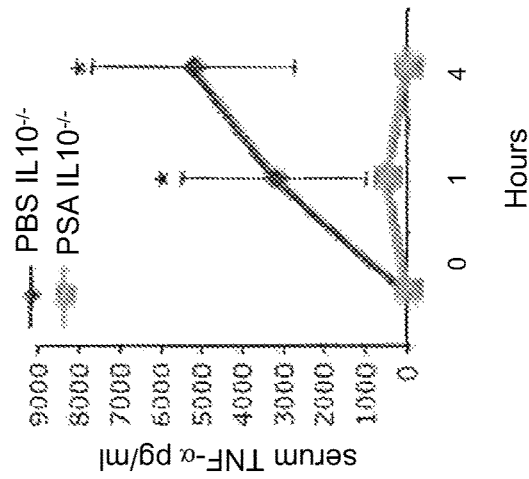

The results illustrated in FIG. 18, show that consistent with previous data IL10-deficient animals were more sensitive to lower doses of LPS and TNF alpha levels continue increase (FIG. 18a). Interestingly, PSA treated animals have a drastic decrease in the levels of serum TNF-a in response to LPS that drops to negligible levels by 4 hours post LPS administration (FIG. 18a), indicating that decreased TNF-a levels by PSA is not dependent on the ability of PSA to induce IL-10. Strikingly, decreased IL-6 production by PSA is IL-10 dependent as levels are similar to PBS treated animals, indicating multiple mechanisms are employed by PSA to alleviate endotoxic shock (FIG. 18b). Finally, IL10 deficient mice receiving PSA are completely protected from LPS induced death (FIG. 18c).

Figure 19:
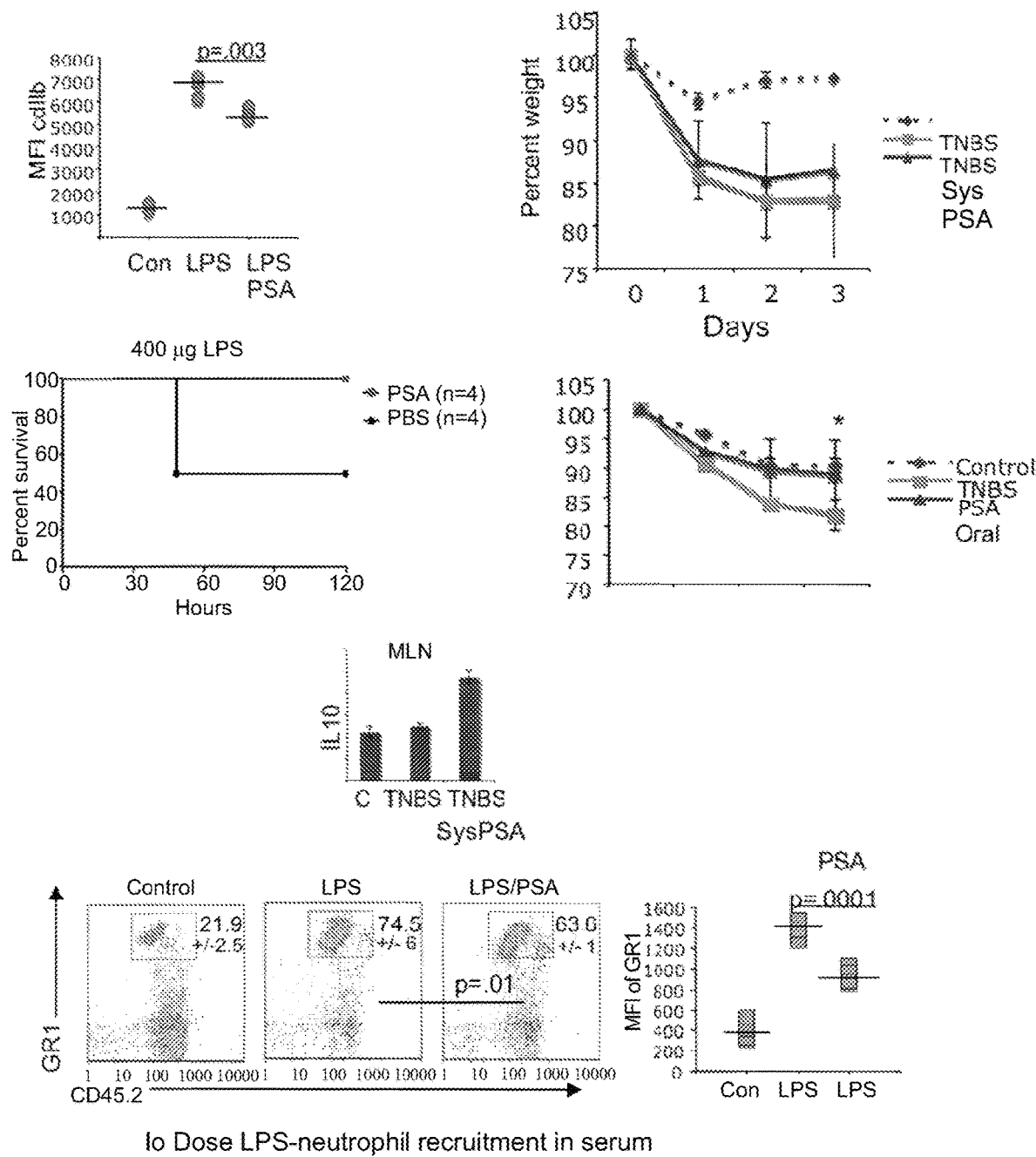
FIG. 19 shows a diagram illustrating additional effects of ZPS administration on inflamed tissues according to some embodiments herein disclosed.

Additional experiments were performed to detect additional effects of PSA administration in connection with low dose LPS administration in mice. The results illustrated in FIG. 19 show that other effects of ZPS administration during low dose LPS administration include a reduction in CD11b and GR1 expression on the surface of neutrophils as well as reduced neutrophil recruitment in the blood.

Taken together, the data of this example and of example indicate that PSA is capable of blocking extra-intestinal disease and is expected to be a novel therapeutic agent to reduce systemic inflammation.

The examples set forth above are provided to give those of ordinary skill in the art a complete disclosure and description of how to make and use the embodiments of the compounds compositions and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

Further, the copy of the sequence listing submitted herewith is incorporated herein by reference in its entirety.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Poxton, I. R., Brown, R., Sawyerr, A. & Ferguson, A. Mucosa-associated bacterial flora of the human colon. J Med Microbiol 46, 85-91 (1997)
2. Sellon, R. K. et al. Resident enteric bacteria are necessary for development of spontaneous colitis and immune system activation in interleukin-10-deficient mice. Infect Immun 66, 5224-31 (1998).
3. Elson, C. O. Commensal bacteria as targets in Crohn's disease. Gastroenterology 119, 254-7 (2000).
4. Sartor, R. B. Mechanisms of disease: pathogenesis of Crohn's disease and ulcerative colitis. Nat Clin Pract Gastroenterol Hepatol 3, 390-407 (2006).
5. Videla, S. et al. Role of intestinal microflora in chronic inflammation and ulceration of the rat colon. Gut 35, 1090-7 (1994).
6. Taurog, J. D. et al. The germfree state prevents development of gut and joint inflammatory disease in HLA-B27 transgenic rats. J Exp Med 180, 2359-64 (1994).
7. Kullberg, M. C. et al. Induction of colitis by a CD4+ T cell clone specific for a bacterial epitope. Proc Natl Acad Sci USA 100, 15830-5 (2003).
8. O'Hara, A. M. & Shanahan, F. The gut flora as a forgotten organ. EMBO Rep 7, 688-93 (2006).
9. Frank, D. N. et al. Molecular-phylogenetic characterization of microbial community imbalances in human inflammatory bowel diseases. Proc Natl Acad Sci USA 104, 13780-5 (2007).
10. Gill, S. R. et al. Metagenomic analysis of the human distal gut microbiome. Science 312, 1355-9 (2006).
11. Ley, R. E., Peterson, D. A. & Gordon, J. I. Ecological and evolutionary forces shaping microbial diversity in the human intestine. Cell 124, 837-48 (2006).
12. Smith, K., McCoy, K. D. & Macpherson, A. J. Use of axenic animals in studying the adaptation of mammals to their commensal intestinal microbiota. Semin Immunol (2006).
13. Mazmanian, S. K., Liu, C. H., Tzianabos, A. O. & Kasper, D. L. An immunomodulatory molecule of symbiotic bacteria directs maturation of the host immune system. Cell 122, 107-18 (2005).
14. Pamer, E. G. Immune responses to commensal and environmental microbes. Nat Immunol 8, 1173-8 (2007).

15. Dethlefsen, L., McFall-Ngai, M. & Relman, D. A. An ecological and evolutionary perspective on human-microbe mutualism and disease. Nature 449, 811-8 (2007).
16. Bell, E. B. Function of CD4 T cell subsets in vivo: expression of CD45R isoforms. Semin Immunol 4, 43-50 (1992).
17. Izcue, A., Coombes, J. L. & Powrie, F. Regulatory T cells suppress systemic and mucosal immune activation to control intestinal inflammation. Immunol Rev 212, 256-71 (2006).
18. Maloy, K. J. et al. CD4+CD25+ T(R) cells suppress innate immune pathology through cytokine-dependent mechanisms. J Exp Med 197, 111-9 (2003).
19. Cahill, R. J. et al. Inflammatory bowel disease: an immunity-mediated condition triggered by bacterial infection with *Helicobacter hepaticus*. Infect Immun 65, 3126-31 (1997).
20. Scheinin, T., Butler, D. M., Salway, F., Scallon, B. & Feldmann, M. Validation of the interleukin-10 knockout mouse model of colitis: antitumour necrosis factor-antibodies suppress the progression of colitis. Clin Exp Immunol 133, 38-43 (2003).
21. Kullberg, M. C. et al. Bacteria-triggered CD4(+) T regulatory cells suppress *Helicobacter hepaticus*-induced colitis. J Exp Med 196, 505-15 (2002).
22. Bregenholt, S. Cells and cytokines in the pathogenesis of inflammatory bowel disease: new insights from mouse T cell transfer models. Exp Clin Immunogenet 17, 115-29 (2000).
23. Powrie, F. & Maloy, K. J. Immunology. Regulating the regulators. Science 299, 1030-1 (2003).
24. Xavier, R. & Podolsky, D. K. Commensal flora: wolf in sheep's clothing. Gastroenterology 128, 1122-6 (2005).
25. Rutgeerts, P. et al. Infliximab for induction and maintenance therapy for ulcerative colitis. N Engl J Med 353, 2462-76 (2005).
26. Rakoff-Nahoum, S., Paglino, J., Eslami-Varzaneh, F., Edberg, S. & Medzhitov, R. Recognition of commensal microflora by toll-like receptors is required for intestinal homeostasis. Cell 118, 229-41 (2004).
27. Kullberg, M. C. et al. IL-23 plays a key role in *Helicobacter hepaticus*-induced T cell-dependent colitis. J Exp Med 203, 2485-94 (2006).
28. Hue, S. et al. Interleukin-23 drives innate and T cell-mediated intestinal inflammation. J Exp Med 203, 2473-83 (2006).
29. Tzianabos, A. O. et al. The capsular polysaccharide of *Bacteroides fragilis* comprises two ionically linked polysaccharides. J Biol Chem 267, 18230-5 (1992).
30. Elson, C. O. et al. Monoclonal anti-interleukin 23 reverses active colitis in a T cell-mediated model in mice. Gastroenterology 132, 2359-70 (2007).
31. Kuhn, R., Lohler, J., Rennick, D., Rajewsky, K. & Muller, W. Interleukin-10-deficient mice develop chronic enterocolitis. Cell 75, 263-74 (1993).
32. Asseman, C., Mauze, S., Leach, M. W., Coffman, R. L. & Powrie, F. An essential role for interleukin 10 in the function of regulatory T cells that inhibit intestinal inflammation. J Exp Med 190, 995-1004 (1999).
33. Groux, H. et al. A CD4+ T-cell subset inhibits antigen-specific T-cell responses and prevents colitis. Nature 389, 737-42 (1997).
34. Strachan, D. P. Hay fever, hygiene, and household size. Bmj 299, 1259-60 (1989).
35. Bach, J. F. The effect of infections on susceptibility to autoimmune and allergic diseases. N Engl J Med 347, 911-20 (2002).
36. Liu, C. H., Lee, S. M., Vanlare, J. M., Kasper, D. L. & Mazmanian, S. K. Regulation of surface architecture by symbiotic bacteria mediates host colonization. Proc Natl Acad Sci USA 105, 3951-6 (2008).
37. Turnbaugh, P. J. et al. An obesity-associated gut microbiome with increased capacity for energy harvest. Nature 444, 1027-31 (2006).
38. Mazmanian, S. K. & Kasper, D. L. The love-hate relationship between bacterial polysaccharides and the host immune system. Nat Rev Immunol (2006).
39. Young, V. B. et al. In vitro and in vivo characterization of *Helicobacter hepaticus* cytolethal distending toxin mutants. Infect Immun 72, 2521-7 (2004).
40. Mazmanian, S. K., Liu, C. H., Tzianabos, A. O. & Kasper, D. L. An immunomodulatory molecule of symbiotic bacteria directs maturation of the host immune system. Cell 122, 107-18 (2005).
41. Rakoff-Nahoum, S., Paglino, J., Eslami-Varzaneh, F., Edberg, S. & Medzhitov, R. Recognition of commensal microflora by toll-like receptors is required for intestinal homeostasis. Cell 118, 229-41 (2004).
42. C Gerard, C Bruyns, A Marchant, D Abramowicz, P Vandenabeele, A Delvaux, W Fiers, M Goldman, and T Velu Interleukin 10 reduces the release of tumor necrosis factor and prevents lethality in experimental endotoxemia J. Exp. Med. 1993 177: 547-550
43. Sarkis K. Mazmanian, June L. Round & Dennis L. Kasper2, A microbial symbiosis factor prevents intestinal inflammatory disease Nature Vol 453, 29 May 2008, 620-625

What is claimed is:

1. A method of treating inflammatory bowel disease, comprising:
    identifying a subject in need, wherein the subject has an inflammatory bowel disease and an imbalanced T-helper cell profile, wherein the imbalanced T-helper cell profile comprises an imbalance of a T-helper 1 (Th1) cell profile and/or a T-helper 17 (Th17) cell profile in the intestinal compartment of the subject; and
    administering to the subject in need an amount of *B. fragilis* expressing polysaccharide A (PSA) sufficient to colonize the subject via enteral administration, thereby reducing the imbalanced T-helper profile in the intestinal compartment of the subject, thereby treating the subject of the inflammatory bowel disease.

2. A method of protecting a subject from T-cell mediated inflammatory disease, comprising:
    identifying a subject in need, wherein the subject has an imbalanced T-helper cell profile, wherein the imbalanced T-helper cell profile comprises an imbalance of a T-helper 1 (Th1) cell profile and/or a T-helper 17 (Th17) cell profile in the intestinal compartment of the subject; and
    administering to the subject in need an amount of *B. fragilis* expressing polysaccharide A (PSA) sufficient to colonize the subject via enteral administration, thereby reducing the imbalanced T-helper profile in the intestinal compartment of the subject, thereby protecting the subject from T-cell mediated inflammatory disease.

3. The method of claim 2, wherein the inflammatory disease is colitis.

4. The method of claim 2, wherein the inflammatory disease is inflammatory bowel disease.

5. A method of reducing cytokine production in a subject, the cytokine being tumor necrosis factor alpha (TNF-α) and/or interleukin-17 (IL-17), the method comprising:
    administering to the subject via enteral administration an amount of a *B. fragilis* expressing polysaccharide A (PSA) effective to reduce production of TNF-α and/or IL-17,
    wherein the subject has been determined to have an imbalanced T-helper cell profile, wherein the imbalanced T-helper cell profile comprises an imbalance of a T-helper 1 (Th1) cell profile and/or a T-helper 17 (Th17) cell profile in the intestinal compartment, and
    wherein the amount of *B. fragilis* expressing PSA is sufficient to colonize the subject.

6. The method of claim 5, where the amount of a *B. fragilis* expressing PSA is effective to increase the production of Interleukin 10 (IL-10).

7. The method of claim 5, wherein the subject has an inflammatory disease.

8. The method of claim 7, wherein the inflammatory disease comprises inflammatory bowel disease, Crohn's disease, ulcerative colitis, asthma, dermatitis, arthritis, myasthenia gravis, Grave's disease, sclerosis, psoriasis, or any combination thereof.

9. The method of claim 1, wherein the administration reduces the levels of tumor necrosis factor alpha (TNF-α) and/or interleukin-17 (IL-17) in the subject.

10. The method of claim 2, wherein the administration reduces the levels of tumor necrosis factor alpha (TNF-α) and/or interleukin-17 (IL-17) in the subject.

11. The method of claim 1, wherein the enteral administration comprises oral administration, rectal administration, or a combination thereof.

12. The method of claim 2, wherein the enteral administration comprises oral administration, rectal administration, or a combination thereof.

13. The method of claim 5, wherein the enteral administration comprises oral administration, rectal administration, or a combination thereof.

\* \* \* \* \*

SEQUENCE LISTING

<160> NUMBER OF SEQ ID NOS: 18

<210> SEQ ID NO 1
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 1
gaaactgtta ctctg                                                    15

<210> SEQ ID NO 2
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 2
tcaagctccc cgaaggg                                                      17

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
tatttgcgag aaggtgat                                                     18

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
taaacgcttt gctgctat                                                     18

<210> SEQ ID NO 5
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 5
agctatgaat ctactaagag agggaca                                           27

<210> SEQ ID NO 6
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 6
gtcctagtag ggaggtgtga agttg                                             25

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
ttaaggttct ctcctctgaa                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
```

```
tagggagcta aattatccaa                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
acggcatgga tctcaaagac                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
gtgggtgagg agcacgtagt                                              20

<210> SEQ ID NO 11
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 11
ctggacaaca tactgctaac cg                                           22

<210> SEQ ID NO 12
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 12
gggcatcact tctaccaggt aa                                           22

<210> SEQ ID NO 13
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 13
ccgctgagag ggcttcac                                                18

<210> SEQ ID NO 14
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 14
tgcaggagta ggccacatta ca                                           22

<210> SEQ ID NO 15
<211> LENGTH: 24
<212> TYPE: DNA
<213> ORGANISM: Artificial Sequence
```

```
<220> FEATURE:
<223> OTHER INFORMATION: Synthetic Polynucleotide

<400> SEQUENCE: 15
atcctgaact tctatcagct ccac                                              24

<210> SEQ ID NO 16
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 16
gcatttagct atgtgcttct gtttc                                             25

<210> SEQ ID NO 17
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 17
ctgttgctgc tacccttgct t                                                 21

<210> SEQ ID NO 18
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 18
cactcctggc aatcgagatt c                                                 21
```